(12) United States Patent
Shvets et al.

(10) Patent No.: US 6,669,909 B2
(45) Date of Patent: Dec. 30, 2003

(54) LIQUID DROPLET DISPENSING

(75) Inventors: Igor Shvets, Castleknock (IE); Sergei Makarov, Dublin 8 (IE); Alexander Shvets, Castleknock (IE); Juergen Osing, Rialto (IE)

(73) Assignee: Allegro Technologies Limited, Dublin (IE)

( * ) Notice: Subject to any disclaimer, the term of this patent is extended or adjusted under 35 U.S.C. 154(b) by 246 days.

(21) Appl. No.: 09/816,326

(22) Filed: Mar. 26, 2001

(65) Prior Publication Data

US 2002/0177237 A1 Nov. 28, 2002

(51) Int. Cl.[7] ............................. B01L 3/02; G01N 1/10; G01N 1/14; F16K 31/02; F16K 31/12

(52) U.S. Cl. ...................... 422/100; 422/103; 436/180; 73/863.32; 73/863.71; 73/864; 73/864.01; 73/864.02; 73/864.11; 73/864.13; 73/864.34; 251/129.08; 251/129.18; 137/487.5

(58) Field of Search ................. 422/100, 103, 422/105; 436/180; 73/863.32, 863.71, 863.86, 864, 864.01, 864.02, 864.11, 864.13, 864.34; 251/129.08, 129.18; 137/487.5

(56) References Cited

U.S. PATENT DOCUMENTS

| 4,229,413 | A | * | 10/1980 | Marteau d'Autry | ......... 422/100 |
|---|---|---|---|---|---|
| 4,541,787 | A | | 9/1985 | DeLong | |
| 4,574,850 | A | | 3/1986 | Davis | |
| 4,965,864 | A | | 10/1990 | Roth et al. | |
| 5,035,150 | A | | 7/1991 | Tompkins | |
| 5,525,515 | A | * | 6/1996 | Blattner | ........................ 436/49 |
| 5,741,554 | A | | 4/1998 | Tisone | |
| 5,744,099 | A | | 4/1998 | Chase et al. | |
| 5,758,666 | A | | 6/1998 | Larson, Jr. et al. | |
| 5,916,524 | A | * | 6/1999 | Tisone | ........................ 422/100 |
| 6,063,339 | A | * | 5/2000 | Tisone et al. | .................. 422/67 |
| 6,116,269 | A | * | 9/2000 | Maxson | .................... 137/487.5 |
| 6,133,044 | A | * | 10/2000 | Van den Engh | ............. 436/177 |
| 6,135,325 | A | * | 10/2000 | Fessel et al. | ................ 222/309 |
| 6,223,761 | B1 | * | 5/2001 | Najmolhoda et al. | ......... 137/14 |
| 6,293,514 | B1 | * | 9/2001 | Pechoux et al. | ............. 251/122 |

(List continued on next page.)

FOREIGN PATENT DOCUMENTS

| EP | 0 457 389 | 5/1991 |
|---|---|---|
| EP | 1099484 A1 | 5/2001 |
| WO | WO 98/52640 | 3/1998 |
| WO | WO 99/42752 | 2/1999 |

*Primary Examiner*—Jill Warden
*Assistant Examiner*—Brian R. Gordon
(74) *Attorney, Agent, or Firm*—Birch, Stewart, Kolasch & Birch, LLP

(57) ABSTRACT

A dispenser (1) for liquid droplets of the order of 30 μl or less in volume. The dispenser (1) comprises a metering valve body (2) having a main bore (3) connected by a pipe (4) to a pressurised liquid delivery source (not shown). The body (2) comprises a base (5) from which is mounted a nozzle (6) projecting above the base (5) to form a valve seat (7). An actuating coil assembly (11) is mounted on the exterior of the body (2) for moving a floating valve boss (15) of a ferromagnetic material. Sensing coils (20, 21) are mounted around and spaced-apart along the body (2) forming part of a valve boss detector. The valve boss detector acts as a positional movement detector so that the opening and closing of the valve can be accurately controlled and bouncing of the valve boss (15) either against an end stop (9) or on the valve seat (7) can be greatly minimized, if not prevented fully, by careful operation of the actuating coil assembly (11).

36 Claims, 40 Drawing Sheets

U.S. PATENT DOCUMENTS

| | | | |
|---|---|---|---|
| 6,378,545 B1 * | 4/2002 | Bozkan et al. | 137/82 |
| 6,394,415 B1 * | 5/2002 | Ohmi et al. | 251/129.16 |
| 6,416,718 B1 * | 7/2002 | Maiefski et al. | 422/103 |
| 6,422,259 B1 * | 7/2002 | Moreno | 137/15.18 |
| 6,537,505 B1 * | 3/2003 | LaBudde et al. | 422/103 |
| 6,543,744 B2 * | 4/2003 | Carrillo et al. | 251/129.08 |
| 2001/0004449 A1 * | 6/2001 | Suzuki et al. | 422/100 |
| 2001/0016358 A1 * | 8/2001 | Osawa et al. | 436/180 |
| 2001/0052585 A1 * | 12/2001 | Righolt et al. | 251/129.18 |
| 2002/0088493 A1 * | 7/2002 | Suzuki | 137/487.5 |
| 2002/0117644 A1 * | 8/2002 | Carrillo et al. | 251/129.08 |
| 2002/0131903 A1 * | 9/2002 | Ingenhoven et al. | 422/100 |

* cited by examiner

US 6,669,909 B2

LIQUID DROPLET DISPENSING

FIELD OF THE INVENTION

The present invention relates to a dispensing assembly for liquid droplets of the order of 30 µl in volume and as low as 10 nl or even smaller. Further, the invention is directed towards providing a method for dispensing such liquids and measurement of their properties.

The present invention relates to an assembly for dispensing and aspirating small volumes of liquid as used extensively for drug development in pharmaceutical, medical diagnostics, biotechnology and indeed small droplets of liquid as used extensively for many techniques in industry. Particular examples of this are High Throughput Screening (HTS), Polymerase Chain Reaction (PCR), combinatorial chemistry, microarraying, and proteomics, although obviously not limited to those. In the area of high throughput screening, PCR, proteomics and combinatorial chemistry, the typical application for such a liquid handling system is in dispensing of small volumes of liquids, for example, 1 ml and smaller and in particular volumes around 1 µl and smaller. The invention is also directed to the aspiration of liquids from sample wells so that the liquids can be transferred between wells. The invention relates also to microarray technology, a recent advance in the field of high throughput screening and genomics. Microarray technology is being used for applications such as DNA and protein arrays: in this technology the arrays are created on glass or polymer slides. The fluid handling system for this technology is directed to dispensing consistent droplets of liquids of submicroliter volume. The present invention is also directed to medical diagnostics, for example, for applications such as single nucleotide polymorphism or others.

Development of instrumentation for dispensing of minute volumes of liquids has been an important area of technological activity for some time. Numerous devices for the controlled dispensing of small volumes of liquids (in the range of 1 µl and smaller) for ink jet printing application have been developed over the past twenty five years. More recently, a wide range of new areas of applications has emerged for devices handling liquids in the low microliter range.

The requirements of a dispensing system vary significantly depending on the application. For example, the main requirement of a dispensing system for ink jet applications is to deliver droplets of a fixed volume with a high repetition rate. The separation between individual nozzles should be as small as possible so that many nozzles can be accommodated on a single printing cartridge. On the other hand in this application the task is simplified by the fact that the mechanical properties of the liquid dispensed namely ink are well-defined and consistent. Also in most cases the device used in the ink jet applications does not need to aspire the liquid through the nozzle for the cartridge refill.

For biomedical applications such as High Throughput Screening (HTS), the requirements imposed on a dispensing system are completely different. The system should be capable of handling a variety of reagents with different mechanical properties e.g. viscosity. Usually these systems should also be capable of aspiring the liquids through the nozzle from a well. On the other hand there is not such a demanding requirement for the high repetition rate of drops as in ink jet applications. Another requirement in the HTS applications is that cross contamination, between different wells served by the same dispensing device, be avoided as much as possible.

DETAILED DESCRIPTION OF PRIOR ART

The most common method of liquid handling for the HTS applications is based on a positive displacement pump such as described in U.S. Pat. No. 5,744,099 (Chase et al). The pump consists of a syringe with a plunger driven by a motor, usually a stepper or servo-motor. The syringe is usually connected to the nozzle of the liquid handling system by means of flexible polymer tubing. The nozzle is typically attached to an arm of a robotic system which carries it between different wells for aspiring and dispensing the liquids. The syringe is filled with a system liquid such as water. The system liquid continuously extends through the flexible tubing into the nozzle down towards the tip. The liquid reagent which needs to be dispensed, fills up into the nozzle from the tip. In order to avoid mixing of the system liquid and the sample liquid and therefore cross-contamination, an air bubble or bubble of another gas is usually left between them. This method does not allow reliable dispensing of droplets in the volume range below some 1 to 5 microliters. Somewhat smaller volumes can be dispensed if the tip of the dispenser touches the substrate to release the drop. The compressibility of the gas bubble between the reagent and the system liquid is a significant source of error. Examples of such positive displacement pumps are shown in U.S. Pat. No. 5,744,099 (Chase et al). Similarly the problems of dispensing drops of small volume are also described and discussed in U.S. Pat. No. 4,574,850 (Davis) and U.S. Pat. No. 5,035,150 (Tomkins).

Dispensing of drops of liquids using a conventional solenoid valve is well known. It has been used in ink printing applications for more than a decade. As explained below, there are still major problems associated with the use of a conventional solenoid valve for dispensing of minute droplets of reagents for biomedical and pharmaceutical applications.

U.S. Pat. No. 5,741,554 (Tisone) describes another method of dispensing submicroliter volumes of fluids for biomedical application and in particular for depositing bodily fluids and reagents on diagnostic test strips. This method combines a positive displacement pump and a conventional solenoid valve. The positive displacement pump is a syringe pump filled with a fluid to be dispensed. The pump is connected to tubing at the other end which there is a solenoid valve located close to the ejection nozzle. The tubing is also filled with the fluid to be dispensed. In this method the piston of the pump is driven by a motor with a well-defined constant speed. The speed determines the flow rate of the fluid from the nozzle provided the solenoid valve is opened frequently enough and the duty cycle between opening and closing of the valve is long enough. The solenoid valve is actuated with a defined repetition rate. The repetition rate of the valve and the flow rate of the pump determine the size of each drop. For example, if the pump operates at a flow rate of 1 µl per second and the repetition rate is 100 open-close cycles per second, then the size of each drop in theory is 10 nl. This method is suitable for dispensing of large number of identical droplets. However, for dispensing of liquids for HTS applications, this method is often inappropriate since it is commonly required to aspire a liquid through the nozzle in small quantities (say 1 µl) and then dispense it in fractions of this quantity, say in a series of only five drops or even a single drop on demand. To avoid mixing of the liquid aspired with the one in the syringe pump, it is probably necessary to place a bubble of gas in the tube with the attendant problems described above. Without such a bubble, if the solenoid valve open time and/or operating frequency are too small for a given pump flow rate, the pressure in the dispenser will become too great, causing possible rupture or malfunctioning of the system. Another disadvantage of this solution is that the heat from the coil actuating the plunger of the valve may cause a heating of the liquid in the valve that can be a serious problem for some applications. Besides, for some regimes of operation the drops may amalgamate, e.g. one drop will be released for every two or three actuations of the valve.

As the solenoid valve is normally not used as a disposable element due to its high cost, the used portion or potentially contaminated chamber of the valve needs to be washed frequently to avoid cross contamination. This is a major issue for HTS applications and microarraying as the dispenser typically switches from one liquid to another up to several times a minute. The fluid path in the valve is torturous, the valve contains a number of parts and pockets where the contamination can build up complicating the cleaning routine.

Various attempts in the past have been made to address the problem of such conventional solenoid valves. A typical example of these is the invention described in PCT Patent Specification No. WO 99/42752 (Labudde). This patent specification discusses the problems associated with using conventional solenoid valves for many HTS applications. Various solutions to the problem are proposed. None of these, it is suggested, overcome the major problems of the use of conventional solenoid valves for these applications. Relatively complex constructions of actuator and plungers with diaphragms are described. The invention of this patent specification is directed to the problem of bubble formation in the valve and aspiration. WO 99/42752 (Labudde) discusses in some detail the problems relating to the structure and geometry of the valve. The solution proposed is to design a "non torturous" flow path for the liquid. In this patent specification, the effect of the use of a blunt or rounded valve seat is discussed as well as the effect of the area of the valve seat orifice opening. This specification discloses a valve seat with an internal diameter of the order of 7.5 mm. Further, in this latter patent specification, the plunger of the valve is attached to a diaphragm limiting its movement. The displacement of the plunger between the open and closed position is of the order of 50 μm. There is also a discussion in this patent specification of the heating effects and a solution is proposed by separating the actuating coil from the valve. U.S. Pat. No. 5,741,554 (Tisone) again describes substantially the same construction.

Patent Specification No. WO 98/52640 (Shalom) describes a flow control device for medical infusion systems. These systems are used for the slow injection of relatively large volumes, namely milliliters up to a liter, into a patient over a relatively long period of minutes, if not hours. Essentially, there is described a system for the slow injection of fluids into a patient with real time control of the process. The system uses valves to mix or select fluids coming from a number of inlets and to route their flow via selected outlets. It is suggested that this specification does not teach that such a valve would be suitable for the dispensing of droplets of liquid with volumes of the order of 5 nl at a high frequency. In this patent specification, there is illustrated an actuation coil embedded in the body of the valve and the use of spherical magnetic bosses or a multiple of bosses, to increase the resistance of fluid flow through the valve.

U.S. Pat. No. 5,758,666 (Larson et al) describes a surgically implantable reciprocating pump having a floating piston made of a permanent magnetic material and incorporating a check valve. The piston can be moved by means of energising coils in a suitable timing sequence. The piston allows the flow of liquid through it when it moves in one direction as the check valve is open, and when it moves in the opposite direction, the check valve is closed and the liquid is pumped by the piston.

U.S. Pat. No. 4,541,787 (DeLong) describes an electromagnetic reciprocating pump with a "magnetically responsive" piston so called as it contains some ferromagnetic material. The piston is actuated by at least two coils located outside the cylinder containing the piston. The coils are energised by a current with a required timing.

It has become apparent that accurate control of the valve boss is all important. Indeed, there are known linear and rotary motors in which movement of a piston or a shaft of a permanent magnetic material is controlled by a series of driving coils. To achieve reliable operation of the motor, signals applied to coils must be synchronised with the movement of the shaft. For example, there can be ten or so driving coils spaced apart and positioned along the length of the motor to achieve a significant stroke of the shaft. It is clear that at any given moment only those one or two coils that are positioned close to the shaft must be energised and the one or two coils located just behind the shaft must be de-energised. As the shaft moves, successive one or two coils located further down its path are energised and so on. Therefore the motor controller must follow movement of the shaft and must be aware of its current position. This is achieved by detecting electromotive force induced in the driving coils. U.S. Pat. No. 4,965,864 (Roth et al) is an example of this type of motor. This patent however, does not deal with dispensing of small volumes of liquids.

There are also known other devices for the detection of movement of a magnetic shaft. In a typical embodiment disclosed in European Patent Specification No 457,389 A1 (van Alem), there are three coils driving a shaft of a magnetic material. The coils are positioned along the length of the shaft's path. The central of the three driving coils is also supplied with an AC current. Electromagnetic coupling between the driving coils depends on the position of the shaft. This patent does not deal with dispensing of small volumes of liquids. The device described in this patent specification falls under the category of devices called Linear Variable Differential Transformers (LVDT). These devices are used as position sensors and are manufactured by a number of companies such as e.g. Solartron Metrology Ltd (LVDT type SMI manufactured by Solartron Metrology Ltd, Steyning Way, Southern Cross Industrial Estate, Bognor Regis, PO22 9ST West Sussex, UK).

In summary, there is a major problem in finding a suitable way of dispensing submicroliter volumes for applications as described above such as HTS applications. This problem can be said to be currently the bottleneck in changing to assay formats of higher density. Numerous publications in the specialised literature indicate that a technical solution to this problem has not been found so far and further that it is necessary to find them. Our work to date indicates that if accurate dispensing of submicroliter volumes is to be achieved, it can only be done with solenoid valves having a floating boss.

Other methods of dispensing of small volumes of liquids were proposed recently in various patent specifications (EPO 00650123.3 and EPO 99650106.0, Shvets). The methods are based on a floating boss valve. In a typical dispensing assembly, the boss, made of a ferromagnetic material, is placed inside a body member of a dispenser mounting a nozzle. The boss is actuated by an external magnetic field. As a result the boss can close and open the nozzle bore of the dispenser. The liquid in the dispensing assembly is pressurized by a pressure source. When the boss is removed from the nozzle bore, the liquid is transported by pressure towards the dispensing tip resulting in a dispensing of a drop or droplet of the liquid stored in the dispensing assembly. The source of the magnetic field actuating the boss is located adjacent to the body member of the dispensing assembly and the magnetic boss. It could consist of a magnetic coil or an assembly of magnetic coils or coils wound on a core of magnetic material. Alternatively it could consist of an assembly of permanent magnets coupled by magnetostatic forces with the boss. Such a magnetic assembly can be caused to move by using, for example, a pneumatic actuator thus causing the movement of the boss. The means are also provided to detach the droplet from the nozzle by using the electrostatic field generated at the end of the tip. There are also means provided to measure the mass of the droplet through the measurement of the charge carried by the droplet. There are also means provided for navigating droplets to desired locations within the well plate. It should be pointed that there are also other embodiments described in the patent applications EPO 00650123.3 and EPO 99650106.0 that are not based on a floating boss. The common feature of most embodiments is a soft compressible seal between portion of a capillary forming a nozzle bore and a boss or plunger. This portion of the nozzle forms a valve seat. In the preferred embodiment of EPO 00650123.3, the compressible seal is formed between a valve seat formed by part of a rigid capillary forming the nozzle bore and a soft polymer attached to the surface of the boss/plunger coming in contact with the capillary. In most embodiments there is also a stopper located inside the body member of the dispenser to ensure that the boss always remains positioned in the area where it can be efficiently coupled to the source of magnetic field actuating the boss. It is clear from the technical disclosure of these patent applications that the accuracy of dispensing critically depends on the accuracy of the time interval during which the nozzle bore is open during the dispensing. The time interval during which the nozzle bore is open, is determined by the pattern of the current in the coil assembly actuating the boss/plunger.

Unfortunately it is difficult to predict and thus know the moment of opening and closing of the valve seat even if the current actuating the boss is known. This is caused by the fact that one of the two elements: the boss or the valve seat, must be made of a soft material to ensure that the seal of the boss against the nozzle bore is pneumatically tight. This soft material is compressed when the boss is pressed against the nozzle bore. As a result, movement of the boss away from the valve seat at the start of the dispensation does not immediately result in the opening of the valve seat and flow of the liquid through the nozzle bore. There is a time delay between the start of the movement of the boss and the separation from the valve seat that depends mainly on the compressibility of the seal and the pressure in the dispenser. This time delay between the two events can have a particularly significant effect on the accuracy of dispensing for drops of small volume, as the opening time required to deliver a small drop to the end of the nozzle is particularly short. Indeed, for dispensing of drops in the volume range of 10 nl, the desired opening time interval of the dispenser could be as short as some 1 ms or even smaller. This time depends on the diameter of the nozzle, length of the capillary and viscosity of the liquid dispensed. For droplets of sub-microliter volume, the inaccuracy in the control of the moment of opening of the valve seat can, in some circumstances, be a significant source of error.

Additional loss of accuracy of dispensing comes at the moment of closing of the valve seat. The reason is that at the moment when the current in the actuating coil is sent to close the valve seat, the position of the boss is not known. For example if the valve was only open for a short time prior to the moment of closure, the boss would not move far away from the valve seat and would not come to rest against a stopper. Therefore in this case it would take it a shorter time to reach back the valve seat and close the valve than if it was pressed against the stopper. The position of the boss is difficult to predict on the basis of the time that has elapsed since the moment of opening of the valve. The position will depend on a number of factors including, for example, viscosity of the liquid in the dispenser. If the time between the moments of opening and closing of the valve boss is sufficiently long so that the boss has come in contact with the stopper, an additional source of error will come from the fact that the boss can bounce back from the stopper. If the boss bounces back from the stopper, then in contrast to common sense expectations, increasing of the time interval during which the boss is open could, as we have found, result in decrease in the volume of the liquid dispensed. This is discussed in more detail below.

Another source of error comes from the fact that the boss can also bounce back when it reaches the valve seat. If the bouncing is significant, then this could result in an additional uncontrollable opening of the valve and therefore, additional uncontrollable delivery of the liquid through the nozzle to the tip.

Most of these factors become more significant for droplets of small volume for at least two reasons. Firstly, the opening time of the valve for droplets of small volume is shorter than for droplets of large volume and the volume of the drop is proportional to the opening time of the valve. Therefore the time inaccuracies associated with bouncing of the boss and compressibility of the valve seal increase relatively in comparison with the opening time of the valve. Secondly, to ensure a shorter opening time of the valve, the boss must move faster. Therefore, as the velocity of the boss increases, so will the tendency of the boss to bounce back from both the valve seat and the stopper.

It would be advantageous to measure properties of the liquid during the dispensing such as, for example, its viscosity. Simplistically, if one knew the viscosity of the liquid, then one would know firstly when the liquid had become diluted or had changed its properties or alternatively one would know, for example, when there was no liquid in the dispenser. Most of the current dispensing technologies do not allow for this kind of measurement. The present invention is directed towards providing an improved method and apparatus for dispensing droplets as small as 10 nl ($10^{-8}$ l) or even smaller, while at the same time it should be possible to dispense larger droplets such as those as large as 10 micro liters or even greater.

Another objective is to provide a method where the quantity of the fluid dispensed can be freely selected by the operator and accurately controlled by the dispensing system. The system should be capable of dispensing a drop of one size followed by a drop of a widely differing size, for example, a 10 nl drop followed by a 500 nl one.

The invention is also directed towards providing a method where the fluid can be dispensed on demand, i.e. one quantity can be dispensed at a required time as opposed to a series of dispensations with set periodic time intervals between them. Yet, the method should also allow for dispensation of doses with regular intervals between subsequent dispensations, for example, printing with liquids.

Another objective of the present invention is to provide a method and a dispensing device suitable for dispensing a liquid from a supply line to a target well and also for aspirating a liquid from the sample well into the supply line. The device should ideally be able to control accurately the amount of the liquid aspired into the nozzle of the dispenser from a supply well.

Another objective is to provide a method for handling fluids in a robotic system for high throughput screening or microarraying which would be suitable for accurate dispensing and aspiring volumes smaller than the ones obtainable with current positive displacement pumps.

Yet another objective is to provide means of measurement of viscosity and density of the liquid dispensed during the dispensations. Another objective is to enable detection of the moment when the dispenser runs out of liquid and requires refill.

SUMMARY OF THE INVENTION

Exemplary embodiments of the present invention provide a dispensing assembly for liquid droplets of the order of 30 $\mu$l or less in volume and also various control circuits for such a dispensing assembly as well as a method of dispensing liquid droplets of the order of 30 $\mu$l or less in volume in a dispensing assembly using a pressurised delivery source.

One such dispensing assembly comprises a pressurised liquid delivery source and a dispenser having a metering valve body connected to the liquid delivery source, the body being generally an elongate body member having an internal main bore and a base forming an apertured valve seat. The metering valve body has mounted in its bore, a floating valve boss, that is to say, a valve boss that is not connected to any external rod or actuator. The cross-sectional area of the valve boss is sufficiently less than that of the main bore to permit the free passage of liquid therebetween. The dispenser carries a nozzle mounted on the base of the body member which nozzle comprises a dispensing tip and has a nozzle bore communicating between the valve seat and the dispensing tip. A variable power output valve actuator is used for moving the valve boss in the bore between a closed position engaging the valve seat and an open position spaced-apart from the valve boss. Usually, an end stopper will be provided to retain the valve boss within the metering valve body and in many instances will define the open position.

The invention provides a valve boss detector for determining the movement of the valve boss within the bore. This may be a position sensor, it can be a velocity or acceleration sensor, namely, any movement sensor generally. Further, there is provided a controller connected to the valve boss detector and to the valve boss actuator for varying the power input to the valve boss actuator depending on the movement of the valve boss within the bore. Thus, by use of the detector, much more accurate dispensing can be obtained with a floating valve boss, the advantage of the invention being to ensure that there is accurate motion control of the valve boss. It is much more effective than a conventional solenoid valve.

Ideally, the nozzle or at least that portion of it adjacent the tip, is manufactured of a hydrophobic material to encourage separation of the droplet from the dispensing tip. The valve boss will generally be a ferromagnetic material and the actuator will often be a current actuating coil assembly. Various valve boss detectors such as Hall sensors may be provided. The actuator can be one actuating coil, it can be a pair of spaced-apart actuating coils and the sensors may be, for example, two spaced-apart sensing coils. The position sensor, forming part of the valve boss detector, may, for example, be an alternating current powered sensing coil or coils. A parametric oscillator circuit may be used in the position sensor. More than one sensing coil may be used.

In one embodiment of the invention, the dispensing assembly includes a plurality of nozzles mounted on the base of the one body member. Various detection circuits may be used.

Further, the invention provides a method of dispensing liquid droplets of the order of 30 $\mu$l or less in volume in a dispensing assembly using a pressurised delivery source feeding a metering valve body, the valve body comprising an elongate body member having an internal main bore, a base forming an apertured valve seat and a boss stopper in the main bore spaced-apart from the base; a valve boss comprising ferromagnetic material in the main bore, the cross-sectional area of which is sufficiently less than that of the main bore to allow the passage of liquid therebetween, a nozzle mounted on the base comprising an elongate needle-like member having a nozzle bore communicating between the valve seat and a dispensing tip and a variable power actuator for moving the valve boss in the bore between a closed position in engagement with the valve seat and an open position spaced-apart from the valve seat, the variable power actuator moving the valve boss by applying an electrical field to the valve boss, recording the position of the valve boss within the main bore of the body member throughout the dispensing cycle and using the information on the position of the valve boss within the bore to vary the force to be exerted on the valve boss between a highest force on engagement and disengagement of the valve boss with the valve seat and a lower force needed to keep the valve boss in spaced relationship with the valve seat to maintain the valve open. Needless to say, the lowest force will be zero at some instance when changing direction of the boss.

Then by opening the metering valve by exerting a disengaging force to separate the valve boss from the valve seat, once it has been separated, that is to say, on sensing of the opening of the metering valve, a lower opening force is exerted to remove the valve boss to a fully open position remote from the valve seat. Generally, this will be against, but does not have to be against, a valve stopper. It will largely depend on the volume of the droplet being dispensed and on the general configuration of the valve body. Then a lower force will be maintained to keep the valve open to retain the valve boss in a fully open position. Then, when it is required to close the valve, a closing force will be exerted on the valve boss to move the valve boss close to the valve seat. Then when the valve boss is sensed as being about to contact the valve seat, then a valve engaging force is exerted on the valve boss and this force must be such as to ensure that the valve boss does not bounce on the valve seat and then, on sensing that the valve boss is stationary, a lower closed maintaining or retaining force is exerted on the valve boss. Thus, overheating is largely prevented. Obviously, when there is a boss stopper, then additionally, when the valve boss is sensed as about to contact the valve stopper, there is exerted a variable stopper engaging force in the valve seat to cause the valve boss to attain zero boss velocity or essentially to stop. Then, again, once the valve boss is contacting a valve stopper, once it has stopped and is stationary, then a lower force is exerted on the valve boss.

Further, the invention provides methods of determining various characteristics of the liquid being dispensed. For example, it is possible to measure the volume of the droplet being dispensed by measuring the difference between the opening force and the closing force. The volume may be calculated from various formulae such as:

$$V_{disp}=U_1*Sg*t$$

and $$F_{mo}-F_{mc}=k*\eta*2*U_1,$$

$\eta$=viscosity of fluid.
k=constant dependent on boss and main bore dimensions.
$U_1$=flow velocity in the gap between the boss and the body member due to the delivery of liquid to the tip of the dispenser.
Sg=cross sectional area of gap between the valve boss and the main bore.
$F_{mo}$=opening magnetic force.
$F_{mc}$=closing magnetic force.
t=time during which the dispenser is open.
Alternatively, the volume may be calculated from:

$$V_{disp}=Q_{nozzle}*t$$

where
$Q_{nozzle}$ is flow rate through nozzle bore
t=time during which the dispenser is open
and $Q_{nozzle}=\pi*\delta P*r_n^4/(8*L_n*\eta)$
where
$\delta P$=pressure difference along nozzle from seat to tip
$r_n$=nozzle bore radius
$L_n$=nozzle length
$\pi$=3.1415.

Further, the invention provides a method of measuring the density of a liquid being dispensed by measuring the current required to move the boss at a constant relatively low velocity and the density is calculated from $$l*k_m=V_b*g*(P_b-P_l)$$

l=current in the actuating coil assembly
$k_m$=coefficient dependent on actuating coils
$V_b$=volume of boss
$P_b$=density of boss
$P_l$=density of liquid
g=acceleration due to gravity

BRIEF DESCRIPTION OF THE DRAWINGS

The invention will be more clearly understood from the following description of some embodiments thereof given by way of example only with reference to the accompanying drawings in which.

DETAILED DESCRIPTION OF THE PREFERRED EMBODIMENTS

Figure 1:
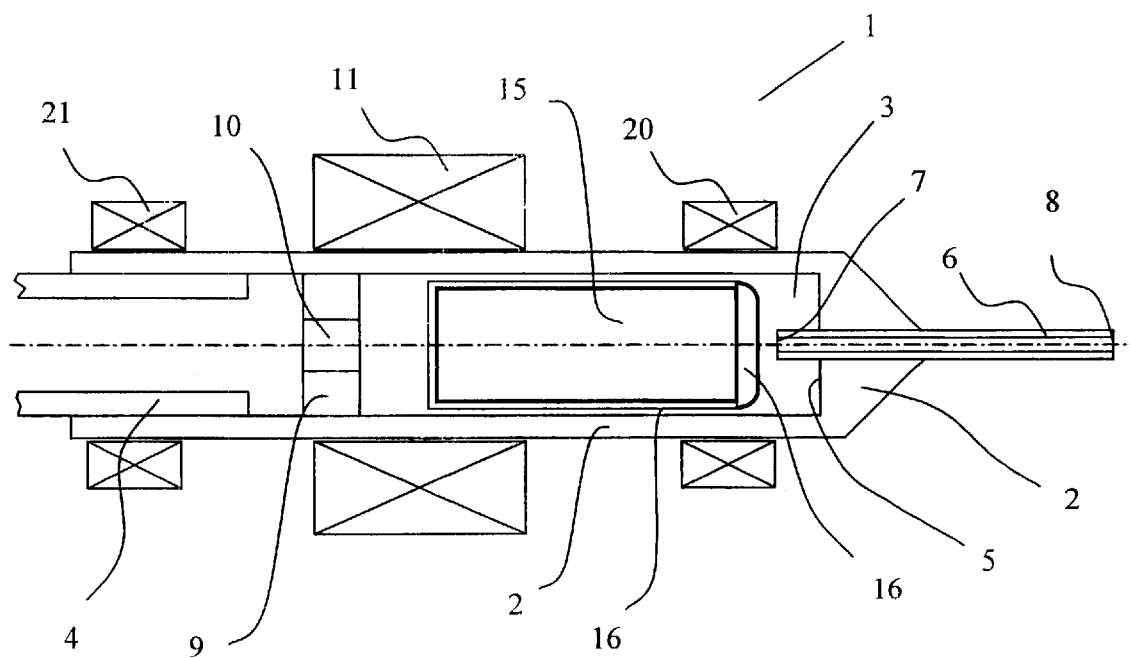
FIG. 1 is a side part sectional view, with sectional lines omitted, of a dispenser according to the invention.
Figure 2:
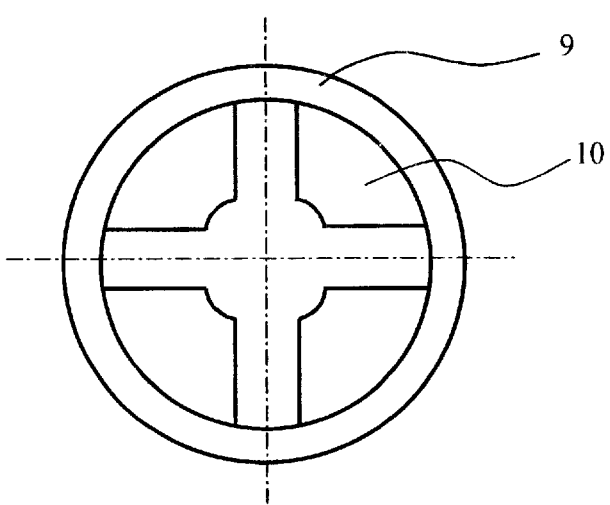
FIG. 2 is an end view of a stopper used in the dispenser of FIG. 1.

Referring to the drawings and initially to FIG. 1, there is illustrated a dispenser, indicated generally by the reference numeral 1 comprising a metering valve body 2 having a main bore 3 connected by a pipe 4 to a pressurised liquid delivery or vacuum source (not shown) forming, with a control circuit, a dispensing assembly. The body 2 comprises a base 5 in which is mounted a nozzle 6 projecting above the base 5 to form a valve seat 7 The nozzle 6 terminates in a dispensing tip 8. The main bore 3 mounts a valve boss stopper 9 having through holes 10 for the passage of liquid therethrough. An actuating coil assembly 11 is mounted on the exterior of the body 2 and surrounds it. In some of the FIGS. of this specification, not all of the actuating coil assembly is shown but only the coils forming part of the assembly. However, for simplicity, no distinction is made. Generally, power sources, being an obvious requirement, are not shown. A pair of sensing coils, namely, a front sensing coil 20 and a rear sensing coil 21 are mounted around and spaced-apart along the body 2 forming part of a valve boss detector. Within the main bore 3, there is mounted a valve boss 15 of a ferromagnetic material with hard magnetic properties covered by a soft polymer coating 16. All of these except for the sensing coils 20 and 21 have already been disclosed in co-pending U.S. and other patent applications.

Figure 3:
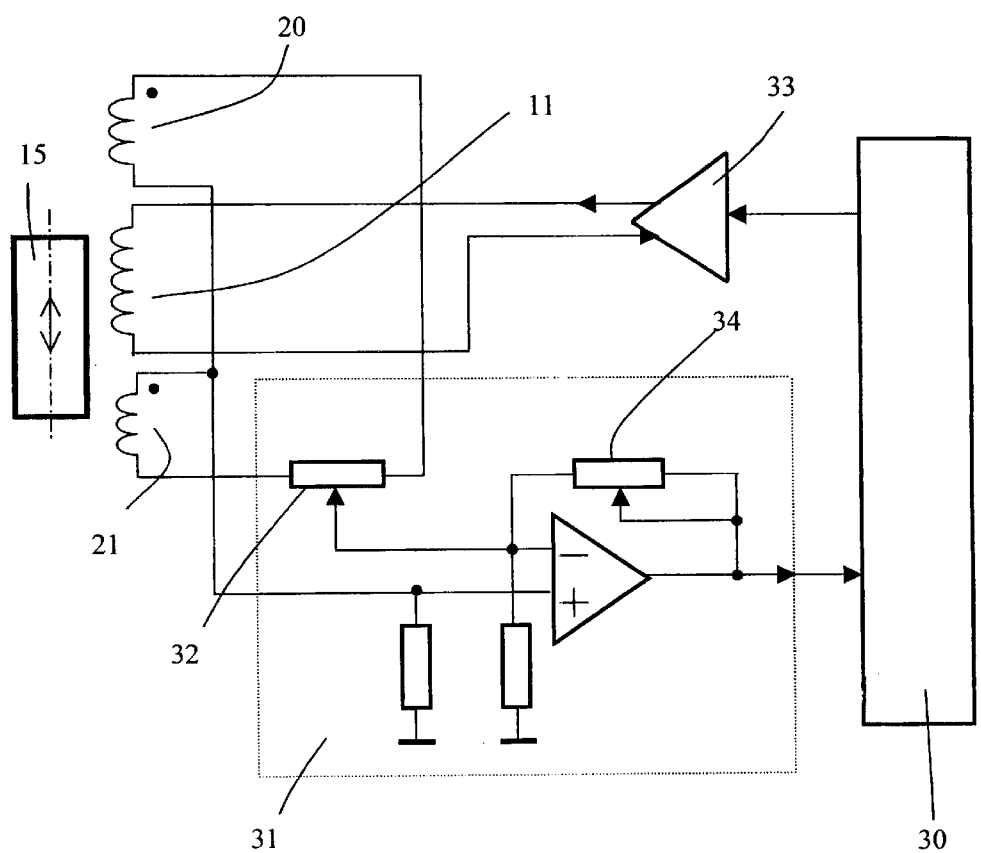
FIG. 3 is a schematic view of a control circuit used with the dispenser of FIG. 1.

Referring now to FIG. 3, there is illustrated in general form a control circuit forming the valve boss detector and control means of the dispensing assembly according to the present invention and the various parts already described are identified by the same reference numerals. There is provided a feedback controller 30 connected to a signal amplifier circuit 31 shown in the drawing by interrupted lines surrounding it which incorporates a compensation potentiometer 32. The feedback controller 30 is connected to a power amplifier 33 which feeds the actuating coil assembly 11. In use, the power amplifier 33 delivers power to the actuating coil assembly 11 which then in turn moves the valve boss 15. If the current through the actuating coil assembly 11 changes, it induces voltage in the sensing coils 20 and 21. This voltage is a result of the inductive coupling of the sensing coils 20 and 21 with the actuating coil assembly 11. Then, if the separations between each of the sensing coils 20 and 21 and the actuating coil assembly 11 are equal and if the sizes of the two sensing coils 20 and 21 are equal as well as the number of windings on the two coils 20 and 21, the voltage values induced in the coils 20 and 21 will be substantially equal. However, this takes no account of the valve boss 15. For example, in FIG. 1, the valve boss 15 is much closer to the sensing coil 20 than to the sensing coil 21. Therefore, movement of the valve boss 15 produces different voltages in the sensing coils 20 and 21. For any position of the valve boss 15, the difference between the voltages induced in the sensing coils 20 and 21 depends on the velocity of the valve boss 15 and this voltage difference is virtually proportional to the velocity of the valve boss 15. Thus, by integrating the difference between the voltages induced in the coils 20 and 21 over time, it is possible to calculate the actual position of the valve boss 15 at any given time provided that its initial position is known. For example, suppose the dispenser 1 was initially closed with the valve boss 15 on the valve seat 7. As the actuating coil assembly 11 starts moving the valve boss 15 away from the valve seat 7, the position of the boss 15 can be calculated at each subsequent moment of time. Therefore, the current through the actuating coil assembly 11 can be adjusted in such a way that the moment of closure of the dispenser is well timed.

As the position of the valve boss 15 is known with the use of the sensing coils 20 and 21, one can avoid negative effects such as bouncing of the boss at the moment of making contact with the valve seat 7. The bouncing results in additional uncontrollable openings of the dispenser as the boss makes a few oscillations coming in and out of contact with the valve seat before eventually coming to an equilibrium position. Another undesirable effect that can be avoided if the position of the valve boss 15 is known, is bouncing of the boss on the stopper 9. This bouncing also has a detrimental effect on the accuracy of the dispensing in particular for droplets of smaller volumes because as a result of the bouncing, the distance between the boss and the valve seat is not well defined. Therefore, at the moment when the current in the actuating coil assembly reverses to bring the boss back to the valve seat for the closure of the dispenser, the time required for the boss to reach the valve seat is similarly not well defined.

Figure 4:
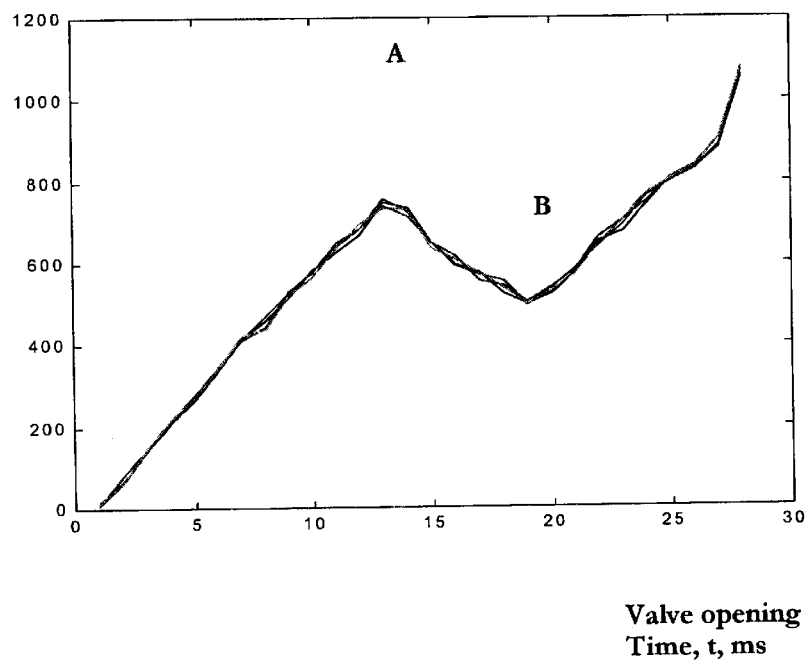
FIG. 4 is a graph of volume dispensed over time.

Referring to FIG. 4, there is illustrated the volume dispensed over valve opening time. The liquid dispensed in this experiment was water. The diameter of the nozzle bore was approximately 150 $\mu$m; the length of the nozzle was approximately 30 mm; and the pressure in the dispenser was approximately 2 bar. The dispenser operated with no feedback control. Up to the opening time of about 13 milliseconds, namely, to the point A, it can be seen that with the particular dispenser in question, the dependency is monotonous. The greater the opening time, the greater the volume dispensed. However, once the valve boss has reached the stopper, it bounces and moves back to the valve seat. Therefore, to return to the valve seat, it has to travel a shorter distance thus arriving to the valve seat earlier and as a result reducing the volume dispensed. Therefore, the dependency is no longer monotonous. The time required to reach the stopper depends on the shape of the boss, dimensions of the dispenser and the actuating coil. It also depends on the amplitude of the current supplied to the actuating coil and the viscosity of the liquid in the dispenser. In general, the greater the current, the sooner the boss reaches the stopper. The specific shape of the graph shown in FIG. 4 depends on the type of dispenser and the liquid dispensed. These results clearly demonstrate the advantage of using sensors of the boss position and/or velocity and/or acceleration as described above. By monitoring movement of the boss and by using a feedback, the accuracy of dispensing is improved.

By using the signal from the sensing coils 20 and 21, bouncing of the boss against the stopper and against the valve seat can be avoided as the current in the actuating coil assembly can be adjusted in such a way as to dampen the bouncing. Additional beneficial effect of the feedback is in the fact that the actuating coil assembly can be safely supplied with a higher value of the current at the moment when a large force is required to accelerate the boss. Such a large force is desirable at the moment of opening of the valve seat and also at the moment of closing the valve seat. Therefore, it may be desirable to drive current as large as possible through the actuating coil assembly to time accurately the moments of opening and closing of the valve seat. However, driving large current over extended periods of time may destroy the actuating coil assembly especially during the dispensing of large droplets and aspiration of liquid. Therefore, it may be desirable to reduce the current through the actuating coil assembly to a relatively small level when the boss reaches the stopper. This can be done readily if the position and/or velocity and/or acceleration of the boss are being continuously measured using the sensing coils. The moment when the boss reaches the stopper, the velocity is reduced considerably. It is important to appreciate that the timing required for the boss to travel between the stopper and the valve seat does not only depend on the current through the actuating coil assembly, shape and type of the boss but also on the viscosity of the liquid filling the dispenser. In general it is difficult to predict the position of the boss within the dispenser at every given moment of time on the basis of only current in the actuating coil assembly and calibration tables characterising the dispenser. Therefore, measurement of the position of the boss in real time is highly beneficial. As a result of the measurement, the current through the actuating coil assembly can be adjusted to achieve the desired movement pattern as a function of time resulting in turn in a more accurate control of time interval during which the valve is open.

The apparatus of FIG. 1 was then used to dispense with the feedback disabled and with the feedback enabled. Table 1 shows the results with feedback disabled and Table 2 with it enabled.

TABLE 1

| | | | | | | | | | | |
|---|---|---|---|---|---|---|---|---|---|---|
| 4187 | 4192 | 3345 | 4087 | 3943 | 4153 | 3914 | 3431 | 3907 | 337.3 | 8.63% |
| 3947 | 3897 | 4180 | 3998 | 3501 | 2907 | 3433 | 3520 | 3673 | 411.5 | 11.20% |
| 3496 | 3201 | 3633 | 3987 | 2984 | 3912 | 4428 | 3391 | 3629 | 466.0 | 12.84% |
| 4079 | 3886 | 3923 | 4692 | 3101 | 3234 | 3192 | 3478 | 3698 | 547.1 | 14.79% |
| 3641 | 3253 | 3541 | 3493 | 4074 | 3123 | 2956 | 4146 | 3528 | 424.4 | 12.03% |
| 3674 | 3945 | 3465 | 4245 | 3998 | 3620 | 3525 | 3599 | 3759 | 272.9 | 7.26% |
| 3981 | 4583 | 3392 | 3477 | 4134 | 2993 | 3432 | 3501 | 3687 | 507.3 | 13.76% |
| 3215 | 4372 | 3501 | 3651 | 3992 | 3489 | 3163 | 3451 | 3604 | 402.8 | 11.18% |
| 3504 | 3643 | 3238 | 4102 | 4013 | 4397 | 3982 | 3524 | 3800 | 383.7 | 10.10% |
| 3939 | 3970 | 4354 | 3416 | 3272 | 3972 | 3467 | 3329 | 3715 | 393.8 | 10.60% |
| 3927 | 3907 | 3365 | 3273 | 2874 | 3048 | 4632 | 3504 | 3566 | 568.2 | 15.93% |
| 3665 | 3936 | 3976 | 3516 | 3380 | 3503 | 4082 | 3951 | 3751 | 266.2 | 7.10% |
| 3351 | 3030 | 4228 | 4573 | 3965 | 3143 | 3416 | 3438 | 3643 | 549.7 | 15.09% |
| 4485 | 3602 | 3264 | 3987 | 3037 | 2768 | 3012 | 3503 | 3457 | 566.6 | 16.39% |
| 3993 | 4372 | 4726 | 3256 | 3021 | 3852 | 3359 | 3432 | 3751 | 590.2 | 15.73% |
| 3497 | 3732 | 3408 | 3936 | 3992 | 4376 | 3531 | 4056 | 3816 | 332.3 | 8.71% |
| 4281 | 3207 | 4385 | 3403 | 4075 | 4527 | 3134 | 3995 | 3876 | 550.7 | 14.21% |
| 3171 | 3548 | 3996 | 3203 | 4681 | 3401 | 3017 | 4207 | 3653 | 585.0 | 16.01% |
| 3882 | 3977 | 4261 | 3813 | 3291 | 4407 | 3215 | 3542 | 3799 | 428.8 | 11.29% |
| 3612 | 3997 | 3985 | 3527 | 3374 | 3232 | 3021 | 2894 | 3455 | 407.8 | 11.80% |
| 3202 | 3511 | 3984 | 4285 | 3942 | 3157 | 3967 | 3913 | 3745 | 407.1 | 10.87% |
| 4073 | 3394 | 3889 | 3711 | 3172 | 3021 | 4160 | 3198 | 3577 | 439.4 | 12.28% |
| 3145 | 3402 | 3532 | 4294 | 3596 | 3923 | 4674 | 3515 | 3760 | 506.0 | 13.46% |
| 4351 | 3987 | 4267 | 4117 | 3498 | 4189 | 3029 | 3230 | 3834 | 508.5 | 13.26% |
| 3762 | 3773 | 3827 | 3835 | 3621 | 3598 | 3573 | 3573 | 3695 | | |
| 390.0 | 403.6 | 422.0 | 420.2 | 476.0 | 549.7 | 530.5 | 317.6 | | 449.4 | |
| 10.37 | 10.70 | 11.03 | 10.96 | 13.14 | 15.28 | 14.85 | 8.89 | | | 12.16% |

Average value 3695 0.5 ul DMSO
Standard deviation 449.4
CV % 12.16

TABLE 2

| | | | | | | | | | | |
|---|---|---|---|---|---|---|---|---|---|---|
| 3962 | 3888 | 3906 | 3903 | 3851 | 385 | 3819 | 3763 | 3869 | 60.7 | 1.57% |
| 3706 | 3775 | 3762 | 3784 | 3702 | 367 | 3643 | 3620 | 3709 | 61.2 | 1.65% |
| 3807 | 3724 | 3684 | 3676 | 3711 | 370 | 3727 | 3691 | 3715 | 41.2 | 1.11% |
| 3853 | 3764 | 3769 | 3780 | 3744 | 377 | 3683 | 3640 | 3751 | 64.6 | 1.72% |
| 3790 | 3781 | 3746 | 3747 | 3732 | 369 | 3756 | 3646 | 3737 | 47 | 1.26% |
| 3785 | 3753 | 3764 | 3739 | 3704 | 365 | 3645 | 3699 | 3718 | 51.6 | 1.39% |
| 3765 | 3763 | 3730 | 3774 | 3711 | 370 | 3655 | 3700 | 3725 | 41.1 | 1.1% |
| 3671 | 3771 | 3773 | 3750 | 3704 | 378 | 3672 | 3652 | 3722 | 53.1 | 1.43% |
| 3735 | 3743 | 3749 | 3711 | 3700 | 369 | 3658 | 3640 | 3704 | 39.3 | 1.06% |
| 3738 | 3769 | 3707 | 3710 | 3735 | 372 | 3709 | 3578 | 3709 | 56.6 | 1.53% |
| 3728 | 3843 | 3691 | 3670 | 3706 | 373 | 3732 | 3583 | 3711 | 72.9 | 1.96% |
| 3749 | 3762 | 3700 | 3697 | 3680 | 374 | 3660 | 3655 | 3706 | 41 | 1.11% |
| 3750 | 3729 | 3729 | 3698 | 3704 | 362 | 3663 | 3613 | 3689 | 50.4 | 1.37% |
| 3750 | 3742 | 3696 | 3739 | 3737 | 366 | 3635 | 3593 | 3694 | 58.6 | 1.59% |
| 3753 | 3750 | 3729 | 3687 | 3734 | 365 | 3664 | 3598 | 3697 | 54.7 | 1.48% |
| 3801 | 3787 | 3759 | 3735 | 3706 | 374 | 3642 | 3666 | 3730 | 55.8 | 1.5% |
| 3821 | 3786 | 3804 | 3765 | 3786 | 371 | 3720 | 3626 | 3753 | 63.6 | 1.69% |
| 3819 | 3746 | 3790 | 3715 | 3780 | 363 | 3631 | 3693 | 3726 | 71 | 1.91% |
| 3779 | 3826 | 3869 | 3702 | 3748 | 364 | 3631 | 3743 | 3742 | 83.4 | 2.23% |
| 3731 | 3738 | 3714 | 3692 | 3698 | 368 | 3662 | 3730 | 3706 | 26.9 | 0.73% |
| 3753 | 3751 | 3746 | 3717 | 3687 | 363 | 3714 | 3645 | 3706 | 45.9 | 1.24% |
| 3842 | 3765 | 3816 | 3760 | 3694 | 365 | 3660 | 3687 | 3735 | 71.4 | 1.91% |
| 3779 | 3751 | 3750 | 3735 | 3734 | 374 | 3710 | 3707 | 3739 | 23.3 | 0.62% |
| 3869 | 3834 | 3889 | 3814 | 3783 | 384 | 3828 | 3690 | 3819 | 61.5 | 1.61% |
| 3781 | 3773 | 3761 | 3738 | 3728 | 370 | 3688 | 3661 | 3730 | | |
| 60.9 | 39.3 | 59.94 | 51 | 39.5 | 62. | 54.6 | 50.5 | | 65.4 | |
| 1.61 | 1.04 | 1.594 | 1.37 | 1.06 | 1. | 1.48 | 1.38 | | | 1.75% |

Average value 3730 0.5 ul DMSO
Standard deviation 65.39
CV % 1.75%

Test conditions were as follows.

The pressure in the pressure/vacuum pipe was 2 Bar. The boss was a cylinder with the diameter of 1.7 mm and length of 7 mm. The travel length of the boss between the fully open and fully closed positions of the dispenser was 1 mm. The actuating coil assembly consisted of a single coil having 150 turns, its internal diameter was 4.3 mm, length 5 mm, outside diameter 8 mm. The two sensing coils are identical, their internal diameter is 4.3 mm, outside diameter is 7 mm and length is 4 mm. Each of the sensing coils has 25 turns The dispensations were performed in a 384 format well plate. The liquid dispensed was concentrated dimethyl siloxane (DMSO). This liquid is commonly used in life sciences and pharmaceutical industry. A fluorescent marker, namely, rhodamin was added to the DMSO in the concentration of 20 micromole/liter. After dispensing of 0.5 microliter of DMSO with rhodamin into each well plate 8 microliter of distilled water was added into each plate in accordance with the standard procedure for measurement using well plates and optical readers. The reason for adding water is to ensure that the volume of the liquid in each well plate takes a significant fraction of the well plate. Otherwise, the accuracy of measurements would be compromised. The volume readout was performed using an optical reader, in this case Spectra Fluor Plus from Tecan. The first eight columns in each table indicate intensity of the optical fluorescence signal as measured by the reader. This intensity is approximately proportional to the volume of DMSO in each well. Each of the first eight columns consists of 24 rows representing readings for 24 separate wells. The ninth column represents the average for each row and the 25$^{th}$ row represents the average for each column. The 27$^{th}$ row represents the sigma error for each column. The 11$^{th}$ column represents the sigma error for each row. The overall sigma error in the table 1 is 12.16% and the optical signal averaged over the whole table is 3695. In Table 2, these values are respectively 1,75% and 3730.

Another beneficial effect that can be achieved by using the signal from the sensing coils is on-line measurement of the properties of liquid dispensed such as, for example, its viscosity. As the force acting on the boss moving within a liquid depends on the viscosity of the liquid, and as one can measure the force and velocity simultaneously using the value of the current in the actuating coil assembly and the signal from the sensing coil respectively, the viscosity can be calculated. In a similar way, density of the liquid, $\rho_l$, can be measured through the detection of the Archimedes force acting on the boss. To explain the method of measurement of these values, we need to consider forces acting on the boss in detail. During movement of the boss within the dispenser, the total force Ft acting on the boss is described within an approximation as follows:

$$F_t = F_m - k*\eta*(U-V) + F_a + m_b*g + F_f \tag{1}$$

where $F_m$ is the magnetic force from the actuating coil assembly, $\eta$ is the viscosity of liquid, k is a constant determined by the shape of the boss and separation between the walls of the boss and the inner walls of the dispenser, U is the flow velocity of the liquid inside the body of the dispenser relative to the walls of the dispenser, V is the velocity of the boss relative to the walls of the dispenser, $F_a$ is the Archimedes force resulting from the liquid in the dispenser, $m_b$ is the mass of the boss, and g is acceleration due to gravity, $F_f$ is a frictional force between the boss and the walls of the body member when they come in contact with each other. The second term in the right part of the equation (1): $k*\eta*(U-V)$ defines the viscous force acting on the boss. The viscous force is proportional to the velocity of the boss relative to the velocity of the flow of liquid: U−V. The next term $m_b*g$ defines the gravity force acting on the boss. On the basis of the fundamental laws of physics one can state that if the boss moves with a constant velocity then the total force $F_t$ is equal to zero.

It can be advantageous to perform the detection of viscosity $\eta$ and density $\rho_l$ of the liquid at different stages of the boss movement. The viscosity could be easier measured when the boss moves with a relatively high velocity and the viscous force is significant by comparison with other forces in equation (1). In this case we can neglect the forces $F_a$, $m_b*g$ and $F_f$. We then get the equation $$F_m = k*\eta*(U-V) \tag{2}$$

The flow velocity U of liquid in the body of dispenser is not necessarily much smaller than velocity V of the boss. There are two significant contributions to the velocity U. Therefore, within an approximation, U can be defined as: $U=U_1+U_2$ (or $U=U_2-U_1$ depending on the direction of flow as explained below). Here $U_1$ is the contribution due to the flow of liquid passing the boss to the tip and to the outside of the dispenser. The value of $U_1$ depends on the diameters of the nozzle bore and body member of the dispenser, length of the nozzle and pressure value in the pressure/vacuum pipe. In a typical embodiment with the boss of 2 mm in diameter and a gap of 0.2 mm between the boss and the walls of the body member, pressure of 1 to 3 Bar, nozzle bore of 150 μm, and nozzle length of some 30 mm, the value of $U_1$ is in the range of $10^{-2}$ to $2*10^{-1}$ m/sec. This is relatively small by comparison with the value of V that can typically be in the range of up to 1 m/sec. The contribution $U_2$ is due to the flow of liquid that is being displaced within the dispenser by the moving boss. To understand better the contribution $U_2$ it is advantageous to imagine for a moment that the nozzle of the dispenser is blocked and therefore there is no flow of liquid to the outside of the dispenser. In this case $U_1$ is equal to zero. One can appreciate that as the boss moves away from the valve seat, there will be a flow of liquid in the opposite direction to fill the vacuum gap created by displacement of the boss. This flow will result in the velocity $U_2$ that can be calculated from the conservation of volume:

$$U_2*S_g = V*S_b$$

Here $S_g$ is the cross sectional area of the gap within the dispenser between the boss and the inner walls of the body of the dispenser, $S_b$ is the cross sectional area of the boss. In a typical embodiment, the value of the $S_g$ ($5*10^{-7}$ to $10^{-5}$ m$^2$) is smaller than the value of $S_b$ ($10^{31\,6}$ to $5*10^{-5}$ m$^2$). Therefore the value of $U_2$ is typically greater than that of V. As the boss moves away from the valve seat all the three contributions add together and the relative velocity of the liquid relative to the boss is $V+U_1+U_2$ giving the viscous force:

$$F_{m1} = k*\eta*(U_1+U_2+V) = k*\eta*(V*S_b/S_g+U_1+V).$$

As $U_1$ is often small by comparison with V, this formula can be simplified to:

$$F_m = k*\eta*V*(S_b/S_g+1).$$

As the boss moves away from the valve seat, all the three contributions: V, $U_1$ and $U_2$, must be added together as the contributions $U_1$ and $U_2$ result in the movement of liquid in the direction opposite to the movement of the boss. As the boss moves towards the valve seat, the relative velocity of the liquid is $U_2-U_1$ resulting in the viscous force:

$$F_{m2}=k*\eta*(U_2-U_1+V)=k*\eta*(V*S_b/S_g-U_1+V).$$

As $U_1$ is often small by comparison with V, this formula can again be simplified to:

$$F_m=k*\eta*V(S_b/S_g+1). \quad (3)$$

On the other hand, $F_m$ is proportional to the current I in the actuating coil assembly:

$$F_m=k_m*I,$$

where $k_m$ is a coefficient defining mainly the shape and size of the actuating coils and the boss and also the material of the boss. As the current I is known, the value of $\eta$ can be obtained from equation (3). It is clear that this method requires calibration of the dispenser if a numerical value of $\eta$ is required, not just a value in arbitrary units. One of the methods of calibrating the dispenser consists of filling it with a liquid with a known value of viscosity $\eta$, measuring the current I required to move the boss with a constant velocity V of a significant value when the conditions described above are fulfilled, and measuring the value of $k/k_m$.

The values of viscous force acting on the boss during its movement away and towards the valve seat, are different. They are equal respectively to:

$$k*\eta*(V*S_b/S_g+U_1+V) \text{ and } k*\eta*(V*S_b/S_g-U_1+V).$$

Therefore, by measuring the difference between the forces exerted on the boss by the actuating coil assembly $F_{m1}$ and $F_{m2}$, equal to these viscous forces and by taking the difference between them, one can measure velocity $U_1$ directly:

$$F_{m1}-F_{m2}=k*\eta*2*U_1$$

Therefore, the simplest algorithm for measurement of velocity $U_1$ is to move the boss from the valve seat and towards it with a constant velocity, and measure the difference between the currents in the actuating coil assembly during these two stages of movement. It may be advantageous to calibrate the dispenser, i.e. to measure the value of $U_1$ independently in order to establish the value of $k*\eta$. Using the formulas for the forces $F_{m1}$ and $F_{m2}$ one can readily devise numerous other algorithms for measurement of the value of $U_1$. One can appreciate that this algorithm for measurement of velocity $U_1$ enables a direct measurement of the volume of the liquid dispensed. Indeed, the volume dispensed $V_{disp}$ is equal to the $U_1*S_g*t$, where t is the time of the opening of the dispenser.

The volume dispensed can also be measured using a different method. Once the viscosity of the liquid is measured, and the opening time of the dispenser is known, the volume dispensed is $V_{disp}=Q_{nozzle}*t$, where $Q_{nozzle}$ is the flow rate through the nozzle bore and t is the time during which the dispenser is open. As the nozzle produces the main contribution to the flow resistance due to its small cross section and large length, the flow rate is determined mainly by the dimensions of the nozzle. Within an approximation, the value of Q can be calculated as:

$$Q_{nozzle}=\pi*\delta P*r_n^4/(8*L_{nozzle}*\eta).$$

Here $\delta P$ is the pressure difference along the nozzle between the valve seat and the end of the tip, $L_{nozzle}$ is the length of the nozzle, $r_n$ is the radius of the nozzle bore, $\pi$ is the constant equal to approximately 3.1415.

Measurement of the density of the liquid in the dispenser can be also performed according to, for example, the method described below. It is better to measure the density when the velocity is low and the relative value of the Archimedes force increases in comparison with the viscous force. In this case the terms $k*\eta*(U-V)$ and $F_f$ are small and therefore $$F_m=F_a+m_b*g \quad (4)$$

$F_a=-v_b*g*\rho_l$, where $V_b$ is the volume of the boss, and $\rho_l$ is the density of liquid in the dispenser. The mass of the boss is also proportional to its volume: $m_b=v_b*\rho_b$, where $\rho_b$ is the density of the boss. Therefore, $F_m=v_b*g*(\rho_b-\rho_l)$. On the other hand, $F_m$ is proportional to the current I through the actuating coil: $F_m=I*km$, where $k_m$ is a coefficient defined mainly by the shape and size of the actuating coils and of the boss and also the material of the boss. Therefore, by measuring current I required to move the boss with a constant low velocity up or down, one can determine the value of $\rho_l$ as all the other values involved in the equation:

$$I*k_m=v_b*g*(\rho_b-\rho_l), \quad (5)$$

are known or can be measured. It can be advantageous to calibrate the dispenser with a liquid having a known density $\rho_l$. This allows measuring the value of $v_b*g/k_m$ that can then be used to measure densities of unknown liquids.

Another benefit that can be achieved by using the signal from the sensing coils is the ability to detect the moment when the dispenser runs out of liquid. The detection is based on the fact that the viscous force acting on the boss will change as the dispenser runs out of liquid. More generally this can be expressed as a change in the movement pattern of the boss that is monitored by using the sensing coils. In a similar manner the filling of the dispenser with liquid during aspiration could be confirmed enabling detection of a malfunction caused by, for example, blockage of the nozzle or by attempt of aspirating from an empty well.

The same approach to the measurements of the viscosity of the liquid, its density and flow velocity can be applied to dispensers in which sensing of the boss position and/or velocity and/or acceleration is achieved by means of other sensors described in detail in the embodiments below.

The above discussion related to measurement of the difference between the voltages induced in the sensing coils 20 and 21, one could apply the same consideration to an arrangement in which the sum of the two voltages is measured, not the difference. This would only require turning one of the two sensing coils by 180 degrees perpendicular to its axis. In this case taking the sum of the voltages induced in the two coils would compensate for the electromotive force induced by a changing current in the actuating coil.

Figure 5:
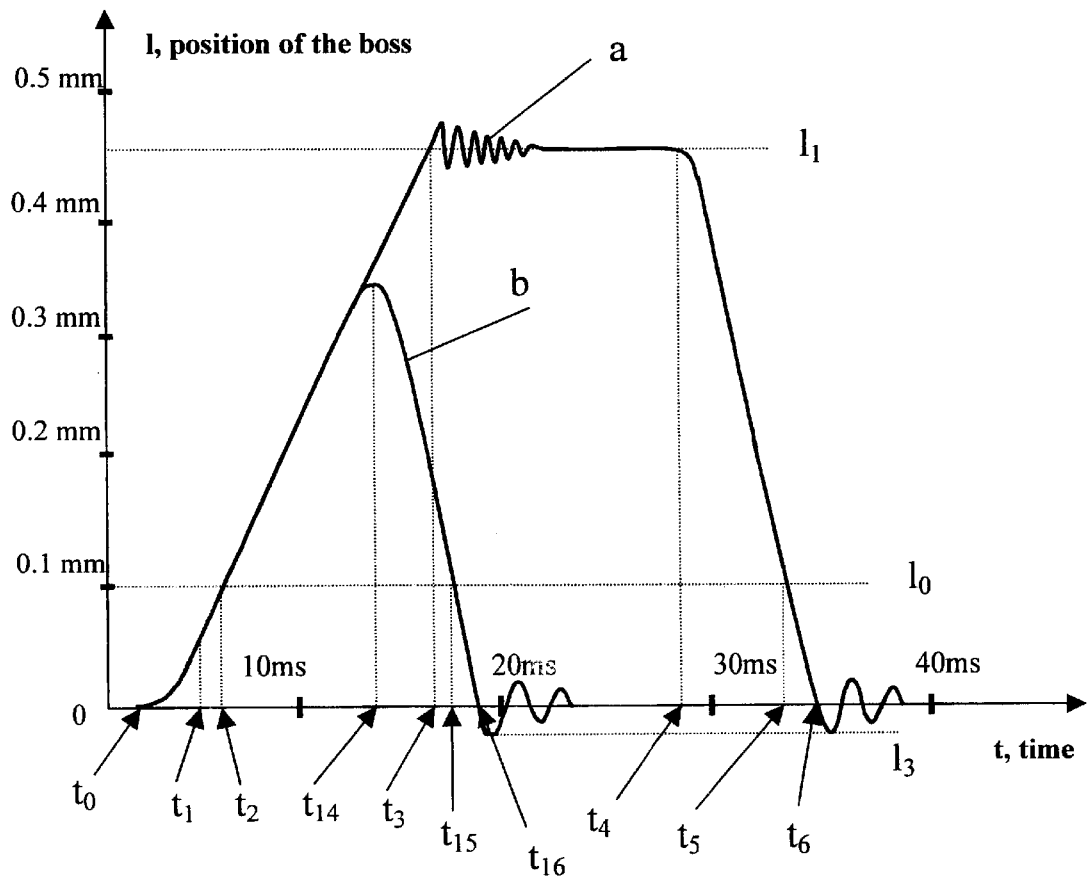
FIG. 5 shows typical boss movement over time.

Referring now to FIG. 5, there is illustrated a graph of a typical pattern of boss movement showing the position of the boss as a function of time. At the moment $t_o$, the boss moves under a disengaging force and the dispenser valve starts to open. At the moment $t_1$ the boss' velocity reaches the required value and then the boss continues moving with a constant velocity. This continues through $t_1$ to $t_2$ when the opening of the metering valve is sensed. By then the boss has travelled the distance $l_0$. The position $l_0$ at which the seal is broken is mainly determined by the compressibility of the soft coating on the boss and shape of the valve seat. The boss then moves with a constant velocity whose value is determined by the circuit of FIG. 3. At the moment $t_3$ the boss makes contact with the stopper. The time interval between the instants $t_3$ and $t_0$ is known or it can be measured in real time as will be described in more detail below. It is dependent on the dimensions of the dispenser and most importantly on the length that the boss can travel between the valve seat and the stopper. If the velocity of the boss is known, and the dimensions of the dispenser are also known, this time is well defined. Therefore, the moment $t_3$ can be introduced into a suitable control algorithm. At the moment $t_3$ or close to it, the controller switches off the regime of the velocity control of the boss and switches on the regime of defined force acting on the boss so that the boss presses on the stopper with a certain small force keeping it in this well-defined position. As the boss comes into contact with the stopper, it may bounce back as seen in FIG. 5 and result in an oscillation just after the time $t_3$. After a short time this oscillation will dissipate. In some embodiments, the oscillation can be damped faster by changing the value of the regulated velocity to zero for a short duration of time of some few ms. After the damping phase, the controller is switched to the regime of the constant force, namely, a valve open retaining force pressing the boss against the stopper. To prevent the danger of the burnout of the actuating coil assembly it is advantageous to limit the current through the actuating coil and not to use excessive force acting on the boss. The boss stays essentially pressed against the stopper until the moment $t_4$ at which the controller is again switched into the mode of velocity control. The boss is accelerated immediately after the moment $t_4$ and then moves back to follow the pre-calculated velocity profile. In FIG. 5 this velocity profile is a movement with a constant velocity that is a convenient choice due to its simplicity. Clearly, other patterns of movement can be defined. At the moment $t_5$ the soft coating on the boss comes into contact with the valve seat and forms the seal. At this moment the valve is closed again. The movement of the boss still continues in the same direction due to the compressibility of the coating on the boss and its inertia. At the moment $t_6$ or close to it, the controller is again switched from the velocity control mode into the force mode. It may be advantageous to set the value of the regulated velocity to zero straight after the moment $t_6$ for a short duration of time. This will reduce the amplitude of the bouncing of the boss on the valve seat. Due to its inertia, the boss will be pressed harder into the valve seat. The boss will be normally pressed so as to compress and thus to reach the negative $l_3$ position as shown for a short time after the moment $t_6$. However, if the final value of the force acting on the boss is the same as at the initial moment, $t_o$, the position of the boss after the completion of the oscillations/bouncing on the valve seat will be same as at the initial moment of time $t_0$. The oscillation/bouncing of the boss with small amplitude just after the moment $t_6$ will not result in any additional liquid dispensing. This is because these oscillations still occur on the fully closed valve seat. If the amplitude of the bouncing/oscillations exceeds the value of $l_0$, then indeed additional uncontrollable opening of the valve takes place and the accuracy of the dispensing is compromised. The volume dispensed is determined within a reasonable accuracy by the time interval between the instants $t_5$ and $t_2$.

For dispensing of droplets of smaller volumes, the time difference between the instants $t_5$ and $t_2$ is reduced. In this case the boss may not reach the position of the stopper $l_1$ at all. This is shown in FIG. 5 by the curve b. The moments $t_{14}$, $t_{15}$, $t_{16}$ have the same meaning as the moments $t_4$, $t_5$, $t_6$ respectively.

It has been found that in most situations where the diameter of the magnetic boss is some 1.5 to 2 mm and its length is 5 to 7 mm, a damping time of 0.5 to 3 millisecond is appropriate. A significantly shorter time may not fully damp out the velocity and kinetic energy of the boss and a significantly longer damping time is an unnecessary increase in the dispensing time. This time is clearly dependent on the velocity of the boss. If the velocity increases significantly, this time may need to be increased. The values of 0.5 to 1 millisecond correspond to a velocity of up to some 0.5 to 1 m/sec. The boss will bounce on the valve seat with the frequency of some 0.1 to 10 kHz. This frequency depends primarily on the shape of the valve seat, mass of the boss, thickness and type of the soft polymer coating on the boss.

Essentially, therefore, what happens in accordance with the invention is that the position of the valve boss within the main bore of the body member is recorded throughout the dispensing cycle and using the information on the position of the valve boss within the bore to vary the force to be exerted on the valve boss between a highest force needed to accelerate the valve boss during the initial moments of dispenser's opening and closing stages, that is to say, on disengagement and engagement of boss and valve seat and a lowest force needed to keep the valve boss in spaced relationship with the valve seat to maintain the valve open. Then, various steps are carried out sequentially of opening the metering valve by exerting a disengaging force on the valve boss to separate the valve boss from the valve seat. Then when the opening of the metering valve is sensed, a controlled opening force which is much smaller is used to remove the valve boss to a position fully remote from the valve seat. This will be done preferably at a constant velocity. Then, the valve is maintained in the open position by exerting a maintaining force on the valve boss to retain the valve boss in the fully open position. Then, this force is reversed and a closing force is exerted on the valve boss to move the valve boss close to the valve seat. Then, on sensing the valve boss is about to contact the valve seat, a valve seat engaging force is exerted on the valve boss and on sensing the valve boss is stationary, then a valve closed maintaining force is exerted on the valve boss.

Figure 6:
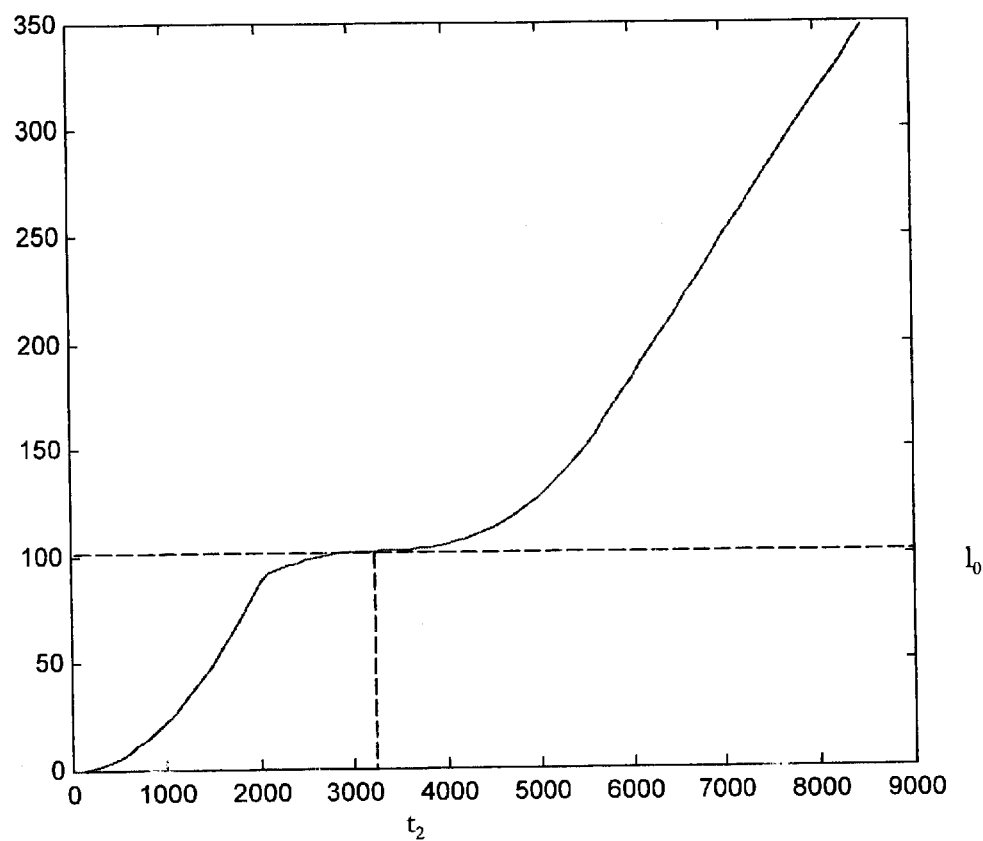
FIG. 6 illustrates the separation of the valve boss from the valve seat.

FIG. 6 illustrates the actual separation of the valve boss from the valve seat which is not instantaneous as shown at the time $t_2$ in FIG. 5 but in fact there is a slight lag with the movement of the boss impeded until the boss fully separates from the valve seat. This lag is due to sticking of the boss to the valve seat. The results are presented for the movement algorithm whereby a constant force is applied to the boss around the time $t_2$. It is clear that the specific values of time along the X-axis of the graph depend on the compressibility of the valve seal.

Figure 7:
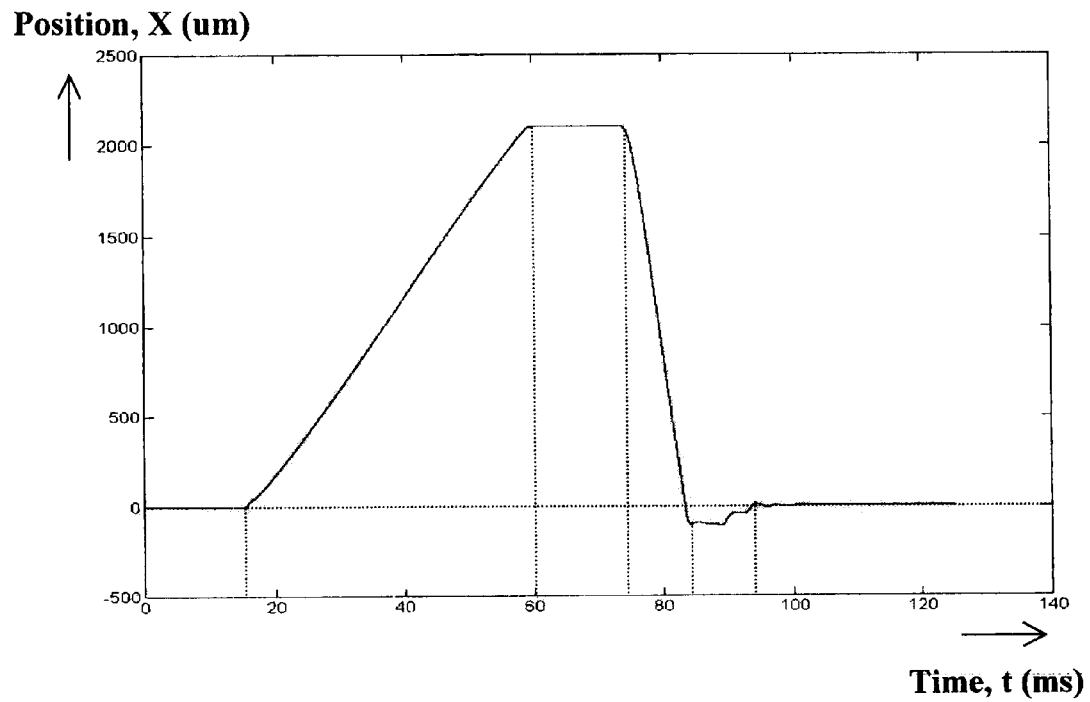
FIG. 7 shows the boss position over time.
Figure 8:
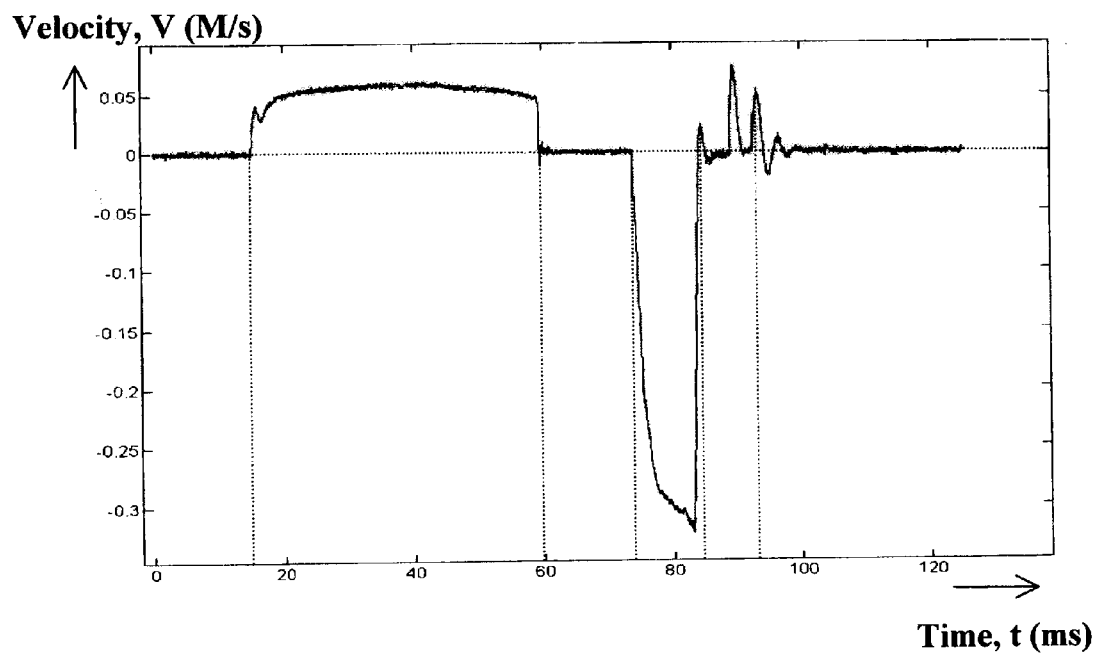
FIG. 8 illustrates valve boss speed over time.

FIGS. 7 and 8 show firstly the boss position against time and the boss speed against time respectively. In each case, there is a droplet of 10 $\mu$l of water dispensed under the conditions described above.

Figure 9:
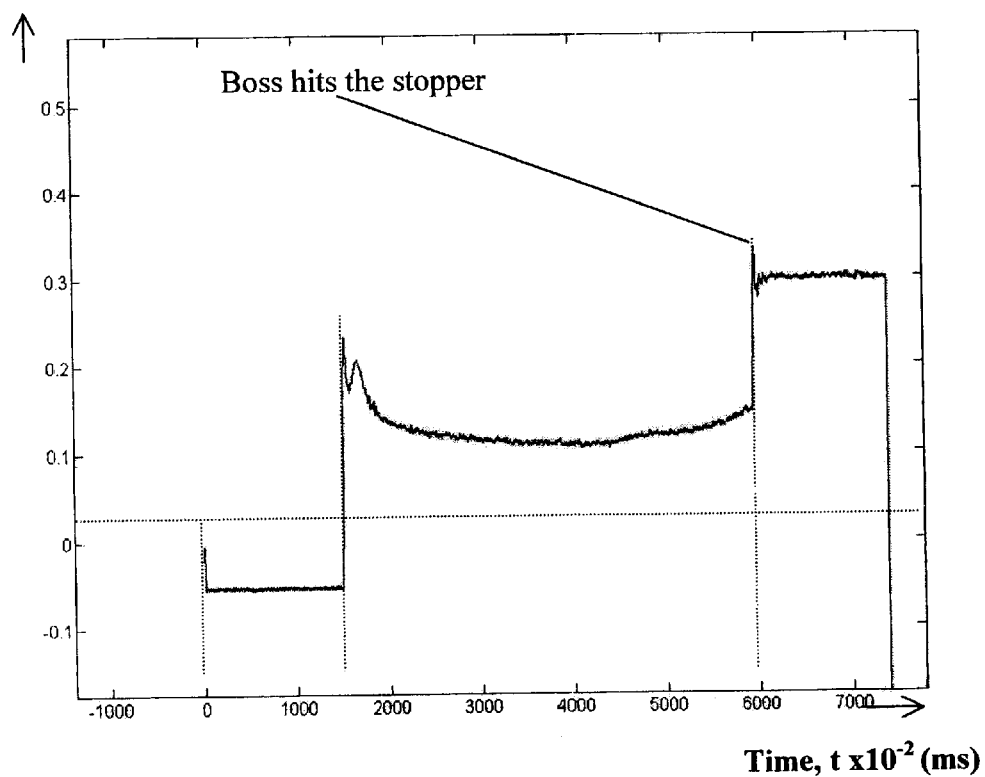
FIG. 9 illustrates the force exerted on the valve boss over time.

FIG. 9 illustrates the value of the force from the actuating coil assembly exerted on the boss during its movement described by FIGS. 7 and 8.

Figure 10:
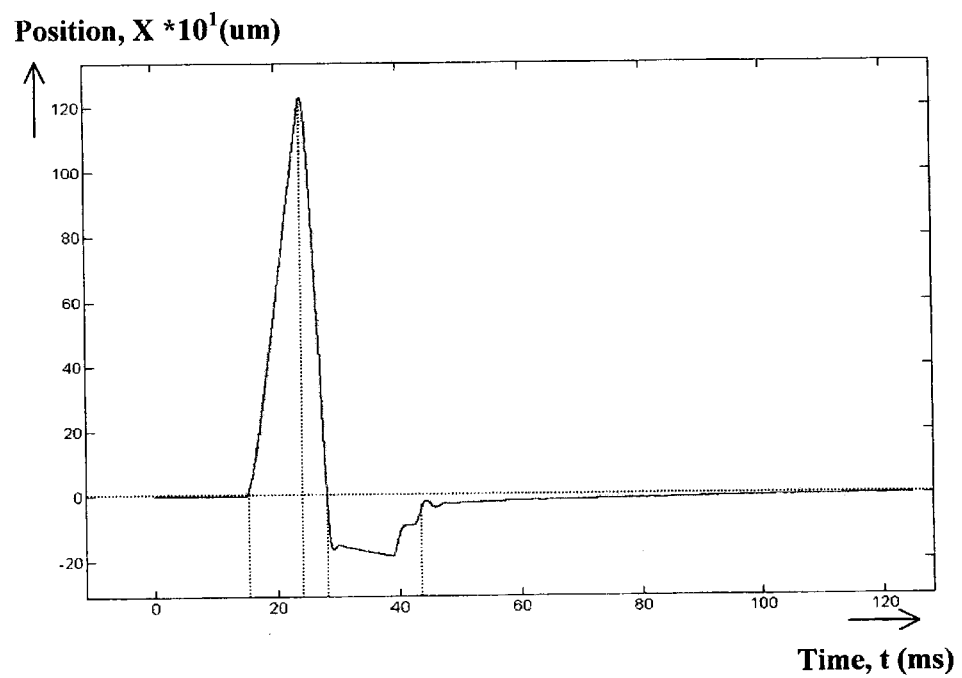
FIG. 10 shows the position of the valve boss over time for dispensing a different volume of liquid than that illustrated in FIG. 7.
Figure 11:
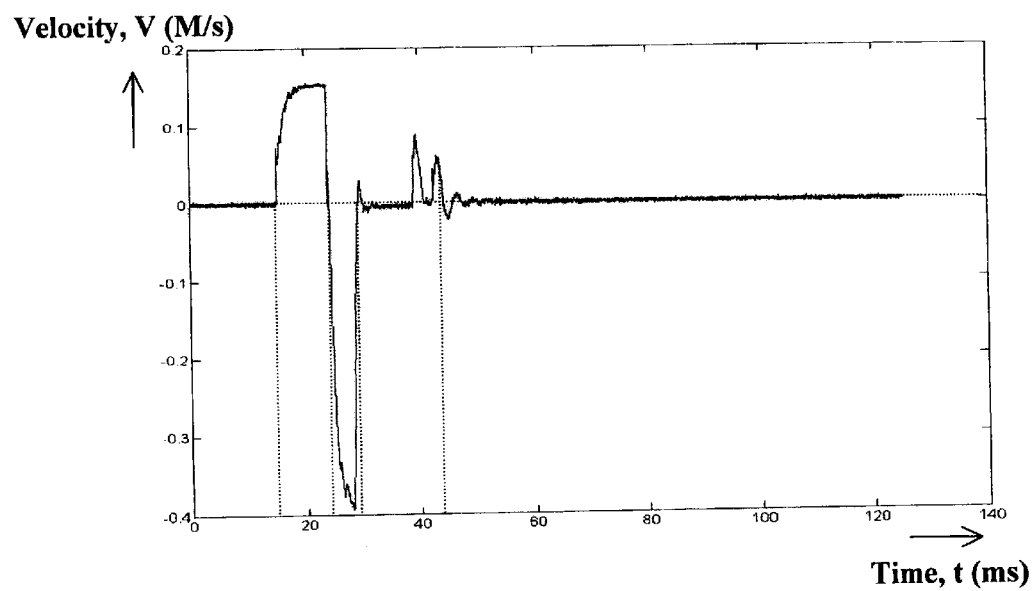
FIG. 11 illustrates boss speed over time for dispensing a volume of liquid different to that illustrated in FIG. 8.

FIGS. 10 and 11 show respectively identical situations as illustrated in FIGS. 7 and 8 except that now 1 $\mu$l of water is dispensed.

In a typical embodiment, the valve boss is a cylinder with the length of some 5 to 8 mm and diameter of 1.5 to 2.0 mm although many other dimensions well outside this range could also be practical. The soft coating on the boss is of a silicon rubber with the thickness of some 2 mm or 0.1 mm or even smaller. The internal diameter of the body member is 2 to 3 mm depending on the diameter of the boss and the thickness of the coating on the cylindrical side of the boss. The boss is made of SmCo magnet axially magnetised. The nozzle is a stainless steel capillary with the internal diameter of some 0.15 mm. The typical travel range of the boss is limited by the stopper on one side and the valve seat on the other and it is about 0.5 to 3 mm. The actuating coil has an internal diameter of 4.3 mm and consists of 150 windings. The sensing coil has an internal diameter of 4.3 mm and consists of 25 windings. The outside diameter of all the coils is about 8 mm. Separation between the sensing and the actuating coils is about 1 to 3 mm. The excess pressure in the pressure/vacuum pipe is about 1 to 4 Bar. The required excess pressure depends to some extent on the viscosity of the liquid dispensed. When dispensing liquids of higher viscosity such as concentrated glycerine or dimethyl siloxane (DMSO), it could be advantageous to increase the pressure in the pressure/vacuum pipe. This reduces the dispensing time and makes separation of the drop from the tip more reliable.

Thickness of soft coating on the boss depends on the smoothness and shape of the valve seat and elasticity of the coating. We have found that silicon adhesive (for example, type Q3-6611 from Dow Corning) with the thickness of 200 to 800 $\mu$m works well for a typical valve seat formed by the polished edge of a steel capillary with an internal diameter of some 50 to 150 $\mu$m and an external diameter of some 200 to 500 $\mu$m. Many other soft polymer materials are equally appropriate for coating the boss.

Many circuits are described in this specification, however, they are simply typical circuits which anyone skilled in the art would devise. Indeed, as more and different electrical and electronic components and circuits are devised, they could change radically in format and arrangement but not in functionality. Most of the circuits illustrate the circuit for the valve boss detector, the controller and portion in effect of the variable power output valve boss actuator, hereinafter often referred to as the circuit of the controller.

In this specification, the term "ferromagnetic material" is used to cover all magnetic materials such as, for example, ferrite materials which are sometimes distinguished from ferromagnetic materials. However, in this specification, no such distinction is made. Thus, the term "ferromagnetic material" has to be given the widest possible interpretation. The nozzle is preferably made of a hydrophobic material, at least the dispensing tip thereof could be so as to ensure efficient separation of the droplet from the dispensing tip.

Figure 12:
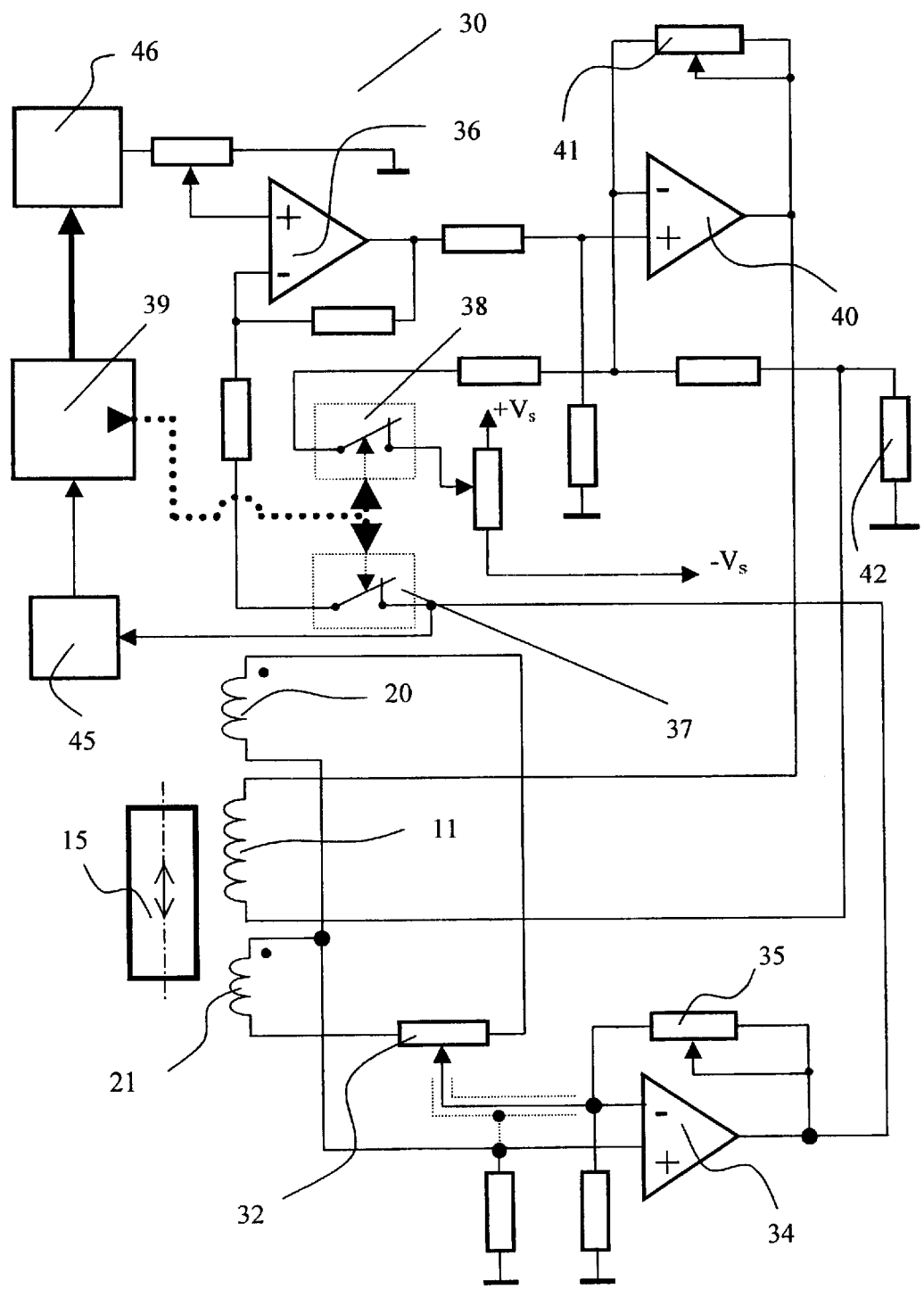
FIG. 12 is a more detailed schematic view of a control circuit for operating the dispenser of FIG. 1.

FIG. 12 shows in more detail schematically a circuit, indicated generally by the reference numeral 30, for measurement of voltage difference between the sensing coils 20 and 21 and controlling the current through the actuating coil assembly 11. The two signals are compared on a compensation potentiometer 32. A velocity sensing operational amplifier 34 amplifies the difference between the voltage signals induced in the sensing coils 20 and 21. The amplification gain is determined by a feedback gain resistor 35. The output from the velocity sensing operational amplifier 34 is connected to one of the inputs of a feedback operational amplifier 36 through a switch 37. The switch 37 and a further switch 38 are controlled by a Digital Signal Processor (DSP) 39. The output from the feedback operational amplifier 36 controls current through the actuating coil assembly 11. In the circuit shown in FIG. 12 this is done not directly but through an optional sub-circuit consisting of a power operational amplifier 40, gain resistor 41 and resistor 42. This sub-circuit operates as an additional fast feedback controlling the voltage applied to the actuating coil assembly 11. The purpose of this feedback is to increase considerably the value of the voltage applied to the actuating coil assembly 11 at the initial moments of opening and closing of the dispenser when the boss is beginning to move away from or towards the valve seat. As the velocity of the boss increases, the voltage applied to the actuating coil assembly decreases to protect them from burnout. This sub-circuit therefore helps to accelerate the boss faster at the start of the movement of the boss and as a result improves the accuracy of the timing of the opening and closing of the valve seat and thus the accuracy of the dispensing.

If the switch 37 is closed, and if the output of the DSP 39 supplies the profile of the desired velocity of the boss as a function of time, the circuit operates as an analogue feedback ensuring that the actual velocity of the boss is equal to the desired velocity. For example, if the actual velocity is smaller than the desired one, the feedback operational amplifier 36 will supply an increased current through the actuating coil assembly 11 and vice versa. The signal proportional to the velocity of the boss is also supplied into the DSP 39 through an Analogue-to-Digital Converter (ADC) 45. In this embodiment this is done so that the processor would also be able to receive information about actual velocity of the boss in real time for additional monitoring.

The circuit contains an optional switch 38. Switches 37 and 38 are closed and opened at the same instant. The purpose of the switch 38 is to supply a constant current into the actuating coil assembly 11 resulting in a constant force acting on the boss. This constant force is applied to the boss while it moves in the regime of the velocity control. The purpose of this is that it may be advantageous to offset the weight of the boss with this force for a more accurate control of the boss movement.

The circuit will operate in the regime of velocity control from the moment of opening the valve seat and until the moment when the boss reaches the stopper. Once the boss has reached the stopper, the DSP 39 will open the switches 37 and 38 and then the output of the DSP 39 will no longer supply the pattern of the desired velocity of the boss to the feedback operational amplifier but rather a different signal defining the force acting on the boss. As stated above, in order to dampen the bouncing of the boss against the stopper, in some embodiments the feedback is set to regulate the velocity of the boss to zero for a certain duration of time right after the moment when the boss reaches the stopper. For the duration of the damping, the switch 37 remains closed and after the period of damping it will open as specified above. For the duration of the damping, the DSP 39 still supplies the value of velocity to the amplifier 36. Damping is achieved as follows. Bouncing is equivalent to a non-zero velocity. Therefore, if the time response of the feedback is sufficiently short, then the time dependency of the force generated by the actuating coil will be such that the boss will arrive to the stopper and will rapidly lose all the velocity. The desired value for the zero velocity is supplied by the DSP 39 through a Digital-to-Analogue Converter (DAC) 46 and compared with the actual instantaneous velocity as described above. After the completion of the time interval necessary to dampen the velocity of the boss, the switch 37 is open, the magnitude of the force is reduced to a smaller constant value sufficient to keep the boss in the open position pressing it gently against the stopper so that the current through the actuating coil is within safe limits and the actuating coil does not burn out. The magnitude of the force is controlled using the signal from the DSP 39 supplied to the DAC 46 and feedback operational amplifier 36.

When the time is right for closing the valve seat, the DSP 39 closes switches 37 and 38 again. The boss travels back from the stopper to the valve seat according to the velocity control algorithm with the velocity feedback engaged. During this time, the DSP 39 again supplies the circuit with the signal proportional to the desired velocity of the boss. Then the feedback ensures that the boss follows the desired pattern of movement and therefore arrives to the valve seat at the required moment of time. When the boss reaches the valve seat, the DSP 39 opens the switches 37 and 38 again. The circuit switches from the regime of velocity control to the regime of constant force acting on the boss. At the initial moment, immediately after the instant when the boss comes in contact with the valve seat, as with the stopper, it may be advantageous not to switch directly to a the regime of the constant force acting on the boss but instead to a regime of constant velocity and regulate the velocity to zero value. This can prevent bouncing of the boss against the valve seat and therefore prevent uncontrollable opening of the valve. If this algorithm is employed, then after the time interval required for damping the bouncing, it may be beneficial to control the boss in the regime of a small constant force acting on it and pressing the boss against the valve seat. The typical duration of the stage when the bouncing is damped is in the range of some 0.1 to 5 millisecond. After the damping stage, the value of the current in the actuating coil assembly should be such that there is a sufficient force exerted on the boss causing a reliable seal of the dispenser with no leaks and at the same time it is not excessive so that the actuation coil is not in danger of burnout.

It should be appreciated, as already mentioned, that during dispensing of small droplets, the boss may not reach the stopper at all. In this case the algorithm of dispensing is composed in such a way that the boss continuously moves in the regime of velocity/position control until such moment that the boss returns to the valve seat.

In the embodiment shown in FIG. 12, the timing of all transfers between different regimes of boss control, is determined by the DSP 39. The timing depends on the required volume of dispensing and is calculated by the DSP 39 using a suitable software algorithm. Essentially the software has plugged-in pre-calculated values for the all the moments of transfer. The timing depends on the dimensions of the dispenser and some other parameters such as dimensions of the actuating coil assembly. It is advantageous to obtain all the values for the timing of the transfers using a calibration of the dispenser. The control of the movement of the boss between the transfers is done using the analogue feedback. The feedback does not involve the DSP 39 actively but rather takes from DSP 39 input parameter that needs to be regulated, namely, velocity and force. Using this type of hybrid feedback having analogue and digital parts, one can obtain a faster and more accurate feedback performance given the same computing power of the DSP 39.

Different regimes of control such as velocity control, constant force and damping of bouncing as described in this embodiment, directly apply to other embodiments, not based on sensing coils but rather on other types of sensors of boss velocity/position. These details are not repeated when discussing such further embodiments as this would serve no useful purpose.

In a typical embodiment, the electromotive force induced in the sensing coils is some 0.3 to 20 mV. The value of the electromotive force clearly depends on the size of the boss, size of the sensing coil and number of windings in the sensing coil. These values are given for a typical boss size of some 1.5 to 2.5 mm in diameter, length of 5 to 8 mm, made from a material such as high performance SmCo or NdFeB permanent magnet. The boss is magnetised along the axis. Typical velocity of the boss is up to several metres per second.

Figure 13:
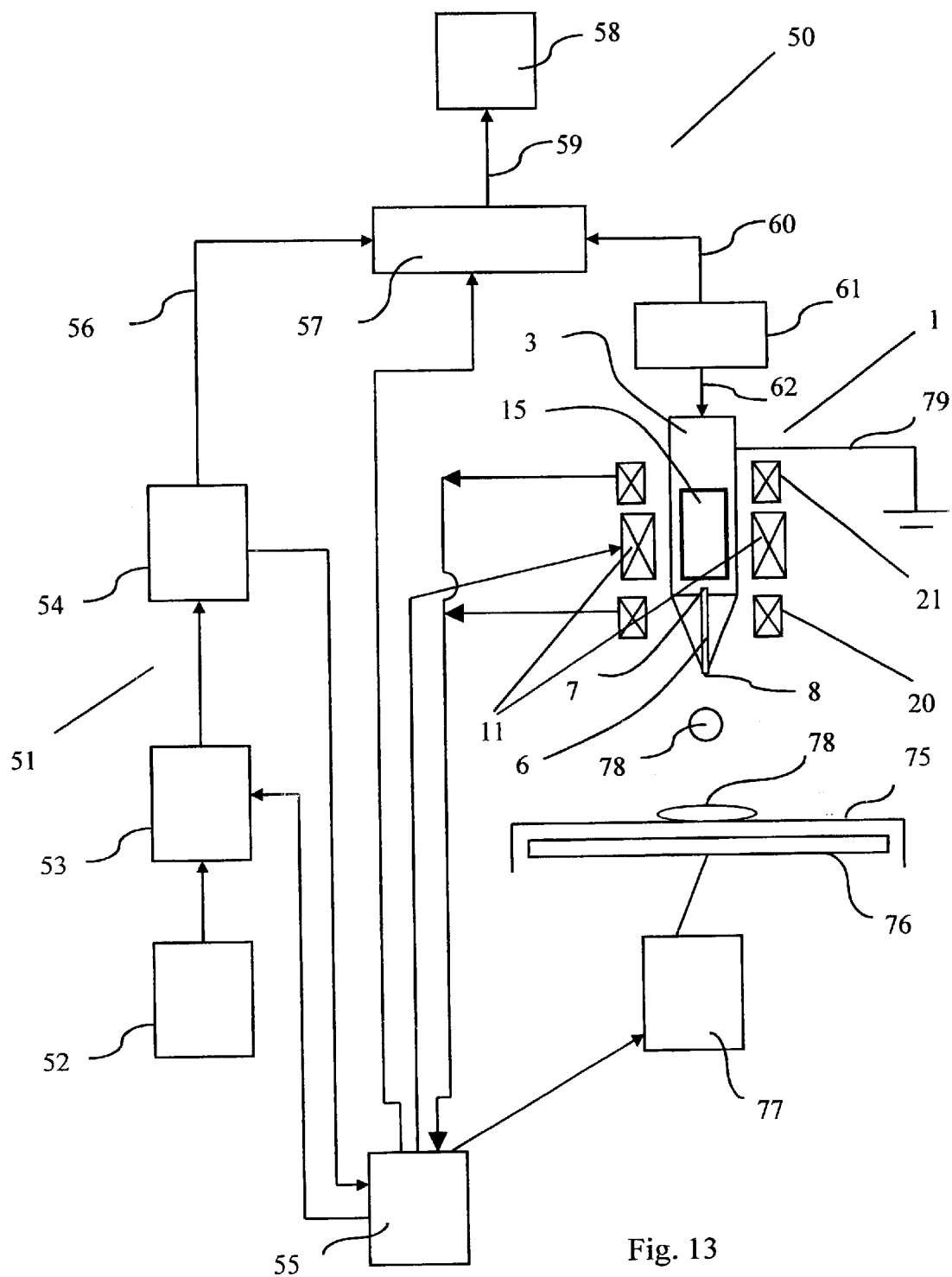
FIG. 13 is a schematic view of a dispensing assembly according to the invention.

Referring to FIG. 13, parts similar to those described with reference to the FIG. 1 are identified by the same reference numerals. In this embodiment, there is illustrated a dispensing assembly for liquid droplets according to the invention, indicated generally by the reference numeral 50. The dispensing assembly 50 comprises a pressurised liquid delivery source indicated generally by the reference numeral 51 which, in turn, comprises a pressure source 52 feeding a pressure regulator 53 and a pressure readout device 54 all connected to an electronic controller 55. The pressure readout device 54 in turn feeds through a high pressure airline 56, a switch 57 which is also fed by a vacuum pump 58 and vacuum line 59. The switch 57 is also connected to the electronic controller 55. The switch 57 connects by a further airline 60 to a sample liquid reservoir 61 which in turn feeds by a pressure/vacuum pipe 62, the dispenser again indicated generally by the reference numeral 1, with a coil actuating assembly 11 and sensing coils 20 and 21. Such a sample liquid reservoir 31 will normally only be used where there is a relatively large amount of liquid been used. Signals from the sensing coils 20, 21 are conditioned and processed by the electronic controller 55. The electronic controller 55 adjusts the current through the coil assembly 11 to achieve the desired profile of the movement of the boss and therefore more accurate timing of the opening of the valve. This could be provided by the circuits of FIGS. 3 and 12.

All the methods of electrostatic drop off, droplet navigation, and measurement of the volume of the drop as described in detail in the patent applications EPO 00650123.3 and EPO 99650106.0 can be also used with the present invention. For this purpose additional elements can be included in the dispensing assembly as briefly described below.

Again referring to FIG. 13 a droplet receiving substrate 75 usually in the form of a series of wells is mounted below the dispensing tip 8 and above a conducting plate 76. The conducting plate 76 is connected to the electronic controller 55 through a high voltage source 77. Liquid when in the form of droplets is identified by the reference numeral 78 in FIG. 13. It will be noted that the dispenser 1 is grounded to earth through an earthline 79, in effect making the dispensing tip 8 an electrode. In some cases, the tip may have to be made out of a conducting material such as metal or an electrically conducting polymer.

In operation, the liquid is stored in the main bore 3 of the body member 2 and the controller 55 is operated to activate the coil actuating assembly 11 to raise the valve boss 15 off the valve seat 7 and to allow the liquid to pass between the valve boss 15 and the walls of the main bore 3 down into the bore of the nozzle 6 until the dispensing coil assembly 11 is activated again to shut off the valve by lowering the valve boss 15. As the valve opens the liquid is supplied to the dispensing tip 8 and the droplet 78 grows. The volume of the droplet 78 is obviously determined by the length of time the valve is open and, the viscosity of the liquid, the cross-sectional area of the nozzle bore, its length and also the pressure exerted on the liquid through the valve from the switch 57. It will be appreciated that if the pressure exerted on the liquid is sufficiently above ambient which is normally atmospheric (1 bar) the droplet will be ejected from the tip 8. However, in many instances, when the pressure is too low or in any case for accuracy, applying a relatively high voltage to the conducting plate 76 will cause an electrostatic field to be exerted between the dispensing tip 8 and the substrate 75 thus causing the droplet 78 to be pulled downwards onto the substrate 75 by a force considerably in excess of gravity. Aspects of electrostatic drop off are discussed in detail in the patent applications EPO 00650123.3 and EPO 99650106.0.

To aspire liquid from a substrate or indeed from any reservoir or container, the vacuum pump 58 is operated and the switch 57 used to ensure that the vacuum pump 58 and vacuum line 59 are connected to the dispensing assembly 50 and the pressure line is disconnected from it. The valve is opened and the liquid sucked up into the dispenser 1.

Figure 14:
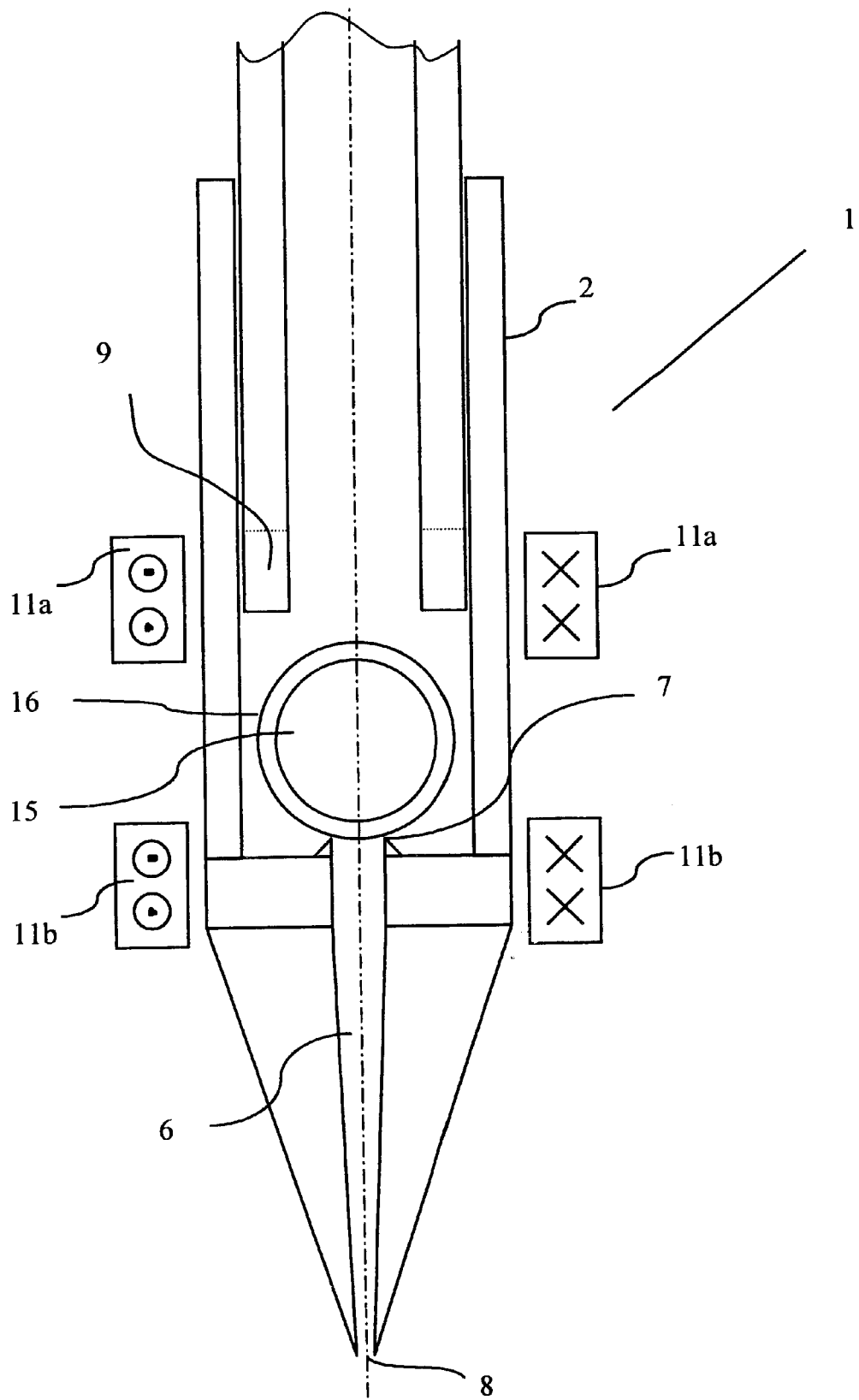
FIG. 14 illustrates an alternative construction of dispenser.

Referring to FIG. 14, there is illustrated an alternative construction of dispenser, again indicated generally by the reference numeral 1. The dispenser and its boss which vary little in construction, are identified throughout the specification by the same reference numerals as almost all the constructional and functional differences between the embodiments relate to the valve boss detector and the controller. Parts generally similar to those described already are, as stated, identified by the same reference numerals. In this embodiment, there is provided a spherical valve boss 15 of a magnetically soft ferromagnetic material such as permalloy or a soft magnetic ferrite which is covered with a soft polymer material 16. The variable power output valve boss actuator comprises a pair of actuating coil assemblies 11a and 11b. The coil assemblies 11a and 11b are also connected to the electronic controller. The purpose of the coil assemblies 11a and 11b is to actuate the boss, moving it towards to and away from the valve seat 7 and to keep it stable in the positions in which the dispenser is open or closed. In a typical arrangement, the coil 11a is energised to move the boss upwards and the coil 11b is energised to move it downwards. The coil assemblies 11a and 11b also detect the position and/or velocity and/or acceleration of the boss. For this purpose, each of the coils 11a and 11b can operate as an actuating and also as a sensing coil. Suppose, the boss 15 is to move up to open the valve seat. In this case the coil 11a is supplied with a current that generates a gradient magnetic field attracting the boss 15 upwards. At the same time the coil 11b operates as a sensing coil. It is then connected to a circuit which can measure the voltage induced in the coil 11b. This voltage has a contribution $V_{ind}$ from the direct inductive coupling between the coils 11a and 11b and also a contribution $V_{boss}$ that is dependent on the velocity of the boss. The first contribution $V_{ind}$ can be measured and subtracted from the total voltage induced in the coil 11b as it is proportional to the rate of the current change in the coil 11a and mutual inductance M between the coils 11a and 11b: $V_{ind}=M*di/dt$. Thus, both values, that of M and that of di/dt can be measured. In this way, it is possible to extract the contribution resulting from the moving boss $V_{boss}$. The contribution $V_{boss}$ is analysed as explained already. It depends essentially on the velocity of the boss and to an approximation is proportional to the velocity of the boss. The velocity can be integrated to obtain the position of the boss in real time if required. The velocity can also be differentiated to obtain the acceleration of the boss if required. Since the boss in this embodiment is made of a soft magnetic material, there is also potentially an additional contribution resulting from the fact that the mutual inductance M between the actuating coil assemblies 11a and 11b depends on the position of the boss 15. It may be advantageous to reduce this contribution resulting from the position of the boss and concentrate on the control based on the velocity of the boss 15 alone. This could be achieved by minimising the travel length of the boss 15 and by other means known to those skilled in the art of magnetic materials and devices such as reducing magnetic permeability of the boss. For moving the boss down to close the valve seat, the roles of the two coils are reversed. Coil 11b is now connected to the current supply and functions as the actuating coil. Coil 11a in turn is connected to the circuit measuring the voltage induced in it and functions as a sensing coil.

Figure 15:
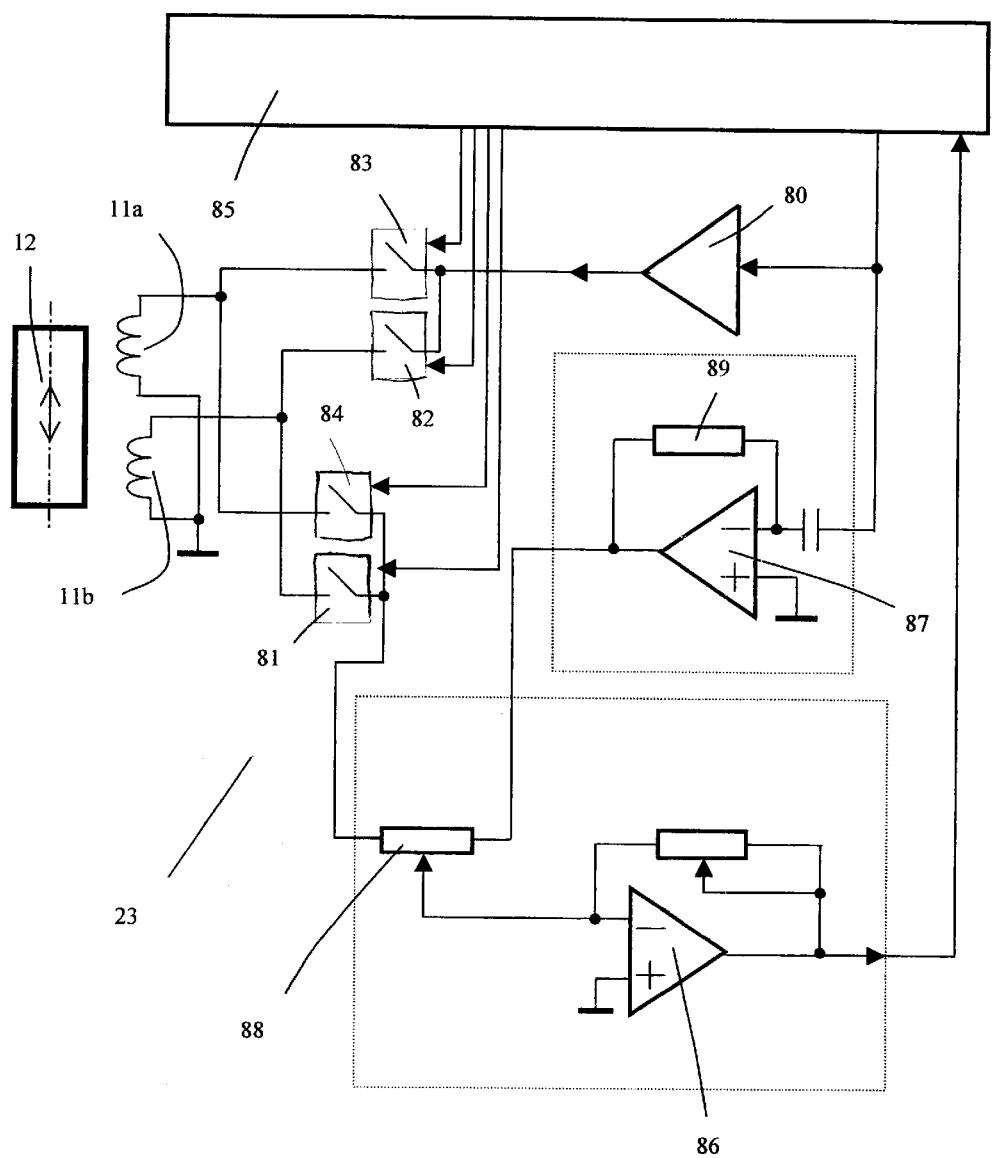
FIG. 15 is a block diagrammatic view of a controller for use with the dispenser of FIG. 14.

FIG. 15 shows, in block diagram form, an electronic circuit forming a controller and detector for the dispenser of FIG. 14. In this case each of the two coils 11a and 11b work as an actuating coil assembly and also as a sensing coil. When one of them is connected to a power amplifier 80, it works as an actuating coil and the other one works as a sensing coil. Connection of the actuating coil assemblies 11a and 11b to the power amplifier 80 and a sensing circuit is carried out by switches 81, 82, 83 and 84 controlled by a feedback controller 85. When, at a particular instant, the coil 11a is connected to the power amplifier 80 to function as the actuating coil assembly, the coil 11b is connected to a signal amplifier 86 to function as a sensing coil and vice versa.

The signal in the coil assembly 11b, acting as the sensing coil, is added to the signal proportional to the derivative of the current in the actuating coil 11a di/dt produced by a differentiator 87. Addition of the two signals takes place on a compensation potentiometer 88. The addition compensates for the voltage $V_{ind}$ induced in the sensing coil due to the direct inductive coupling of the coils 11a and 11b. The same calculations are carried out as heretofore. The output voltage from the differentiator 87 is controlled by a gain resistor 89. The desirable values of the gain resistor 89 and compensation potentiometer 88 depend on the mutual inductance M of the sensing and actuating coils. These values can be optimized using a number of different techniques. For example the boss could be jammed mechanically in one position and an AC current at the frequency of some 1 to 10 kHz could be applied to the actuating coil assembly. This is a typical frequency of spectrum of current in the actuating coil assembly during operation of the dispenser. The compensation potentiometer 88 and gain resistor 89 can be adjusted to minimize the output voltage from the signal amplifier 86. After the compensation, the voltage is amplified by the signal amplifier 86 and sent to the input of the feedback controller 85. The output of the feedback controller is supplied to the power amplifier 80 and then to the actuating coil 11a, as described already.

Figure 16:
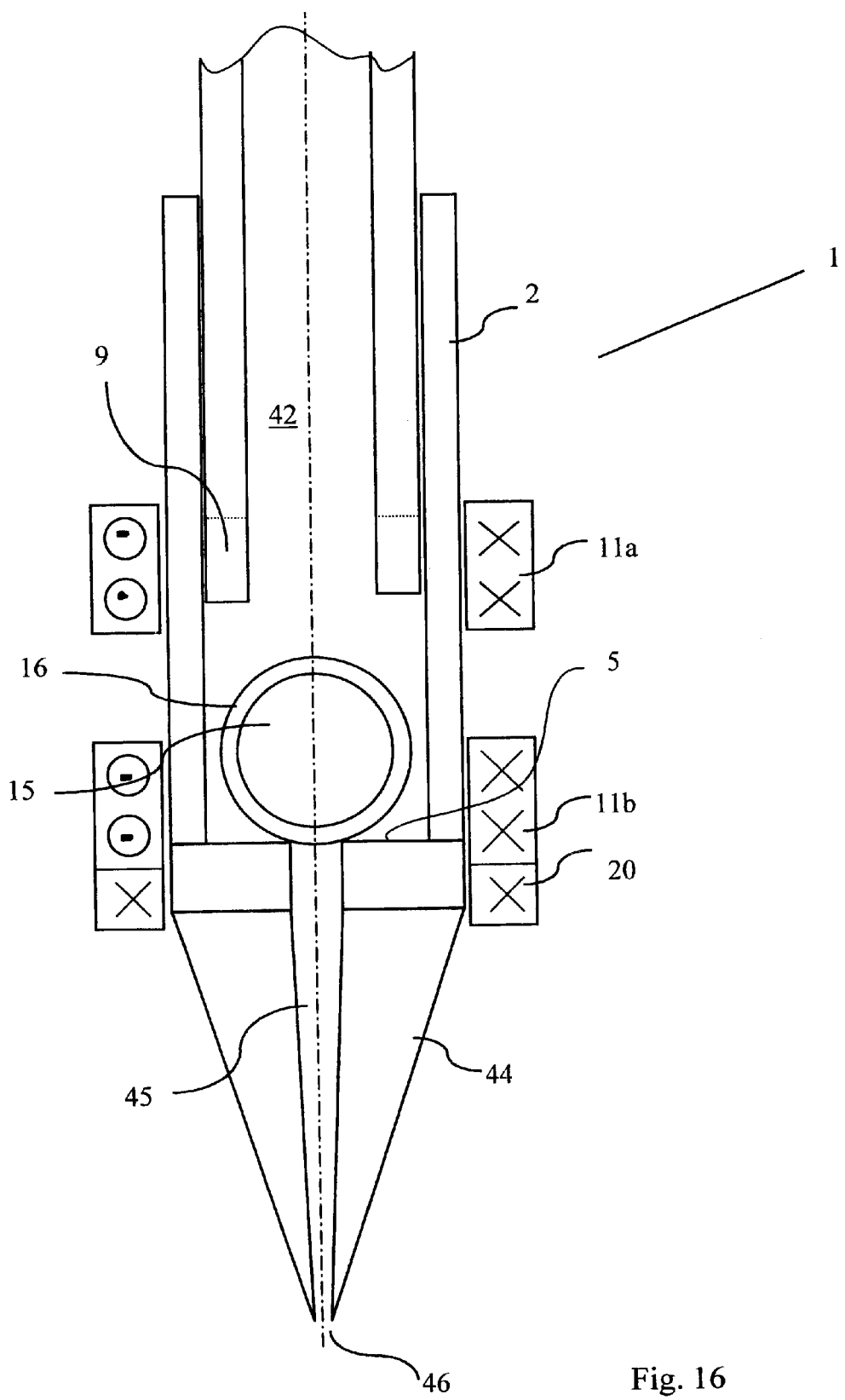
FIG. 16 is a view of an alternative construction of dispenser according to the invention.

Referring now to FIG. 16, there is illustrated another dispenser, again identified by the reference numeral 1, substantially similar to the embodiment already described in FIG. 14, except that additionally there is provided a further sensing coil 20. Again the actuating coil assemblies 11a and 11b are used to move the valve boss 15. However, in this latter embodiment, they are not used to sense the position and/or velocity of the boss. The sensing coil 20 is connected to a suitable circuit for measuring the voltage induced in it.

It is clear that the voltage induced in the coil 20 will have a contribution from the inductive coupling between the pair of coils 11b and 20 and also from the coupling between the pair of coils 11a and 20. As explained already, these contributions are described by the formula $V_{ind}=M*di/dt$ where i is current in the actuating coil, and M is the mutual inductance between the actuating and sensing coils. Voltage induced in the sensing coil 20 will also have a contribution from the moving boss $V_{boss}$ dependent on the velocity of the boss and its position. These contributions are described above. The contribution resulting from the inductive coupling of the coil 20 with the coil assemblies 11a and 11b, can readily be taken into account as the currents and rates of the current change di/dt in the coils 11b and 11a can readily be measured. Therefore, the contribution resulting from the moving boss $V_{boss}$ can be readily isolated, thus giving the position and/or velocity of the boss. The current in the coils 11a and 11b can then be continuously adjusted by the feedback controller to achieve movement of the boss in accordance with the required schedule of movement. The embodiment presented in FIG. 16 has advantages over that of FIG. 14 in that the sensing coil 20 is separate from the actuating coils and therefore better optimisation of the sensing circuit could be achieved. Besides, as there are two actuating coil assemblies instead of a single one, acceleration and deceleration of the boss could be achieved during the upwards and downwards movement of the boss even for a boss of a soft magnetic material. In the embodiment of FIG. 16, the valve seat does not protrude from the base 5.

Figure 17:
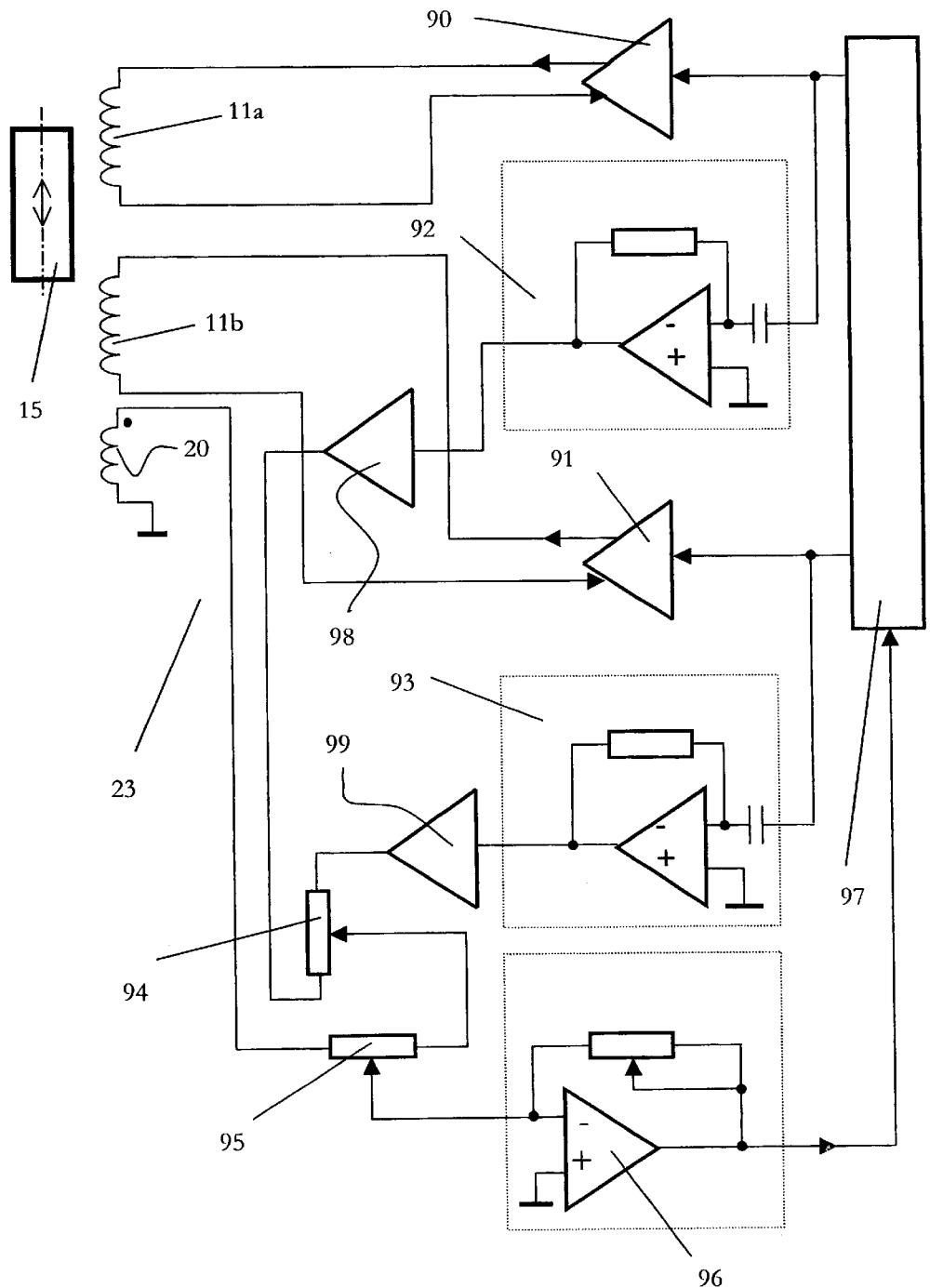
FIG. 17 is a block diagram of an electronic circuit used in the dispenser of FIG. 16.

FIG. 17 shows block diagram of electronic circuit for use with the dispenser of FIG. 16. In this embodiment, there are two power amplifiers 90, 91 connected to the two actuating coil assemblies 11a and 11b. Differentiators 92 and 93, delineated by interrupted lines, form signals proportional to the derivatives over time of the current values in the actuating coils 11a and 11b. The signals proportional to the derivatives of the currents in the two actuating coils are added on a compensation potentiometer 94. This will imitate any signal induced in the sensing coil 20 by the currents changing in the two actuating coil assemblies 11a and 11b. This signal is then added to the signal from the sensing coil 20. The addition of the two signals takes place on a compensation potentiometer 95. The addition compensates for the voltage induced in the sensing coil 20 due to its direct inductive coupling with the actuating coils. After the compensation, the voltage is amplified by a signal amplifier 96 and sent to the input of a feedback controller 97. The outputs of the feedback controller 97 are supplied to the power amplifiers 90 and 91 and then to the actuating coil assemblies 11a and 11b. This has been described in detail above. Since inductive coupling between the coils 20 and 11b is different from the coupling between the coils 20 and 11a, the signals from the differentiators 92 and 93 may need to be added with different weights. For this purpose there are two compensation amplifiers 98 and 99. The gain of the amplifiers 98 and 99 depends on the mutual inductance of the sensing and actuating coils. The appropriate gain of the compensation amplifiers 98 and 99 could be selected using a number of different methods. For example, the boss could be jammed mechanically in one position, and an AC current could be applied to the coil 11a at the frequency of some 1 to 10 kHz. The value of the compensation amplifier 98 could be then adjusted to minimize the output voltage from the signal amplifier 96. Then a similar procedure could be repeated for the coil 11b and the compensation amplifier 99. To some extent the functions of the compensation amplifiers 98 and 99 could be performed by the compensation potentiometers 94 and 95. It may be often desirable to include the compensation potentiometers in the circuit for the ease of adjustment of the circuit.

It is envisaged that the pressurised liquid delivery source could be a positive displacement liquid handling system using a stepper motor incorporating suitable controls operating a piston and a pump containing water or system liquid delivered through flexible tubing to the dispenser. An air bubble could be used to separate the water or system liquid from the sample liquid.

Figure 18:
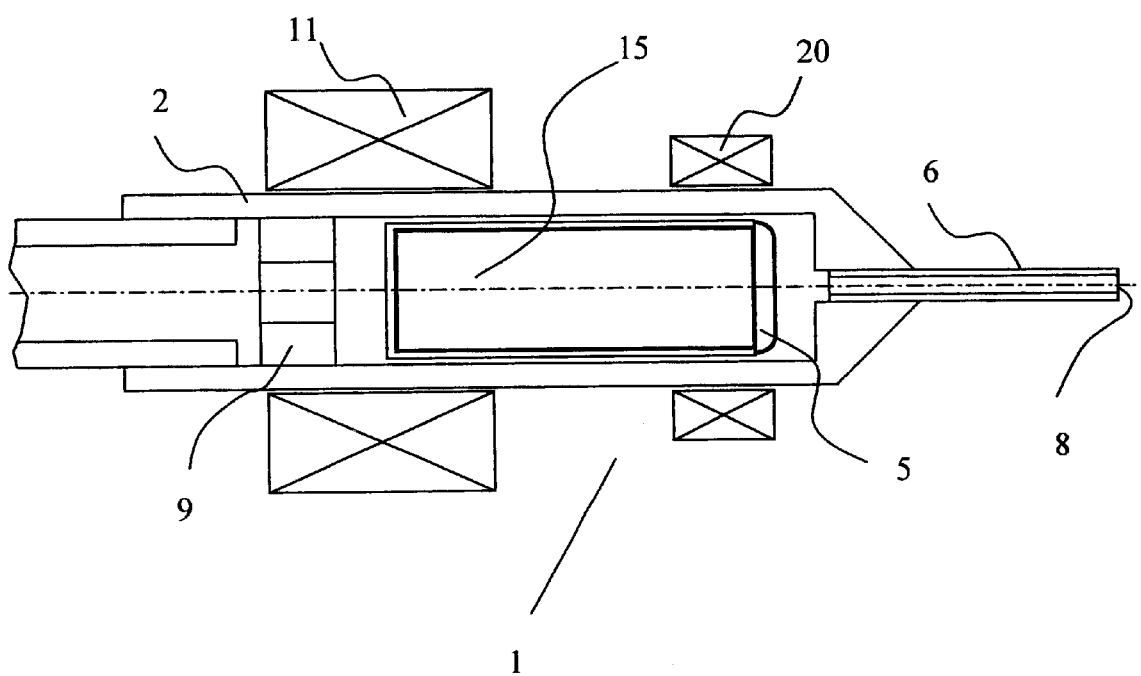
FIG. 18 is a view of an alternative construction of dispenser according to the invention.

Referring to FIG. 18, in which parts similar to those described with reference to the previous drawings are identified by the same reference numerals, there is illustrated a construction of dispenser 1 having one actuating coil assembly 11 and one sensing coil 20 for measurement of the movement of the valve boss 15 whether it be its position, velocity or acceleration. This measurement may be achieved in a number of different ways. When the boss 15 is of a permanent magnetic material, it may be advantageous to measure the total electromotive force $V_{total}$ induced in the sensing coil 20 and extract from it the component of the electromotive force due to the moving boss $V_{boss}$. To extract the component due to the moving boss, one could add a compensation signal to $V_{total}$. As explained already, the compensation signal is to offset the electromotive force induced directly by the actuating coil assembly in the sensing coil that is proportional to the mutual inductance M of the actuating and sensing coils and time derivative of the current in the actuating coil assembly di/dt. To a good approximation, after the compensation the signal detected by the sensing coil due to the moving boss $V_{boss}$ is proportional to the velocity of the boss for any position of the boss inside the dispenser.

Figure 19:
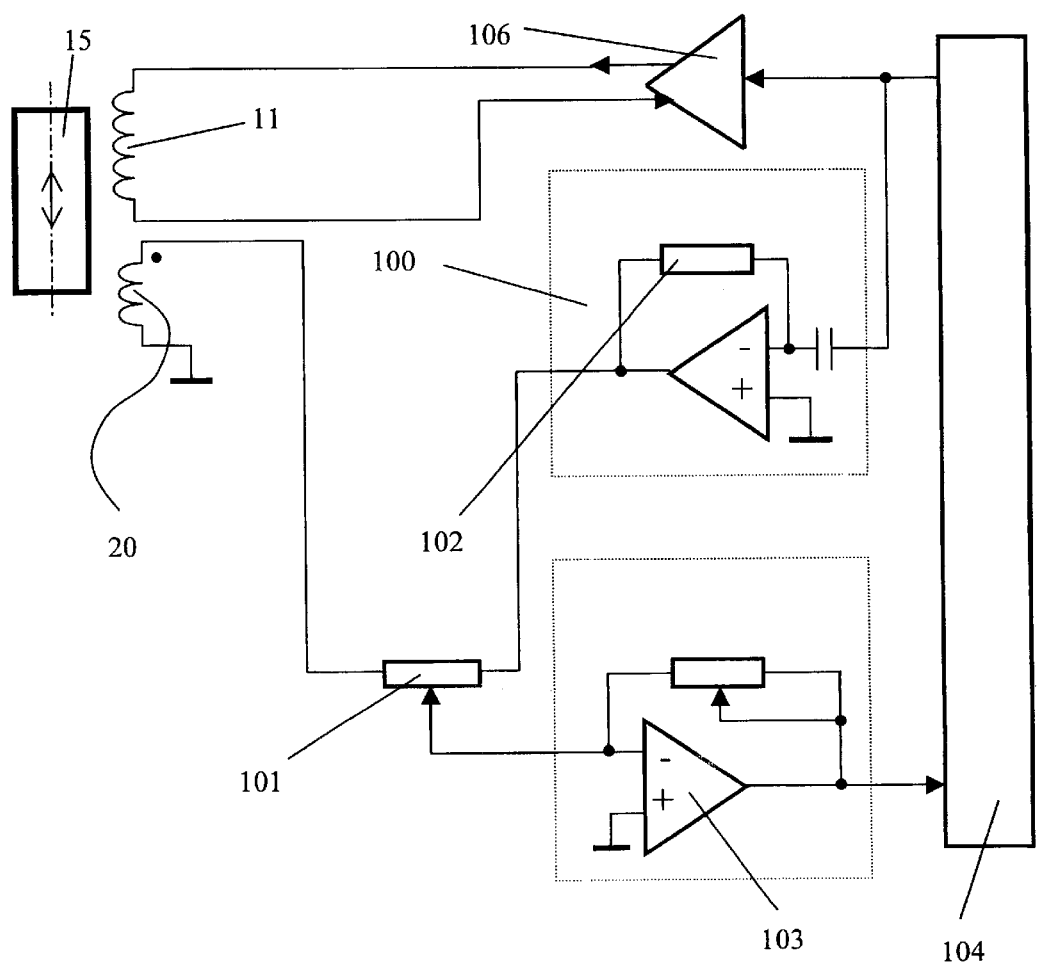
FIG. 19 is a general block diagram of an electronic circuit for use with the dispenser of FIG. 18.

FIG. 19 is a general block diagram of the electronic circuit that can work with the dispenser shown of FIG. 18. In this case the signal from the sensing coil 20 is added to the signal that is proportional to the derivative of the current in the actuating coil assembly 11 produced by a differentiator 100. Addition of the two signals takes place on a compensation potentiometer 101. The addition compensates for the voltage induced in the sensing coil 20 due to the direct inductive coupling of the sensing coil 20 with the actuating coil assembly 11. Then there is added the voltage proportional to the derivative of the current in the actuating coil assembly due to the fact that the voltage induced in the sensing coil due to the inductive coupling of the sensing and actuating coils assembly is essentially proportional to the derivative of the current in the latter di/dt. The output voltage from the differentiator 100 is controlled by a gain resistor 102 and also the required setting of the compensation potentiometer 101 depends on the mutual inductance M of the sensing coil 20 and actuating coil assembly 11. The procedure for their adjustment is as described already. After the compensation, the voltage is amplified by a signal amplifier 103 and sent to the input of a feedback controller 104. The output of the feedback controller 104 is again supplied to a power amplifier 106 and then to the actuating coil assembly 11.

Figure 20:
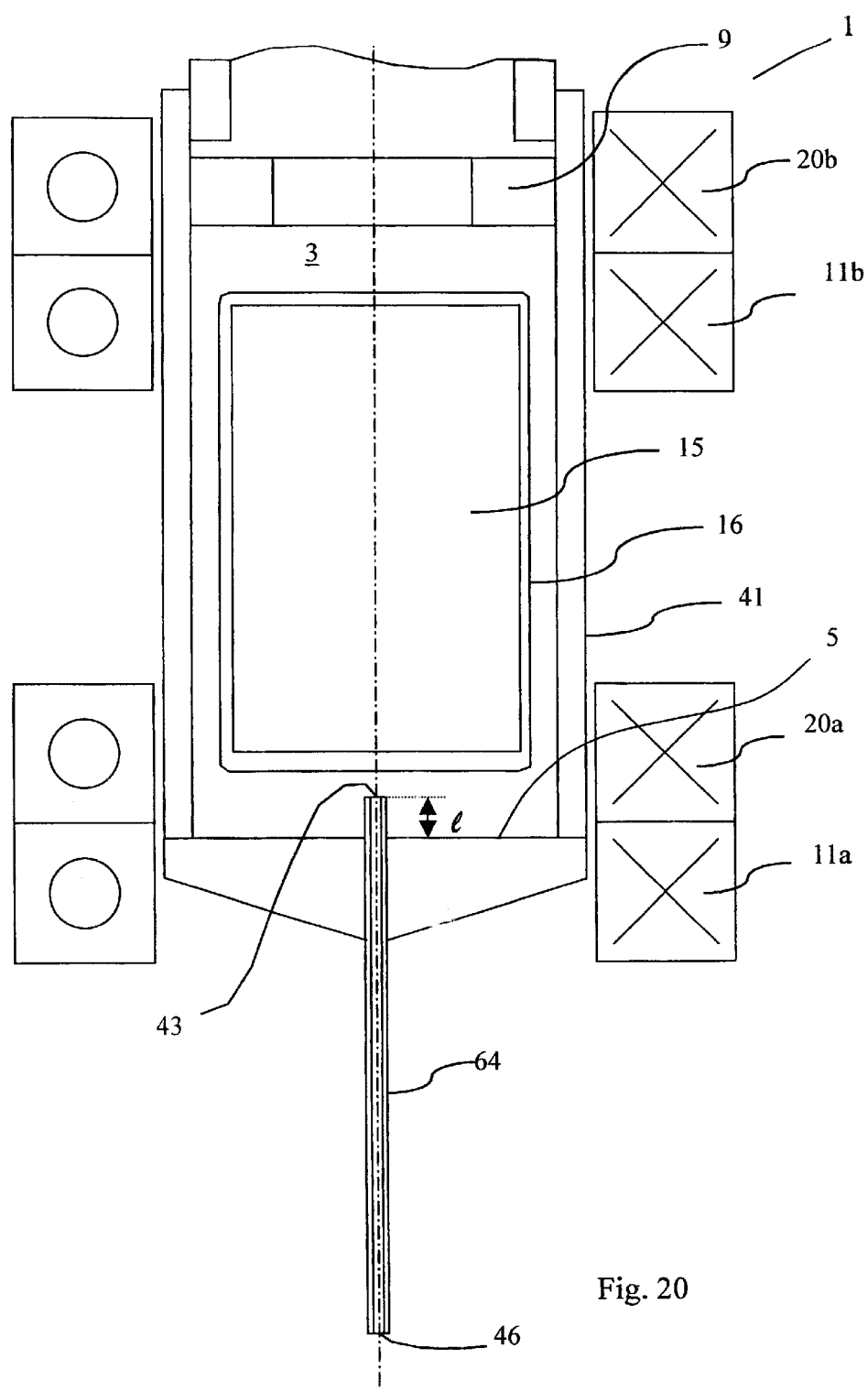
FIG. 20 is a view of a still further alternative construction of dispenser according to the invention.

Referring now to FIG. 20, there is illustrated an alternative construction of dispenser again indicated generally by the reference numeral 1 in which parts similar to those described already are identified by the same reference numerals. In this embodiment, there is provided a cylindrical valve boss 15 of a ferromagnetic material surrounded by a polymer coating 16. There is also provided the boss stopper 9 which is mounted in the main bore 3 remote from the base 5. In this embodiment, the nozzle 64 is formed from a capillary tube which also forms the valve seat 43 which, it will be noted, projects a distance l above the base 5. Both coils 20a and 20b function as actuating coils and they move the boss 15 up and down by means of a gradient magnetic field. Additional sensing coils 11a and 11b are provided. One of the sensing coils, e.g. the coil 11a is supplied with AC current at a frequency $f_o$, say 50 kHz or 200 kHz. Coil 11b collects the signal at the frequency $f_o$ to identify position of the boss. The signal from the coil 11b is supplied to a lock-in amplifier (or another suitable sensitive amplifier) measuring the voltage at the same reference frequency $f_0$. The signal induced in the coil 11b is a result of direct electromagnetic inductive coupling between the coils 11a and 11b and also oscillation of magnetisation of the boss 15 changing the flux through the coil 11b. The reason for this is clear: the boss 15 is placed in the oscillating field of the coil 11a. This field oscillating at the frequency $f_o$ will induce the oscillating magnetic moment at the boss 15 which will in turn induce oscillating magnetic flux through the coil 11b at the same frequency $f_o$. In other words, the additional field induced by the boss in the coil 11b is due to the magnetic permeability of the boss. The boss 15 is made of ferromagnetic material and therefore its permeability is considerably different from that of air or any other material positioned between the coils 11a and 11b such as biological liquids or polymer materials. As the signal induced in the coil 11b is dependent on the position of the boss 15, this position can be calculated from the measurements. The current supplied to the actuating coils 20a and 20b can be changed accordingly to adjust movement of the boss to follow the required schedule.

Functionally coils 11a and 20a could be combined in one coil, in the same way as the coils 11b and 20b could be also combined. This would require a different electronic circuit capable of separating the voltage due to the actuating current from the voltage induced at the frequency $f_0$.

Unlike in the previous embodiment where the velocity of the boss was monitored, in this embodiment involving applying oscillating field at the frequency $f_0$, the position of the boss is directly monitored. Velocity and acceleration of the boss may be readily calculated from its position if so required. The value of the frequency $f_o$ depends on the required speed of the dispenser controller. If the frequency $f_o$ is too low, the amplifier measuring the signal from the sensing coil will not be able to perform measurements fast enough. For this reason, it has been found convenient to have the frequency $f_o$ in the range of 50 kHz or greater. In this case the lock-in amplifier can readily perform measurements with a time constant smaller than a fraction of a millisecond making it adequate for a typical dispenser with the dimensions as described above. On the other hand, if the frequency $f_o$ is too high, such as in excess of 500 kHz, the magnetic permeability of some suitable materials is reduced at this frequency thus decreasing the signal detected by the sensing coil. Lock-in amplifiers suitable for frequencies in excess of 500 kHz tend to be more expensive devices.

Figure 21:
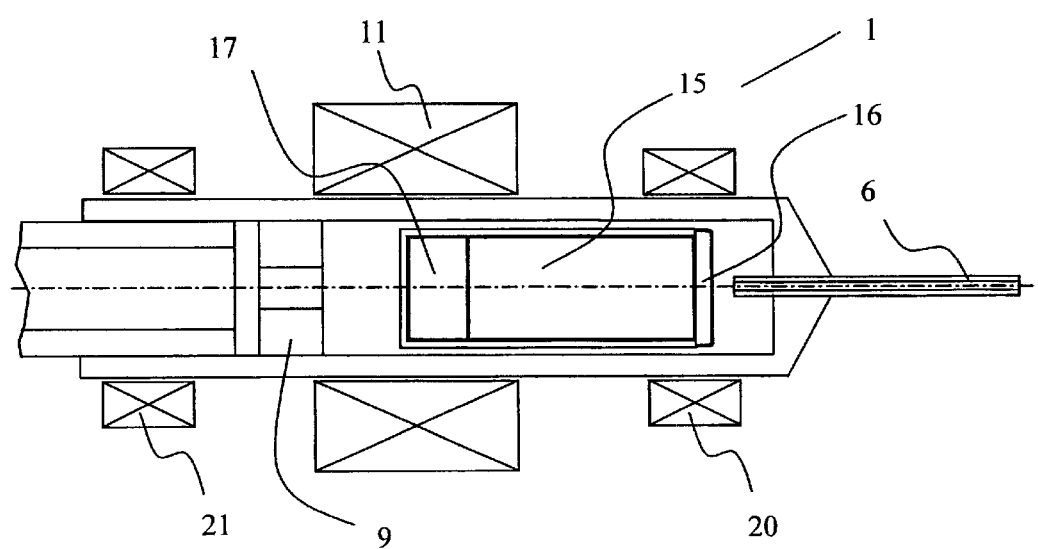
FIG. 21 is a view of a still further construction of dispenser.

It may be therefore beneficial to use for the boss a soft ferromagnetic material or ferrite having high magnetic permeability at the frequency $f_o$. There are many suitable materials for this purpose such as soft ferrites, soft iron-nickel alloys and others. The list of suitable materials includes soft magnetic alloys such as sold under the Trade Marks MUMETAL, VACOPERM, ULTRAPERM, PERMENORM, by Vacuumscmelze GmbH, Germany. Numerous other companies manufacture soft magnetic materials such as Kane Magnetics, USA; Fair-Rite Products Corp, USA or Dexter Magnetic Materials, UK. When choosing a material for its magnetic permeability one has to appreciate that in the applications of the invention, the real value for permeability can be lower than the values indicated by manufacturers. The reason is that the boss is placed in a magnetic field of the actuating coil assembly. When materials with high permeability are placed in an offset magnetic field, their permeability often decreases. In the embodiment of FIG. 21 described in more detail below, a marker of soft magnetic material 17 is attached to a boss of a permanent magnetic material. In this case, the marker is placed in a DC magnetic field produced, for example, by the rest of the boss. This can also reduce the effective magnetic permeability of the marker.

While all the bosses described above have been either spherical or cylindrical and thus circular in cross-section and similarly all the bores have been circular in cross-section, this is not necessarily essential. For example a boss could be made of any suitable shape. It could be square, rectangular or polygonal in cross-section. Similarly the bore does not have to be circular in cross-section. Nor indeed do both the bore and the boss have to be of the same shape in cross-section. Essentially the boss can form an elongate plug-like member which effectively is constructed for limited movement at a line with the main bore.

Referring to FIG. 21, there is illustrated a dispenser, again indicated generally by the reference numeral 1 which is identical to the dispenser, at least physically, of FIG. 1 except that the boss 15 includes a marker 17 of a soft magnetic material and the remainder of the boss 15 is of a hard magnetic material, again covered by a soft polymer material 16. In this embodiment there are two sensing coils 20 and 21 located at two opposite ends of the actuating coil assembly 11. The actuating coil assembly 11 is supplied with a current to move the boss 15 within the dispenser and also with a superimposed oscillating current at a frequency $f_o$, generally between 30 kHz and 200 kHz. It will be appreciated that numerous other appropriate values of the frequency $f_o$ could be selected by those skilled in the art. The oscillating current will generate an oscillating magnetic field at the frequency $f_o$ which will modulate the magnetisation in the boss at the same frequency. The two sensing coils, namely, the sensing coil 20 and sensing coil 21 receive a signal resulting from several contributions. The important contributions are:

1. contribution from the varying actuating current in the actuating coil assembly 11 moving the boss 15;
2. contribution from the oscillating current at the frequency $f_o$ superimposed on the actuating current. This causes oscillating magnetic flux through the sensing coils 20 and 21;
3. contribution from the moving boss 15. This contribution has been described in detail in discussion related to FIG. 1; and
4. contribution from the oscillating magnetic moment of the boss caused by the oscillating magnetic field at the frequency $f_o$. This will cause the electromotive force at the same frequency $f_o$.

The contributions 1 and 2 can be cancelled by taking the difference between the electromotive forces induced in the sensing coils 20 and 21. This may be particularly easy to achieve if the two sensing coils are identical and are located at the same distance from the actuating coil assembly 11. Even if this is not the case, effective cancellation of the contributions 20 and 21 could be achieved in many instances. At the same time, the contributions 3 and 4 contain information about the moving boss 15. The contribution 3 is a function of the boss' position and velocity. The contribution 4 is effectively dependent on the position of the boss only. One can readily separate the contributions 3 and 4 since they have completely different spectra: contribution 4 is a narrow-band signal with the spectrum centred around the frequency $f_o$. Therefore, by measuring the amplitude of the electromotive force in the sensing coils 20 and 21, at the frequency $f_o$, and by calculating the difference between the two coils, the position of the boss can be recorded and measured at any given instant.

It is envisaged that it may be advantageous to measure both contributions 3 and 4 simultaneously. In this case the feedback could be based on both values: velocity of the boss and its position. To increase the signal contribution 4 it could be advantageous as in this embodiment to attach a marker of a soft magnetic material to the boss. This could be, for example, a layer of iron, permalloy or soft ferrite as shown with the numeral 17 in FIG. 21. The reason for this is that magnetic permeability of many hard magnetic materials is not very high. The contribution 4 into the signal is dependent on the magnetic permeability of the boss. In many instances the contribution 4 is directly proportional to the magnetic permeability.

There are many ways of placing the magnetic marker on the boss and many locations where the marker could be placed. A plurality of markers could be placed instead of a single one. One can appreciate that there numerous other ways of increasing the magnetic permeability of the boss. For example one could use a composite magnetic material that although being regarded a permanent magnetic material still has a considerable magnetic permeability. Magnetic permeability of many magnetic materials is a function of the frequency of the excitation magnetic field. It is thus important to ensure that the magnetic permeability of the marker material is high at the frequency $f_o$, and not just in a DC magnetic field. The frequency dependency of the marker material can be an important consideration in the overall choice of the operating frequency $f_o$.

It is necessary to appreciate that the two sensing coils do not need to be identical and do not need to be located at the same distance from the actuating coil assembly. In fact, in one embodiment of the invention, the sensing coil 20 is smaller in diameter than the sensing coil 21. This difference is due to the shape of the dispenser that favours such a solution. From the point of measurement of the boss position, there is no need to make the coils identical. As will be clear from the description above, the contributions 1 and 2 can still be cancelled by adjustment of a balance potentiometer.

It should be appreciated that it is not necessary to cancel both the contributions 1 and 2 listed above simultaneously. If the readout of the boss position is based on measurement of the contribution 4, then it is sufficient to compensate for the contribution 2. The reason being that the contribution 1 has a different frequency spectrum from the signal contribution 4. Therefore, one can readily extract the contribution 4 by measuring the electromotive force induced in the coils 20 and 21 in a narrow frequency window around $f_o$.

Figure 22:
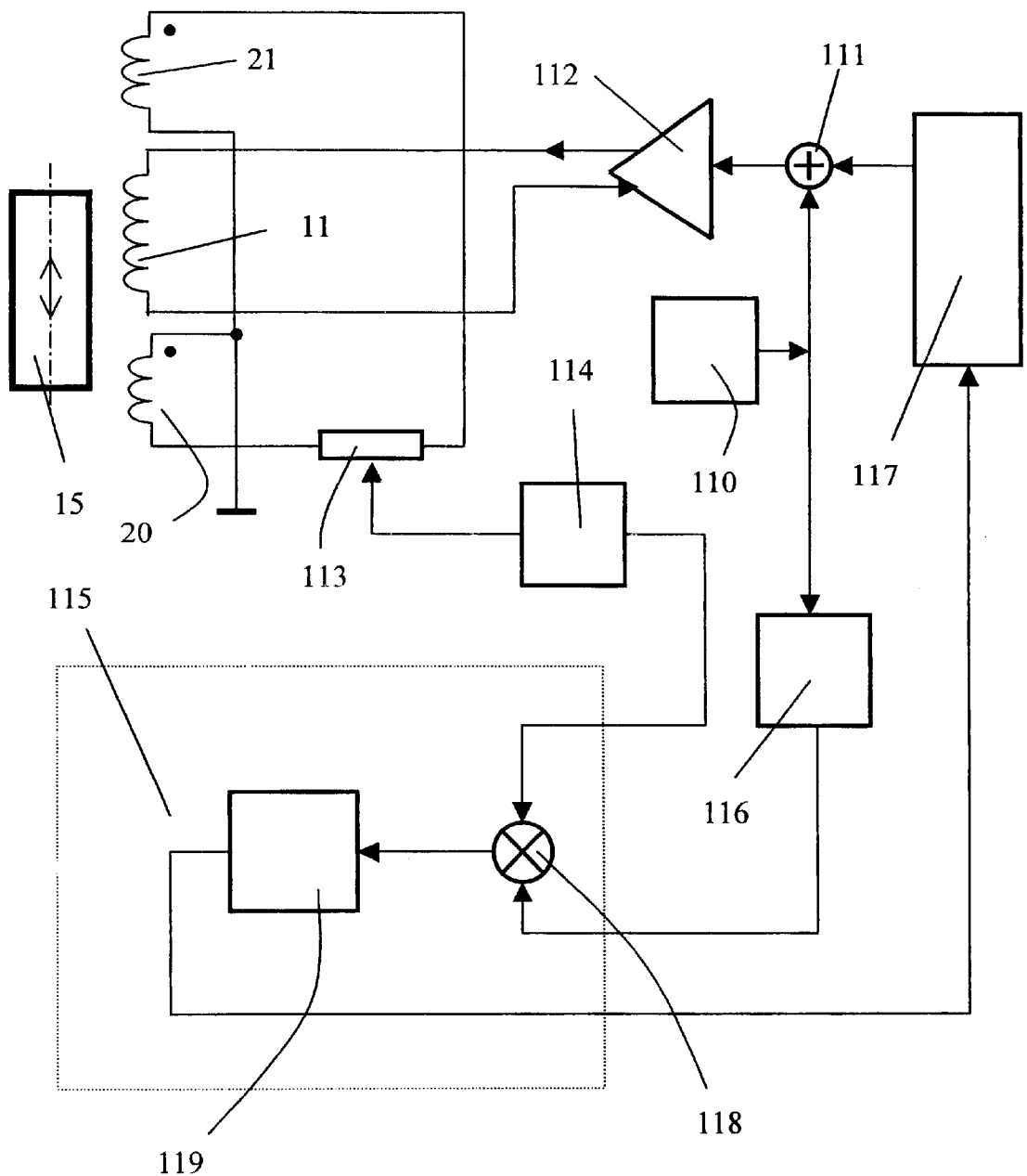
FIG. 22 is a block diagram of an electronic circuit suitable for use with the dispenser shown in FIG. 20.

FIG. 22 illustrates block diagram of an electronic circuit suitable for the dispenser shown in FIG. 21. A sine wave oscillator 110 generates a signal at frequency $f_o$. This signal is mixed at a mixer 111 with the signal supplying current to the actuating coil assembly 11. The signal is then amplified by a power amplifier 112 and supplied to the actuating coil assembly 11. Voltages from the sensing coils 20 and 21 are added together at a balance potentiometer 113. This is then passed through a band-pass filter 114 tuned to pass the signal at the frequency $f_o$. After the band-pass filter 114 the signal is supplied to a synchronous detector 115 (this device is also known as a lock-in amplifier) comprising a fast analogue multiplier or demodulator 118 and a low-pass filter 119. The analogue multiplier or demodulator also requires the reference signal. The reference signal is supplied to it from the sine wave oscillator 110 through a phase shifter 116. The signal from the lock-in amplifier 115 is supplied to a feedback controller 117. The feedback controller 117 produces an output signal proportional to the current that is necessary to move the boss as required. It will be appreciated that one could readily design a circuit in which the AC signal mixed with the actuating signal is not a sine wave but a modulation periodic signal of a different shape.

Figure 23:
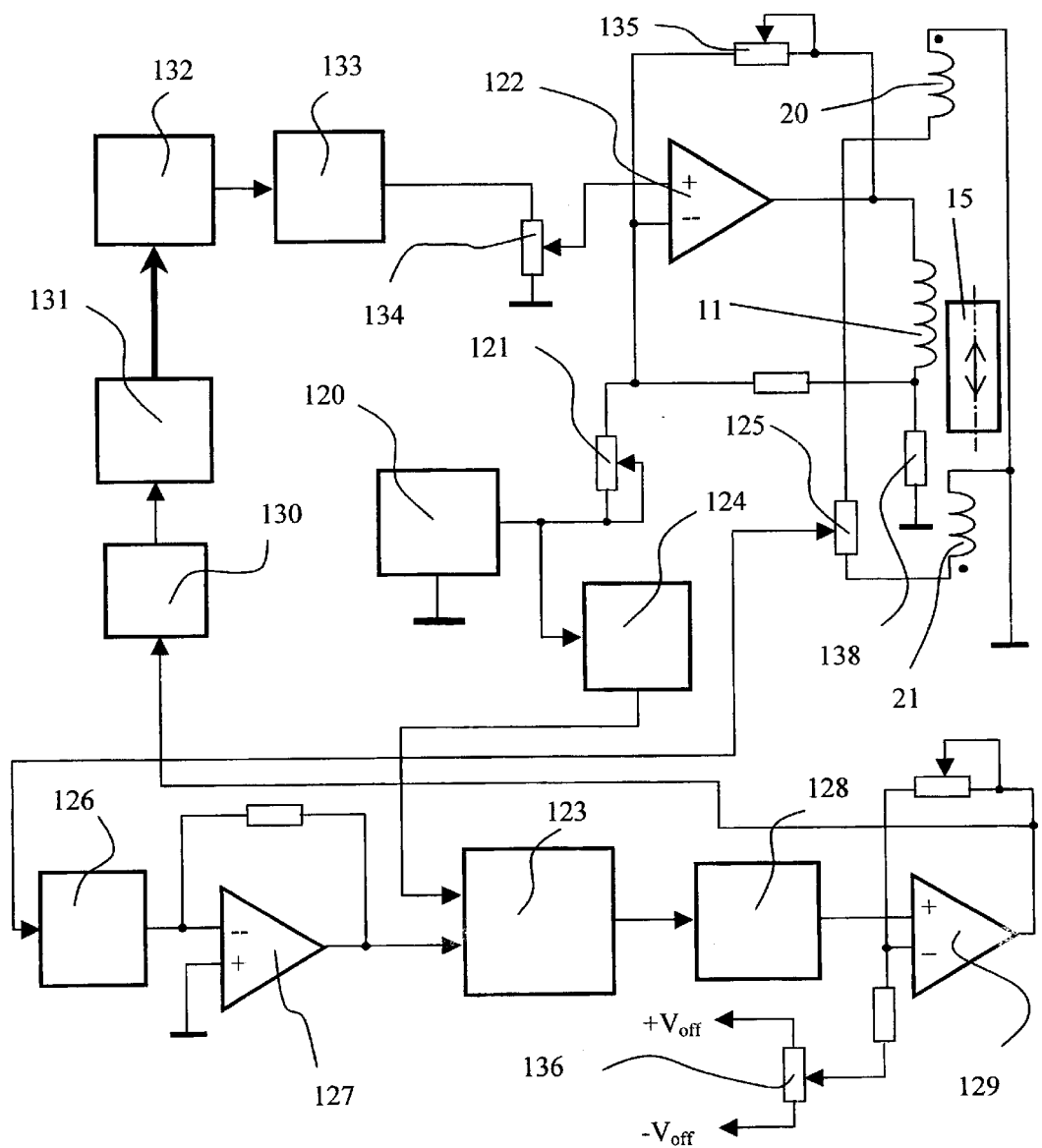
FIG. 23 is an electronic circuit for use with the dispenser of FIG. 21.

FIG. 23 shows an electronic circuit in more detail that can operate with dispenser shown in FIG. 21. A sine wave oscillator 120 generates a signal at the frequency $f_o$. This is supplied to the actuating coil assembly 11 through a variable resistor 121 and then through a power amplifier 122. This signal is also supplied to a lock-in amplifier 123 through a phase shifter 124 as a reference signal. Voltages from the sensing coils 20 and 21 are added together at a balance potentiometer 125. This is then passed through a band-pass filter 126 tuned to pass the signal at the frequency $f_o$. The purpose of the filter 126 is to improve the signal to noise ratio. 30 After the band-pass filter 126 the signal is amplified by an amplifier 127 and supplied to the lock-in amplifier 123. The signal from the lock-in amplifier 123 is supplied to a low-pass filter 128 that allows passing through frequencies of up to some 5 or 10 KHz. The signal is then amplified by a further amplifier 129 and supplied through an ADC 130 to a DSP 131. At the output of the DSP 131 the signal is supplied to a DAC 132. Then it is passed through a low-pass filter 133 cutting the frequency spectrum above 0.5 $f_o$. This is done to avoid cross-over of the spectrum of the actuating current and the modulation current at the frequency $f_o$. The signal is then supplied through a potentiometer 134 to the power operational amplifier 122 and then to the actuating coil assembly 11. A gain resistor 135 determines the gain of the power amplifier 122. The DSP 131 is supplied with the desired movement algorithm that should take into account dimensions of the dispenser and the boss, and should be calibrated so that the signals corresponding to the boss when in the fully open and fully closed positions are known. The low pass filter 133 is an optional feature and is not essential. The frequency is determined by the required speed of the dispenser. If this frequency is set too low, the circuit sensing movement of the boss will have a too large time constant and this will slow down the whole operation. A potentiometer 136 is used to facilitate adjustment and calibration of the circuit.

Figure 24:
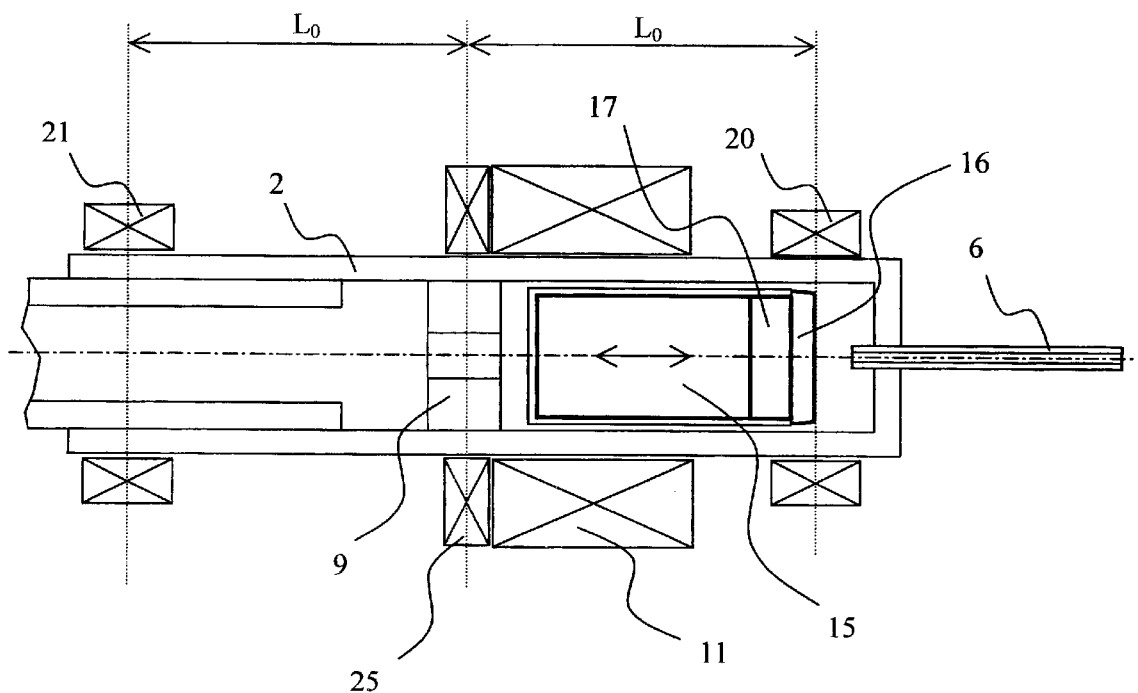
FIG. 24 illustrates a still further construction of dispenser.

FIG. 24 illustrates an embodiment of a dispenser substantially identical to the dispenser of FIG. 21 again having two sensing coils 20 and 21 for readout of the position of the boss 15, an actuation coil assembly 11 and a separate excitation coil 25 for generating the oscillating magnetic field at the frequency $f_o$. The principle of operation of this dispenser is similar to that of FIG. 21 except the excitation coil 25 is separate from the actuating coil. This may simplify the electronic circuit of the controller for the dispenser.

Figure 25:
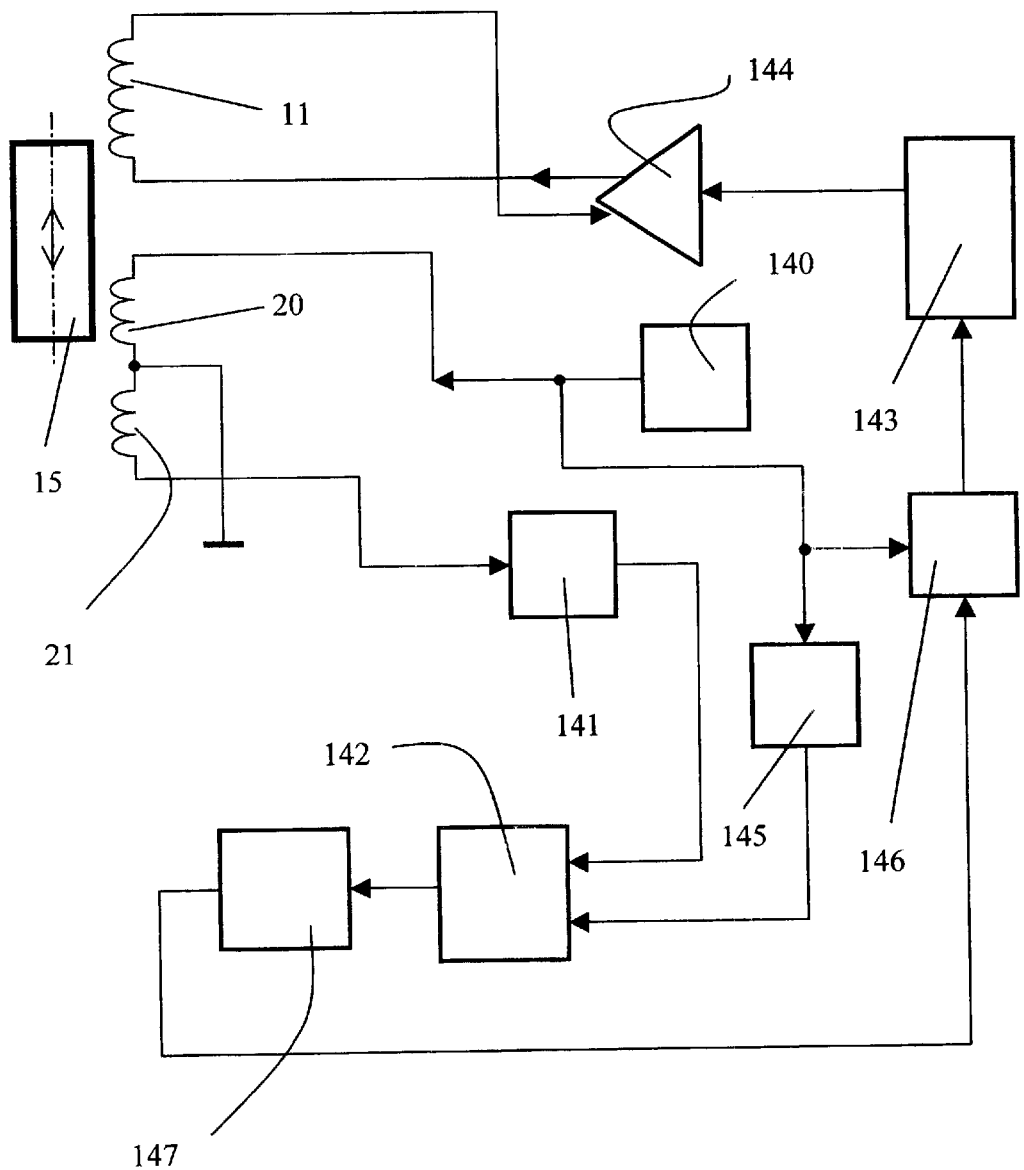
FIG. 25 is a block diagram of control means for the dispenser of FIG. 24.

FIG. 25 shows a block diagram of control means for the dispenser of FIG. 24. Two sensing coils 20 and 21 are inductively coupled with each other. Mutual inductance between the coils 20 and 21 depends on the position of the boss 15. A sine wave oscillator 140 supplies AC current through the sensing coil 20. A signal from the sensing coil 21 is supplied to a band-pass filter 141 and then to a lock-in amplifier 142. A signal from the output of the lock-in amplifier 142 is supplied to a feedback controller 143. Output from the feedback controller is supplied to a power amplifier 144 and then to the actuating coil assembly 11. A reference signal is supplied from the sine wave oscillator to the lock-in amplifier 142 through a phase shifter 145. There is a compensator 146 installed between the output from the lock-in amplifier 142 and the feedback controller 143. The purpose of this is to offset the signal induced in the sensing coil 21 by the sensing coil 20 and the boss at the initial position (for example, fully closed dispenser). The compensator 146 is optional. After the compensation, the signal supplied to the input of the feedback controller 143 is set to zero for the initial position of the boss 15. Movement of the boss from the initial position will result in a net signal appearing at the input of the feedback controller 143 that is dependent on the position of the boss 15. An optional low-pass filter 147 may be used.

The invention, it should be noted, uses the principle that the electromotive force induced in a sensing coil depends on the position of the boss relative to the coil and its velocity. For any given position of the boss it is indeed proportional to the velocity of the boss if the boss is made of a material with zero magnetic permeability. However, in practice, it is also a function of the position of the boss with regard to the coil. As explained above, there are reasons ensuring that the signal induced in the sensing coil is not only a function of velocity of the boss, but to a certain extent, also of its position. For example, magnetic permeability of the boss can change the inductance of the sensing coil. This may result in additional dependency of the signal induced in the coil on the position of the boss. Therefore, for improved accuracy of the boss control, it is envisaged that in many instances, it may be advantageous to use two sensors simultaneously: one for the velocity control and the other one for the position control. The controller could collect a signal from the two sensors simultaneously and process the data in such a way that the signal sent to the actuating coil assembly enables a more accurate movement of the boss in line with the required schedule to achieve the desired volume of dispensing.

Figure 26:
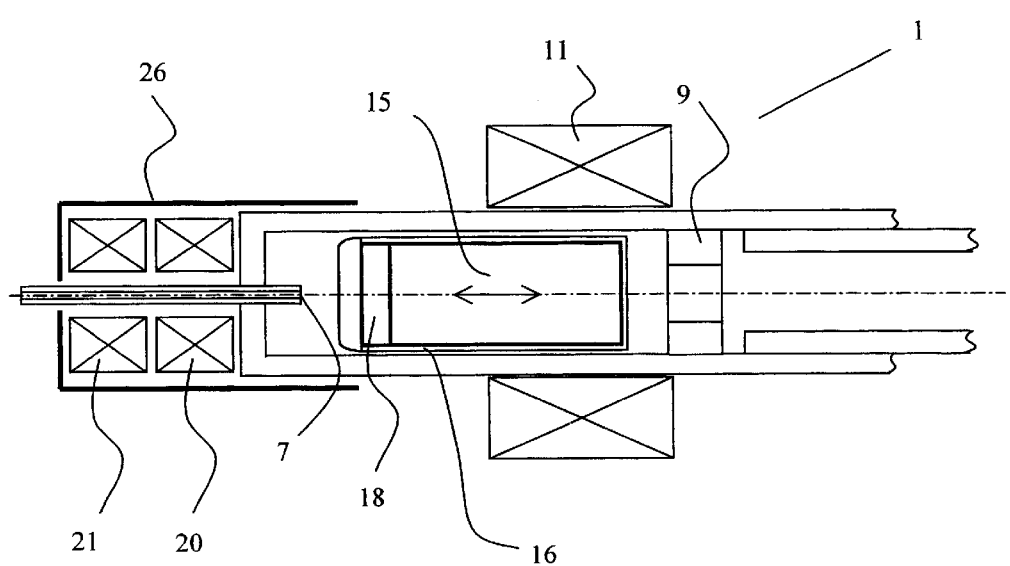
FIG. 26 is a view of another dispenser.

Referring to FIG. 26, there is illustrated an alternative construction of dispenser. The sensing coils 21 and 20 located close to the valve seat 7 are housed within a conducting shield 26. This dispenser works using the sensing coils as part of an Eddy current sensor.

One of the sensing coils 20 is excited with an AC current at a frequency $f_1$, for example, 100 KHz. Electromotive force at the same frequency $f_1$ is induced in the other sensing coil 21. This electromotive force is measured using an external controller. If a conducting boss is brought into direct proximity of the sensing coil 20, there will be a pattern of eddy (image) current induced in the boss 15. This pattern will generate its own AC magnetic field at the same frequency $f_1$. In most cases this additional magnetic field will be directed in such a way as to partially cancel the AC magnetic field directly induced in the sensing coil 21 by the sensing coil 20. Therefore, as the conducting boss approaches the valve seat, the electromotive force induced in the sensing coil 21 will change. Generally it will decrease. Therefore, by monitoring the electromotive force induced in the sensing coil 21 at the frequency $f_1$, one can identify the instant position of the boss. The valve boss, again identified by the reference numeral 15, includes as well as an outer soft polymer layer 16, a layer 18 of high conductivity material such as copper, silver or aluminium.

The layer 18 can be required with those some permanent magnetic materials which have rather low conductivity. The conducting shield 26 reduces the influence of other conducting objects approaching the dispenser 1. The boss in this embodiment is actuated using an actuating coil assembly 22 in the same way as in the previous embodiments.

The controller illustrated in FIG. 25 with some optional minor changes can be also used for control of the dispenser of FIG. 26. Clearly, this is only one possible circuit. Other circuits could be designed by any skilled circuit developer. Detection can be linked to the magnetic permeability of the boss or to its conductivity. Similar control circuits can be applied in both cases as in both cases the boss movement will result in a change in electromotive force induced in a sensing coil 21 at the frequency of excitation of the other sensing coil 20. Movement of the boss in both cases is accomplished by using the same mechanism of changing current in the actuating coil assembly. In both cases, the direct inductive coupling between the sensing coils for a well-defined position of the boss, can be compensated by a compensator circuit such as, for example, shown in FIG. 25.

Calibration of the dispensers could be achieved, for example, as follows. The signal induced in one of the sensing coils is recorded for two positions of the boss: (i) boss pressing against the valve seat (fully closed dispenser) and (ii) boss pressing against the stopper (fully open dispenser). Then a linear approximation of the amplitude of the signal is taken as a function of the boss position between these two extreme positions (i) and (ii). If the circuit employs a compensator as shown in FIG. 25, then the compensator could be adjusted to balance the signal for one of these two positions, for example, boss pressing against the valve seat. Then a linear approximation could still be used in which the signal after the compensator is equal to zero for the fully closed dispenser and gradually increases/decreases to a certain value as the boss moves towards the stopper to fully open the dispenser.

Figure 27:
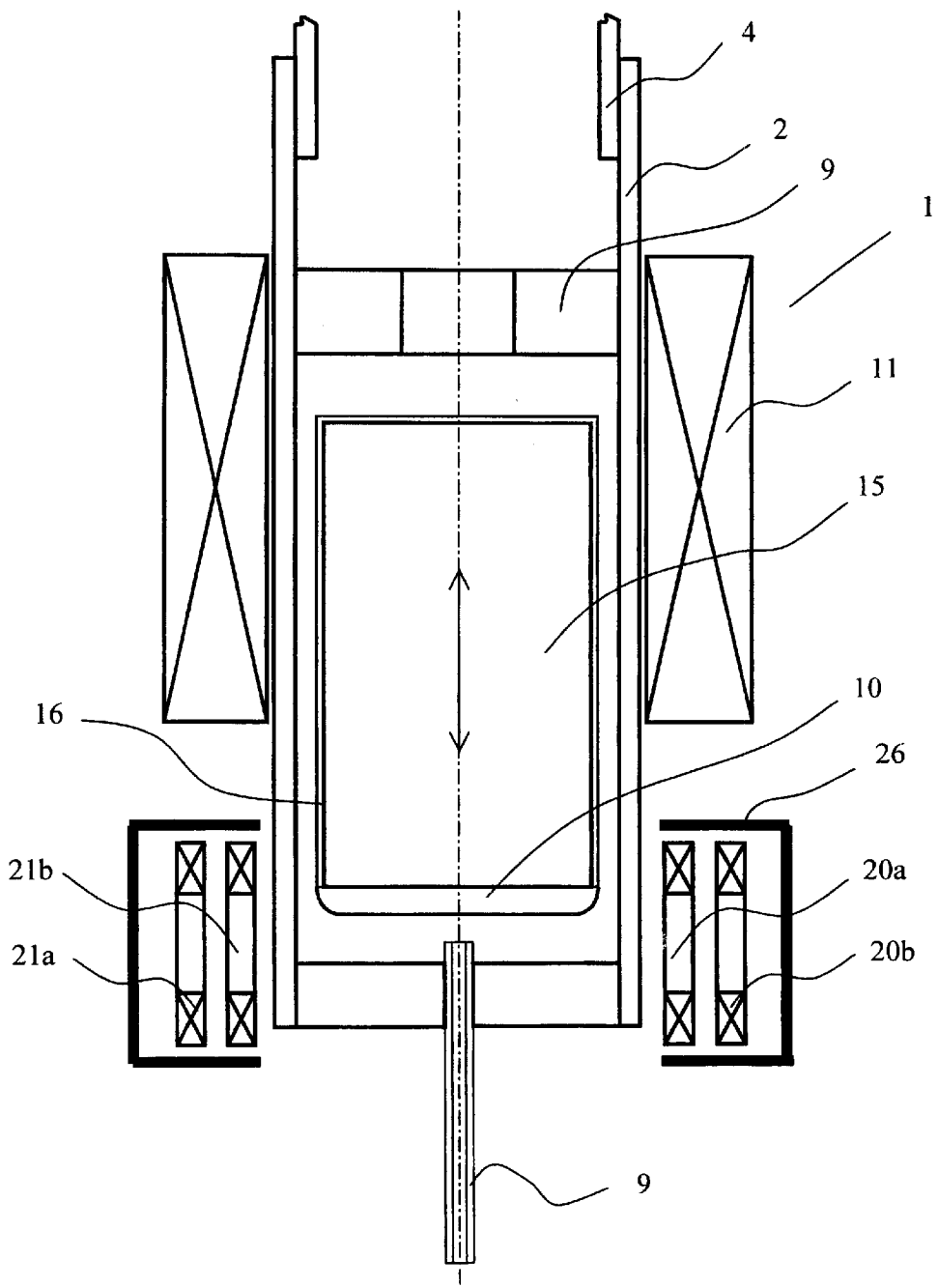
FIG. 27 is a view of a still further dispenser.

Referring to FIG. 27, there is illustrated an alternative construction of dispenser substantially similar to the dispenser illustrated in FIG. 26. In this embodiment, there are two eddy current sensors. One of them consists of a pair of coils 20a and 20b and the other consists of a pair of coils 21a and 21b. Again, both sensors are enclosed within a shield 26.

Figure 28:
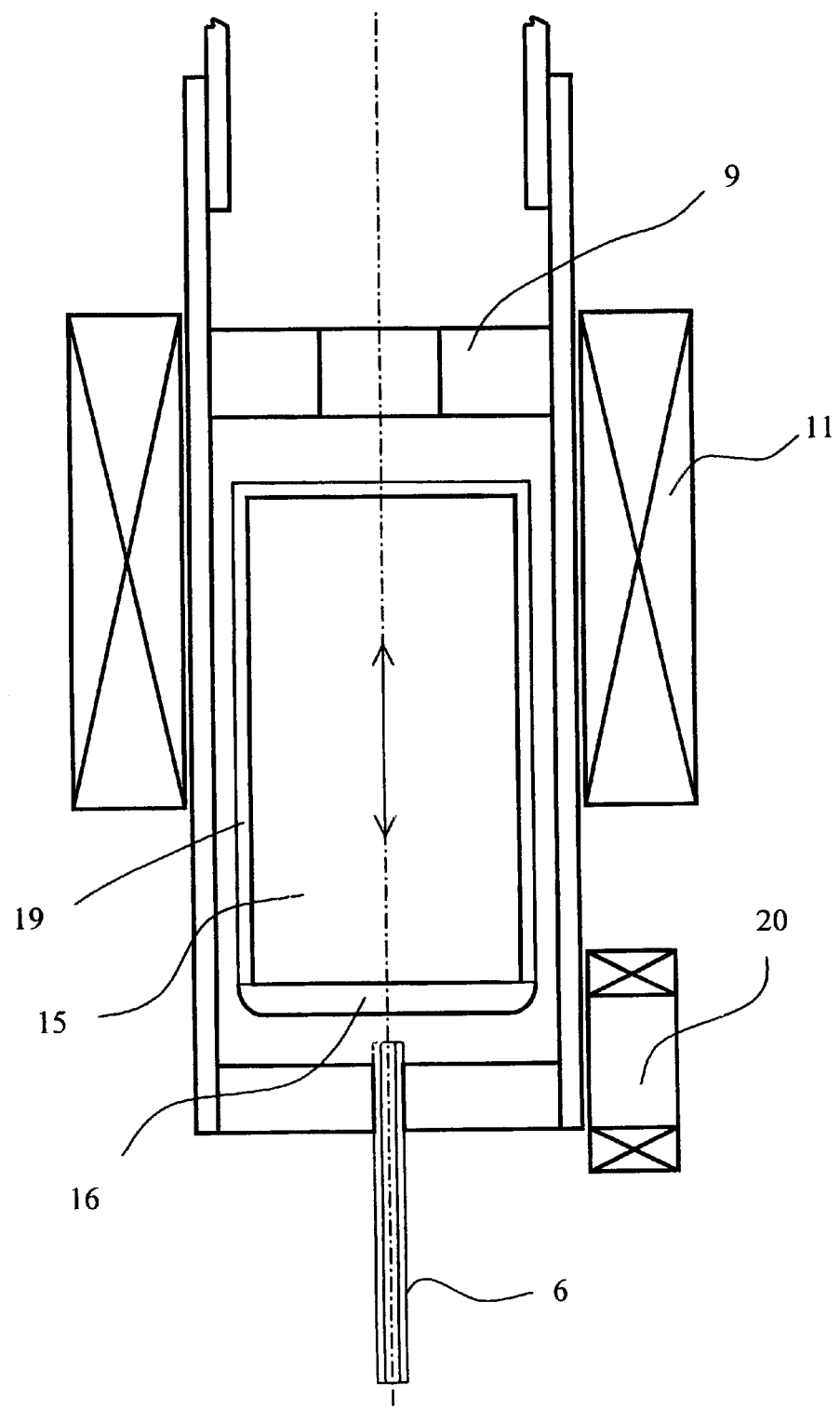
FIG. 28 is a view of a still further dispenser.

FIG. 28 illustrates another dispenser similar to the dispenser 27 except that there is one sensing coil 20 mounted on the side of the dispenser 1. Further, a conducting metal shield 19 encloses part of the boss 15.

Figure 29:
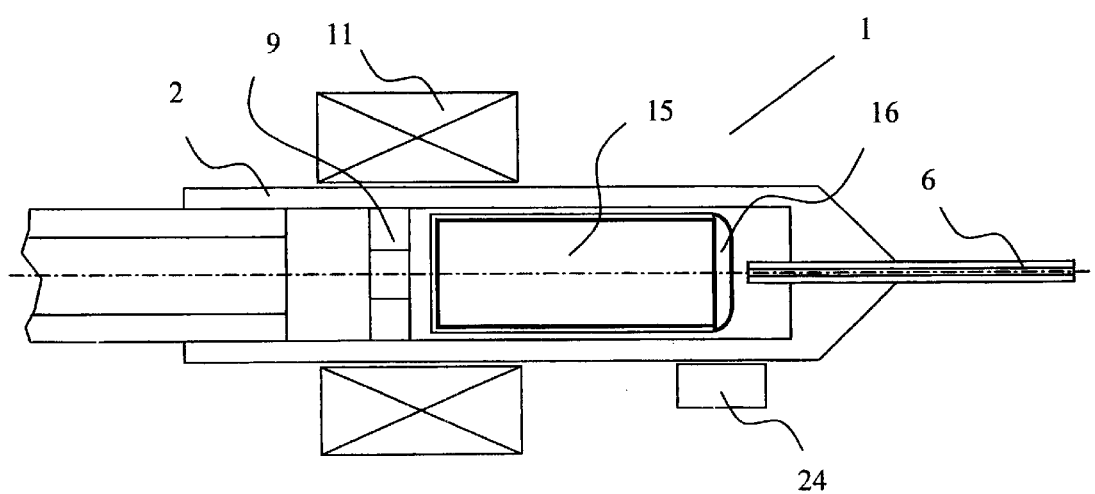
FIG. 29 is a view of a still further dispenser.

FIG. 29 illustrates a dispenser again identified by the reference numeral 1 and parts similar to those described with reference to the previous drawings are identified by the same reference numerals. The dispenser 1 uses a Hall sensor 24 for detecting the position of the valve boss 15. It could be advantageous to position the Hall sensor in such a way that it is relatively insensitive to the magnetic field generated by the actuating coil assembly and highly sensitive to the magnetic field of the moving boss. Not only the position, but also the rotational orientation of the Hall sensor with respect to the dispenser, can be used to minimize the magnetic field from the actuating coil assembly by comparison with the field from the boss as measured by the sensor.

It is important to appreciate that there are other types of sensors of magnetic field that could also be used for measurement of the position of the boss. These could be, for example, magnetoresistors, magnetodiodes, magnetotransistors, carrier-domain magnetic field sensors, surface acoustic wave sensors or other suitable sensors. The embodiment presented in FIG. 29 operates as follows. For calibration of the dispenser, the magnetic field corresponding to different positions of the boss as measured by the sensor, is recorded. It is clear this dependency will be different for a boss of a different material, shape or size. If the travel length between the boss in the fully closed and fully open positions of the dispenser is not significant by comparison with the length of the boss itself, one could measure magnetic field for the two extreme positions of the boss and use a linear approximation to work out the dependency of the field as a function of position. If the actuating coil assembly 11 produces a significant magnetic field at the Hall sensor, this contribution could be taken into account. For this purpose, the magnetic field signal due to the actuating coil assembly 11 is measured at different values of the current through the actuating coil assembly 11. During operation of the dispenser 1 the current through the actuating coil assembly 11 can be measured at any given instant. Therefore, the contribution resulting from the actuating coil assembly 11 can be readily subtracted from the total signal of the Hall sensor leaving just the contribution from the magnetic field of the boss. The signal from the sensor is compared with the desired signal for this instant. It can also be processed to work out the position of the boss at this instant. The current through the actuating coil assembly 11 can be then adjusted accordingly as described in the previous embodiments to ensure that the boss moves along the body member according to the desired schedule.

Figure 30:
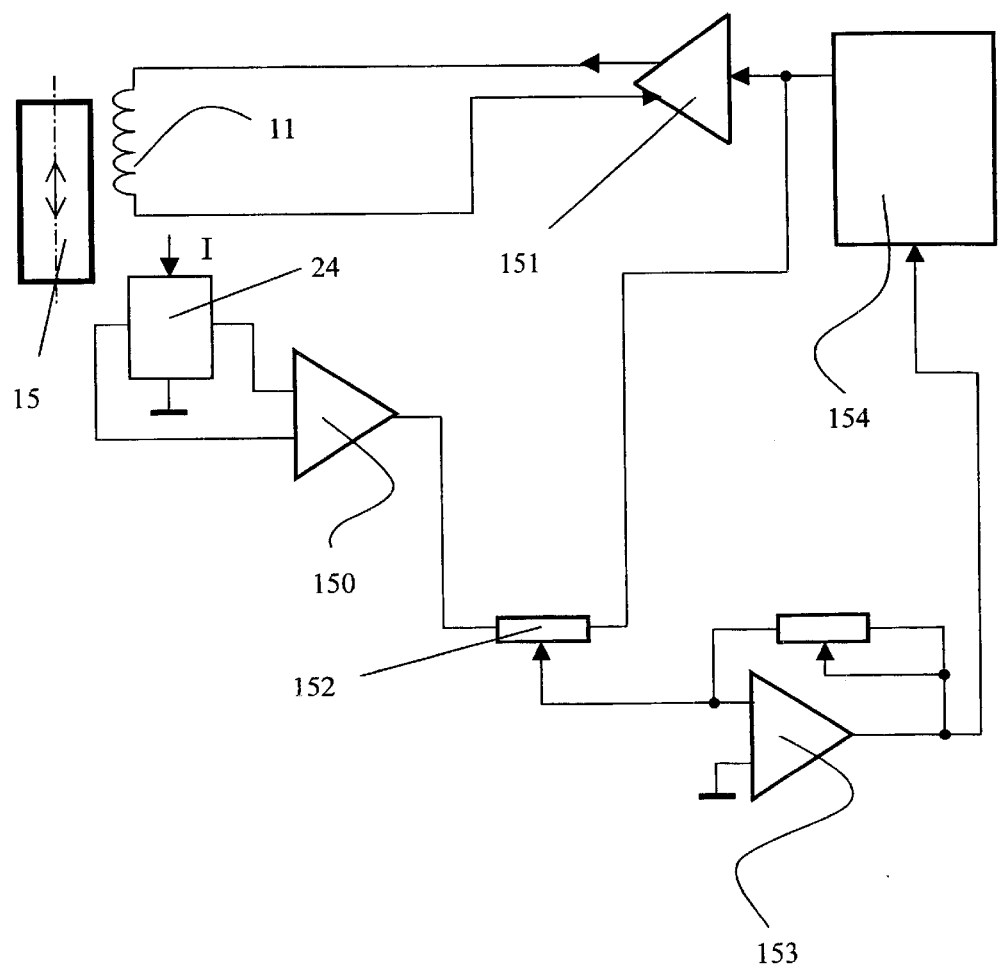
FIG. 30 is a block diagram of the controller of the dispenser of FIG. 28.

FIG. 30 shows a block diagram of the control of the dispenser of FIG. 29. A constant current is driven through the Hall sensor 24. A voltage signal generated at the Hall sensor 24 is amplified by the amplifier 150. A compensation signal is taken from the input of a power amplifier 151 and added to the output voltage from the amplifier 150 at a compensation potentiometer 152. After compensation, it is amplified again by an amplifier 153 and sent to a feedback controller 154. From the output of the feedback controller 154, the signal is supplied to the power amplifier 151 and then to the actuating coil assembly 11 to move the boss 15 in accordance with the required pattern of movement. It is advantageous that the power amplifier 151 functions in the current mode so that the output current (not voltage) depends on the input voltage/current. If this is not the case, the compensation signal will not be proportional to current through the actuating coil assembly 11 due to, for example, self-inductance of the actuating coil assembly 11. If the output current of the power amplifier 151 is not exactly proportional to the input signal (current/voltage), it is better to take the compensation signal from the output of the power amplifier 151 as in the circuit of FIG. 30 described below and not from its input. Adjustment of position of the compensation potentiometer 152 could be done in line with the calibration procedures described above.

Figure 31:
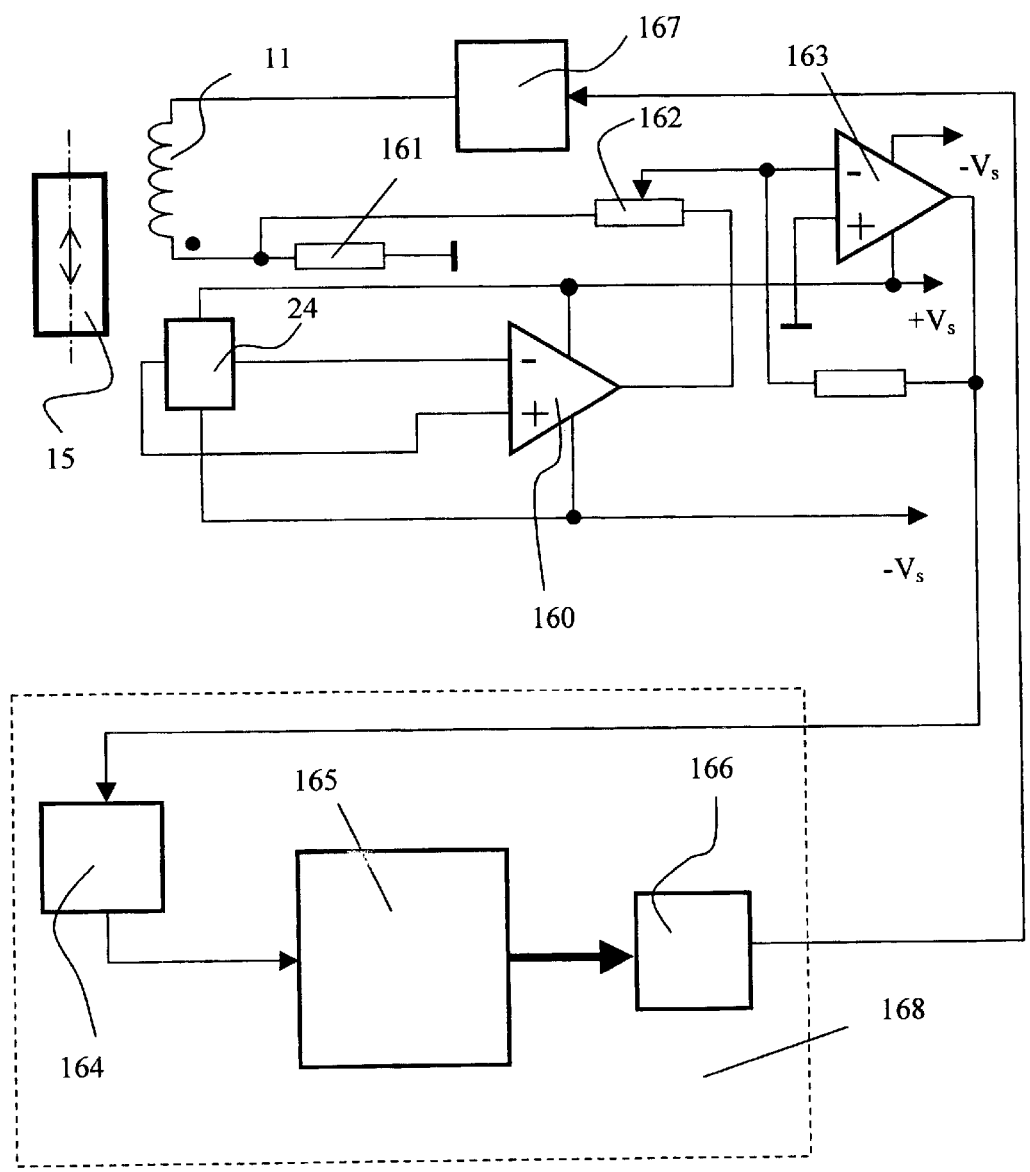
FIG. 31 is an electronic circuit used in the control of the dispenser of FIG. 28.

FIG. 31 shows schematically an example of electronic circuit for the control of dispenser presented of FIG. 29. A constant current is driven through the Hall sensor 24 as it is connected to $+V_s$ and $-V_s$ terminals. Voltage from the Hall sensor 24 is sent to an instrumentation amplifier 160. The magnetic field of the actuating coil assembly 11 at the Hall sensor 24 is proportional to the current through the actuating coil assembly 11. Therefore, the compensation signal is also proportional to the current through the actuating coil assembly. The purpose of the compensation is to offset any magnetic field induced in the Hall sensor directly by the actuation coil assembly 11. A voltage proportional to the current through the actuating coil assembly 11 is produced at a current resistor 161. The output voltage from the instrumentation amplifier 160 is added to the compensation voltage at a compensation potentiometer 162. After the compensation, the voltage is amplified by an operational amplifier 163. This voltage represents the magnetic field of the boss 15 detected by the Hall sensor 24 and therefore, is a function of the boss position. From the output of the operational amplifier 163 the voltage is supplied to the input of a feedback controller 168 consisting of an ADC 164, DSP 165 and DAC 166. From the output of the feedback controller the signal is supplied to a power amplifier 167 and then to the actuating coil assembly 11. At the output from the operational amplifier 163, one could also add an analog signal to offset the magnetic field produced by the boss at a well-defined position. For example, one could add a signal to compensate for the magnetic field of the boss 15 at the fully closed position of the valve. Then the ADC 164 would receive zero signal any time the dispenser is closed. Movement of the boss will result in a signal change at the input of the feedback controller. Alternatively, this compensation could be done directly at the feedback controller digitally as a part of the calibration routine.

Figure 32:
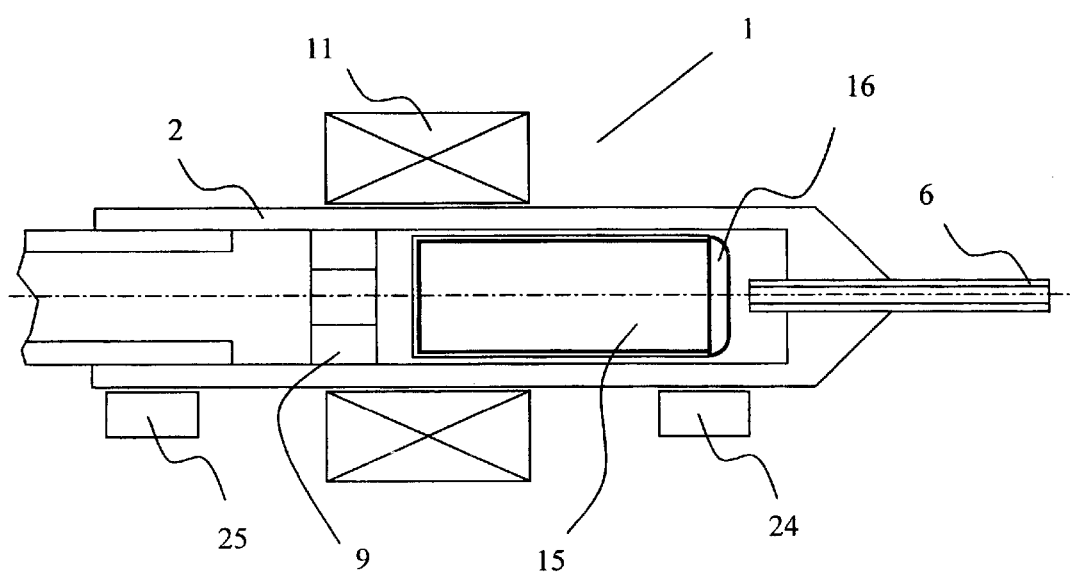
FIG. 32 is a view of another dispenser.

Referring to FIG. 32, there is illustrated an alternative construction of dispenser, again identified by the reference numeral 1 and substantially similar to the dispenser illustrated in FIG. 29 except that there are now two Hall sensors 24 and 25. Again, parts similar to those described with reference to the previous drawings are identified by the same reference numerals. The purpose of using two sensors is to cancel the magnetic field of the actuating coil assembly 11. To achieve this, the two sensors 24 and 25 are positioned at the same distance from the actuating coil assembly in such a way that one of them is positioned much closer to the boss than the other one. In this case the two Hall sensors 24 and 25 have comparable sensitivity to the magnetic field of the actuating coil assembly 11, and one of them is a lot more sensitive to the field of the boss 15. To compensate for the magnetic field of the actuating coil assembly 11, the difference between the two sensors 24 and 25 is measured. This difference is then due to the magnetic field of the boss. There may be provided a dispenser in which the two sensors are not identical and their distances from the actuating coil assembly 11 are not equal. Again other sensors of magnetic field, not based on Hall effect could be used such as, for example, magnetoresistors, magnetodiodes, magnetotransistors, carrier-domain magnetic field sensors, surface acoustic wave sensors or other suitable sensors.

Figure 33:
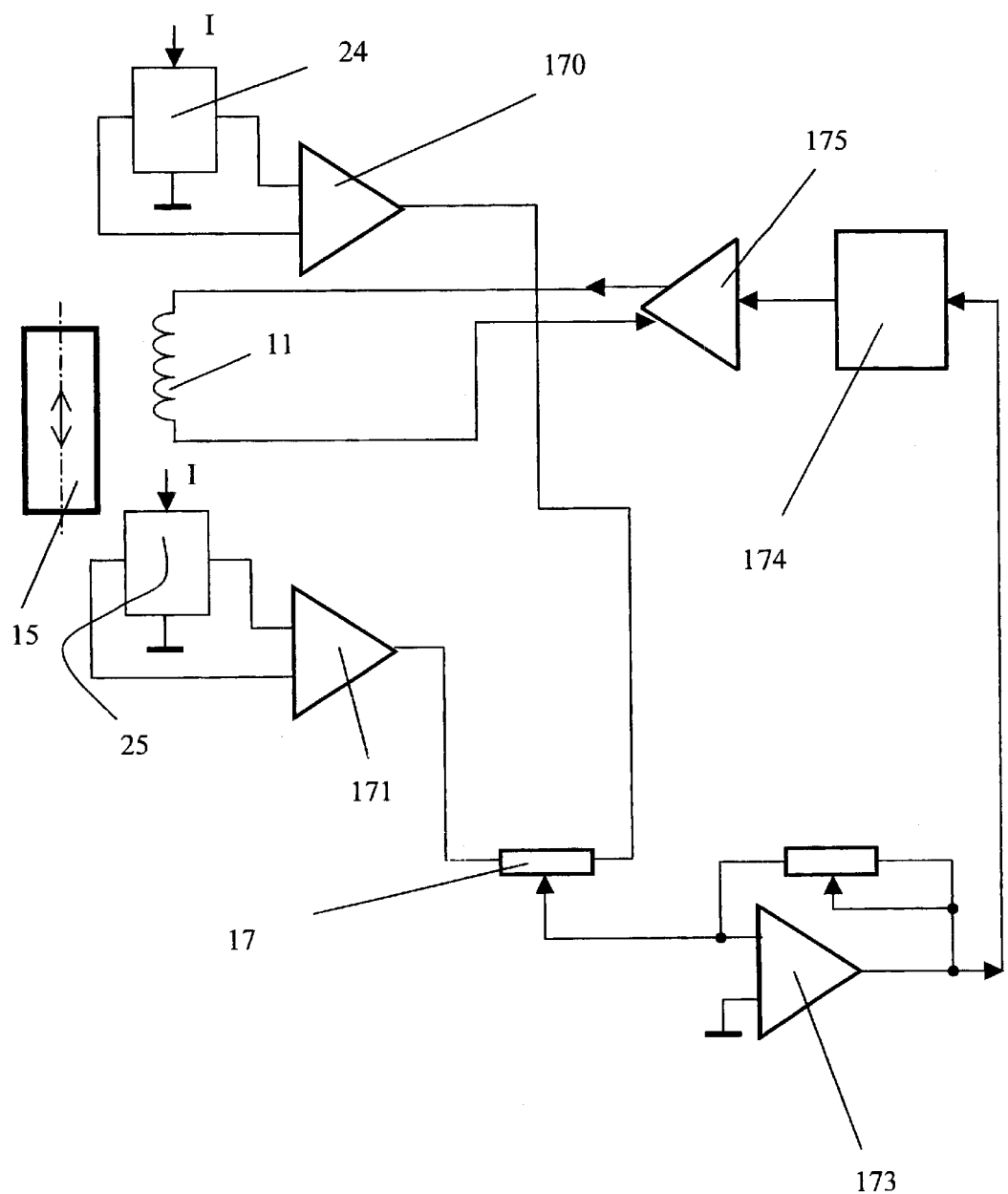
FIG. 33 shows, in block diagram form, a controller for the dispenser of FIG. 32.

FIG. 33 shows a block diagram of a controller for the dispenser shown in FIG. 32. A constant current is driven through the Hall sensors 24 and 25 A voltage signal generated at the Hall sensors 24 and 25, is amplified by amplifiers 170 and 171 respectively. After the amplifiers 170 and 171, the voltages are added at a compensation potentiometer 172. After the compensation, the signal is amplified again by an amplifier 173 and sent to a feedback controller 174. From the output of the feedback controller the signal is, as usual, supplied to a power amplifier 175 and then to the actuating coil assembly 11 to move the boss 15 in accordance with the required pattern of movement. Adjustment of the compensation potentiometer 172 could be done in line with the calibration procedures described above.

Figure 34:
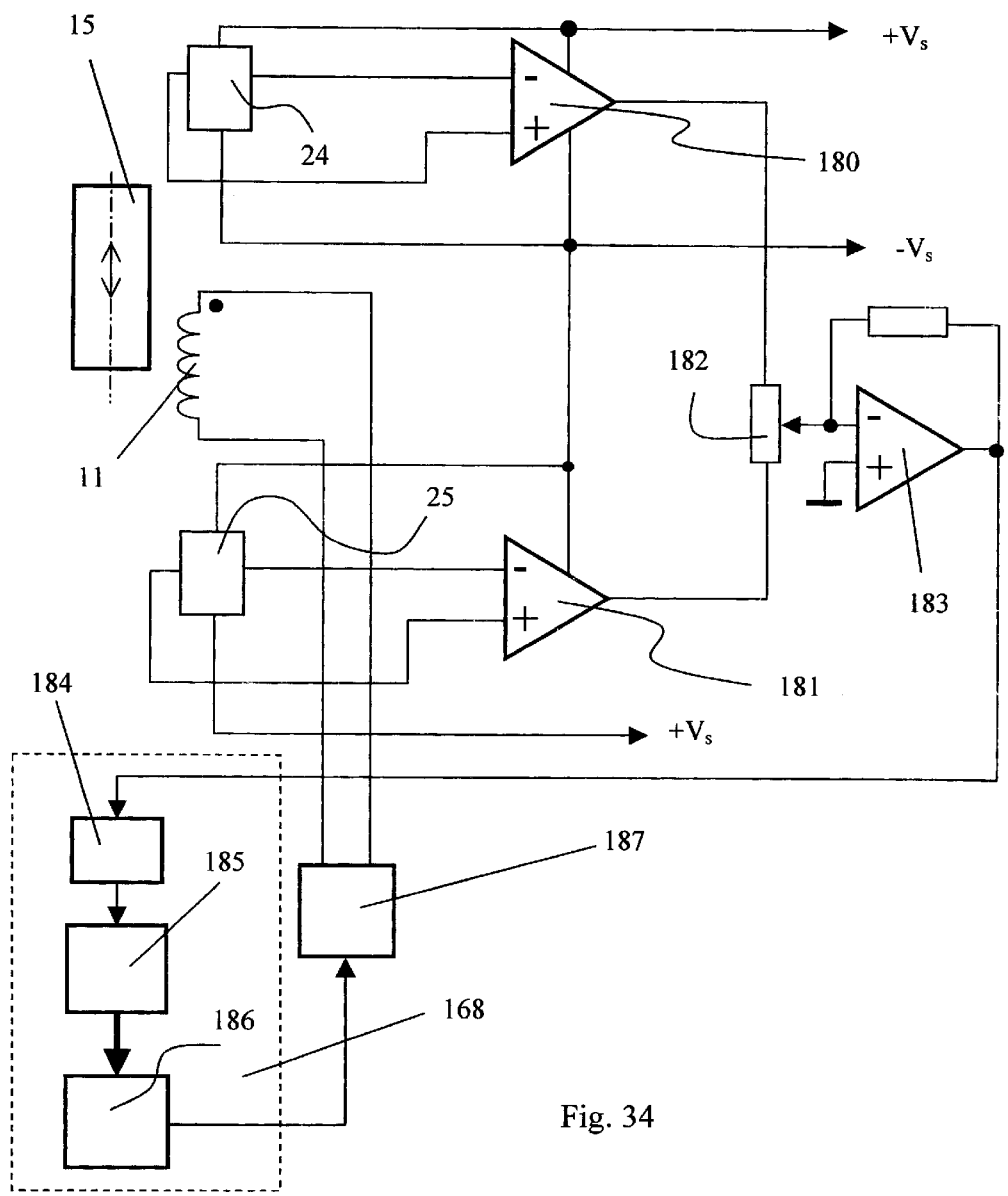
FIG. 34 illustrates another electronic circuit forming control means of the dispenser of FIG. 32.

FIG. 34 illustrates an electronic circuit forming control means for the dispenser of FIG. 32. The Hall sensors 24 and 25 are supplied with a constant current through the terminals $+V_s$ and $-V_s$. The signals induced in the sensors are supplied to the amplifiers 180 and 181 respectively. The amplifiers 180 and 181 are instrumentation amplifiers. Then the signals are added together on a compensation potentiometer 182 and amplified by a further amplifier 183. From the output of the amplifier 183, the voltage is supplied to the input of a feedback controller 168 consisting of an ADC 184, DSP 185 and DAC 186. From the output of the feedback controller the signal is supplied to a power amplifier 187 and then to the actuating coil assembly 11. If the polarities of the signals generated by the Hall sensors 24 and 25 are incorrect, one of the sensors could be reconnected so that the direction of the current in it is reversed. If the two Hall sensors are not identical or not located at the same distance from the actuating coil assembly, this can be corrected by means of adjusting the gain of the amplifiers 180 and 181 and compensation potentiometer 182. These could be calibrated/adjusted as follows. Suppose the boss is made of a permanent magnetic material with low permeability. Then the presence of the boss would not change the magnetic field of the actuating coil assembly 11 but rather superimpose on it. To cancel the magnetic field of the actuating coil assembly 11, the boss 15 is removed from the dispenser tip. A constant current is supplied through the actuating coil assembly 11 and this produces a voltage in the two sensors. The gain of each of the amplifiers 180 and 181 is adjusted in such a way that their output voltages have approximately equal values. Then the by adjusting the compensation potentiometer 182, the signal at the output of the amplifier 183 is set to zero.

When sensing coils are used, they may be located outside the body of the dispenser. Many positions can be readily found. Clearly, any arrangement with a multiplicity of coils positioned outside the sensor can be readily easily devised. They could, for example, also operate as a variable inductance sensor as described above or indeed could function using a parametric oscillator.

The principle of using a parametric oscillator as a boss position sensor is such that the boss is coupled to at least one element of the oscillator circuit and therefore changes the oscillator's operation as it moves. For example:

(i) The moving boss can change the effective inductance $L_{res}$ of the inductor forming a part of the oscillator's resonator. Then, in response to the boss movement, the frequency of the oscillator changes as it is determined by the value of the inductance included in the resonator. Within common approximation that can be found in conventional textbooks on electronics, the resonance frequency of the oscillator is determined by the formula $$f_{res}=1/(2*\pi*(L_{res}*C).$$

The value of the inductance $L_{res}$ can change due to, for example, magnetic permeability of the boss. If the boss has a considerable magnetic permeability, the inductance of the coil changes when the boss is displaced in the vicinity of the resonator's coil. The value of inductance can also change due to eddy current being induced in the boss. By bringing a conducting object to an inductor and by inducing a pattern of eddy current in the object, one can change the effective inductance of the inductor. This is a consequence of the fact that the pattern of eddy current then changes the pattern of AC magnetic field around the inductor. As the boss moves in the vicinity of the resonator's inductor coil, the pattern of eddy current and therefore inductance of the inductor coil, change. To sense the change, the oscillator's resonator must have inductive coupling with the dispenser and boss inside it, i.e. coupling through the AC magnetic field of the resonator/coil.

(ii) The moving boss can also change the capacitance of some elements of the oscillator's circuit. This effect can be exploited more readily at a high frequency, say above 1 GHz, but not exclusively. This change is due to the fact that the dielectric constant of the boss is different from that of the dispenser and the liquid inside it. To sense the change, the oscillator's resonator must have capacitive coupling with the dispenser and the material inside it, i.e. coupling through the AC electric field of the resonator.

(iii) As the boss is displaced, the quality factor of oscillator's resonator can change. This change can primarily result from three sources.

Firstly, the imaginary part of the dielectric constant of the media in the vicinity of the resonator can change as a result of the boss movement. The imaginary part of the dielectric constant is directly related to dielectric losses in the resonator. This change is due to the fact that the dielectric properties of the boss are different from the ones of the dispenser and the liquid inside the dispenser. For example, water can result in significant dielectric losses especially at frequencies above 1 GHz. Therefore, if the boss is made of a material having dielectric losses lower than those of water, the overall losses increase as the boss moves and the space in the vicinity of the sensitive element of the resonator is filled with a water-based sample liquid. For example, with the sensor adjacent the valve seat and the valve boss sitting on the valve seat, there will be one type of dielectric loss. However, when the valve boss is raised off the valve seat, then the overall dielectric loss is increased. Dielectric losses are also commonly characterised by the loss tangent defined as the ratio of imaginary and real parts of the dielectric constant. It is advantageous to design the boss in such a way that its dielectric losses are in contrast to the values for the dispenser and liquid filling the dispenser. To sense the change in the dielectric constants caused by the moving boss, the oscillator's resonator roust have capacitive coupling with the dispenser, i.e. coupling through the AC electric field of the resonator. The methods of capacitive coupling between microwave strip lines and dielectric resonators are described in various texts.

The second reason for the change in the quality factor of the oscillator is that, as the boss is displaced, the losses due to magnetic permeability of the media in the vicinity of the oscillator's resonator can change. As indicated below the boss can be readily fabricated in such a way that it has a significant magnetic permeability especially at frequencies below 100 MHz. Therefore, it can have a significant imaginary component of magnetic permeability that is responsible for the magnetic losses in AC magnetic field. In the same way as with the dielectric losses, the magnetic losses are described by the tangent of magnetic losses given by the ratio of imaginary and real parts of magnetic permeability. To detect the change in the quality factor of the oscillator due to the magnetic permeability of the boss, the oscillator's resonator must be inductively coupled with the dispenser, i.e. coupled through the AC magnetic field of the resonator. The general theory of losses due to magnetic permeability in magnetic materials is explained in numerous text books. The data on the high frequency magnetic losses are available similarly in the literature.

The third reason why the quality factor can change as a result of the boss displacement, is because of the losses due to eddy current in the boss. These depend on the electrical resistance of the boss. The nature of these losses is easy to understand. The AC field of the resonator induces AC current in the boss resulting in the ohmic losses of energy. As the position of the boss changes, the ohmic losses will also change. If the resistance of the boss material is high, it may be advantageous to coat the boss with a layer of material with high conductivity such as copper or aluminium. It may be advantageous to then coat this layer of material with high conductivity with second layer of chemically resistant coating to achieve the chemical inertness of the boss.

These changes can result in changes in the frequency of the oscillator. The changes in capacitance C and inductance $L_{res}$ of the oscillator can result in a change in resonance frequency as these are involved in the formula:

$$f_{res}=1/(2*\pi*(L_{res}*C)^{1/2})$$

describing the frequency of oscillations in a lossless oscillator. The changes in the quality factor $Q_{res}$ of the resonator can also result in changes of the oscillators frequency. Within an approximation, the frequency of an oscillator with losses is given by a formula:

$$f_{osc}=f_{res}*(Q_{res}^2+1)/Q_{res}^2.$$

Figure 35:
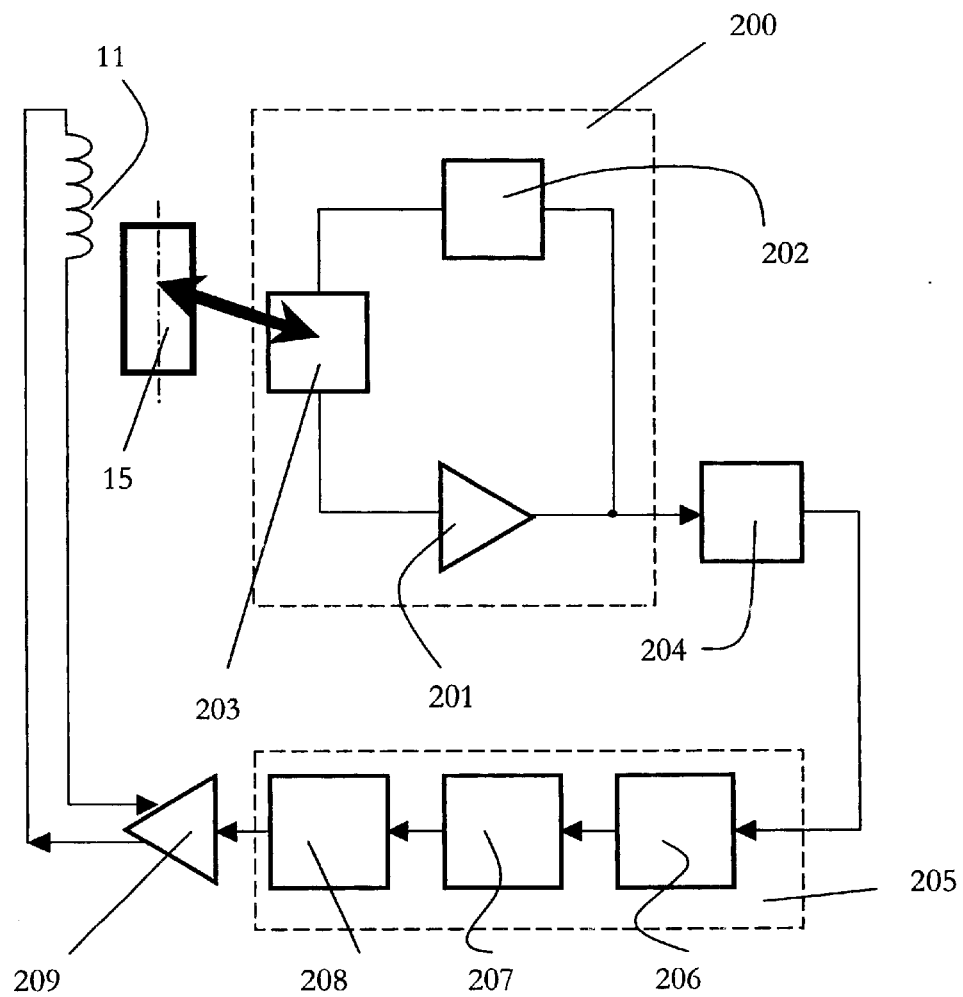
FIG. 35 is a circuit for a parametric oscillator.

Here $Q_{res}$ is the quality factor of oscillator circuit. The theory of oscillators can be found in the literature. By measuring the oscillator's frequency one can detect the position of the boss. The changes in $Q_{res}$ can also change the amplitude of oscillations or power consumed by the oscillator. Referring to FIG. 35, there is illustrated a parametric oscillator, identified generally by the reference numeral 200, delineated by interrupted lines. The parametric oscillator 200 comprises an amplifier 201, a nonlinear element 202 and a resonator 203. The resonator 203 is coupled to the boss 15 by electromagnetic coupling, as shown schematically by a two-sided thick arrow. The frequency of the oscillator 200 which is dependant on the position of the boss is measured using a frequency-to-voltage converter 204. Therefore, the output of the frequency-to-voltage converter 204 contains information about the movement and thus the current position of the boss. Then the signal is sent to a feedback controller indicated generally by the reference numeral 205, again surrounded by interrupted lines, and comprising an ADC 206, DSP 207 and DAC 208 in the same way as in many previous embodiments described above. After that, the signal is sent to a power amplifier 209 and then to the actuating coil assembly 11. The controller can be calibrated using a routine similar to the ones described above. For example, frequency of the oscillator could be measured for two positions of the boss: boss pressing against the valve seat and boss pressing against the stopper. Then the linear approximation could be employed to work out the position of the boss using the frequency readout. The frequency-to-voltage converter 204 could be substituted by a frequency counter. Indeed, many other circuits could be provided.

In this circuit it is not fundamentally important to determine which of the factors described in detail above results in the change of the frequency of the parametric oscillator. It could well happen, that more than one factor is responsible. For example, the value of the quality factor $Q_{res}$ could change due to the eddy current losses and also due to the magnetic losses. Possibly in addition to this, the value of inductance $L_{res}$ or capacitance C could also change. In practice one of the factors will usually dominate depending on the materials used, the type of resonator and the type of coupling between the resonator and the boss. In practice it is not always necessary to know exactly the reason causing the change in the frequency. The most important point is to relate the frequency change with the position of the boss. This can be done by calibration and this information is then introduced in the feedback controller.

It is important to appreciate that not only frequency but also amplitude of the oscillations can depend on the position of the boss. The amplitude of the oscillations can also depend on the values of inductance and capacitance, namely, $L_{res}$ and C, and the quality factor $Q_{res}$ of the oscillator.

Figure 36:
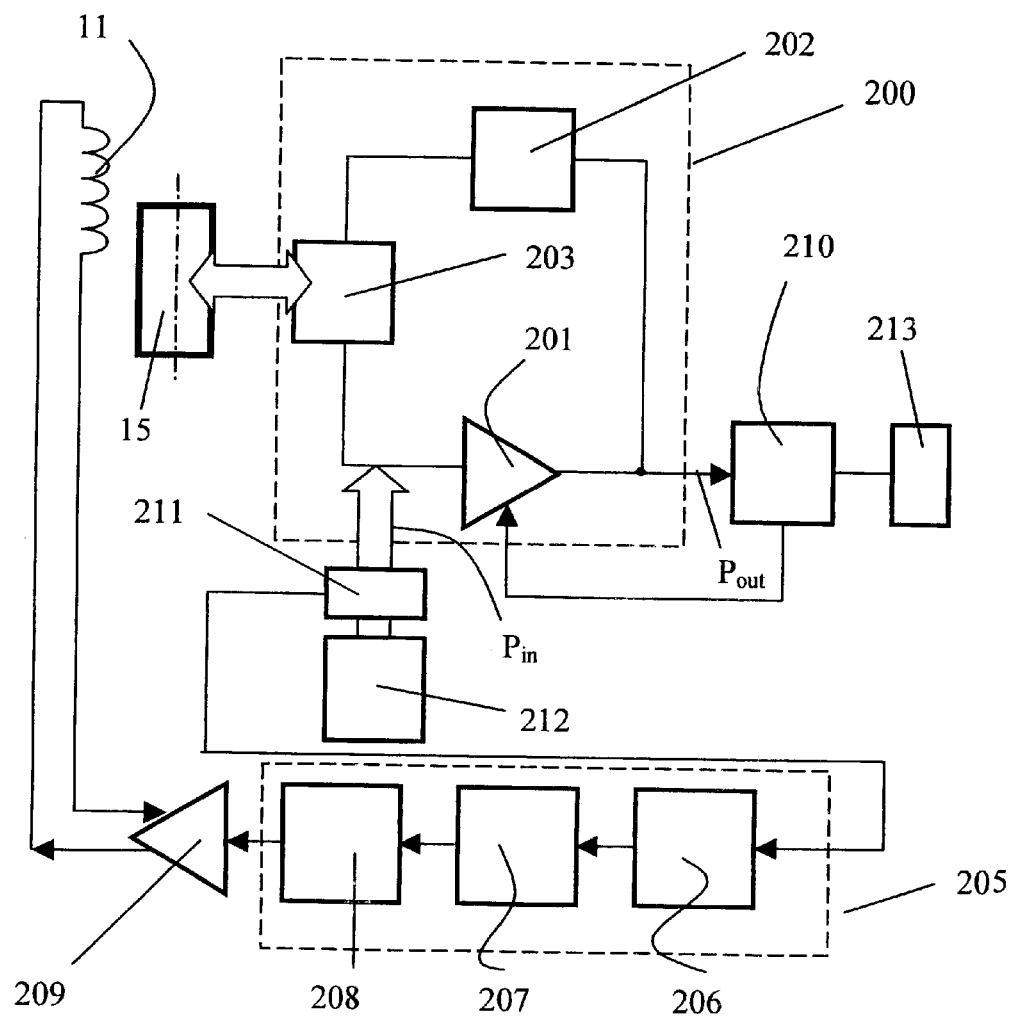
FIG. 36 is another parametric oscillator circuit.

This principle is used in the embodiment of FIG. 36. In this embodiment, there is illustrated a parametric oscillator, again identified by the reference numeral 200 and a feedback controller, indicated generally by the reference numeral 205. All perform the same functions as in the embodiment of FIG. 35. The parametric oscillator 200 consists again of the amplifier 201, the non-linear element 202 and the resonator 203. The difference is in the operation of this embodiment in that instead of measuring the frequency of the oscillator, the output power $P_{out}$ of the oscillator is kept constant. This is done by measuring the output voltage/power of the oscillator with an AC-to-DC converter or power meter 210 and by sending the feedback signal to the amplifier 201 of the oscillator 200 to adjust its gain accordingly to keep the power of the oscillator constant. If the quality factor Q of the oscillator changes and its output power $P_{out}$, is kept constant, the power supplied from a power source 212 into the oscillator $P_{in}$, changes. Therefore, the power level $P_{in}$ measured by a power meter 211 depends on the position of the boss. The output voltage/current from the power meter 211 is sent to the feedback controller 205 in the same way as in the previous embodiments. The power meter 210 couples into a matched load 213 to avoid reflection of power back into the oscillator.

One could design numerous other circuits of dispenser controllers using the same principle of change in the power generated by the oscillator. For example the output power does not have to be kept constant. Instead one can measure the level of output power from the oscillator. The change in the power level generated by the oscillator in response to change in the parameters of the resonator is usually greater if the oscillator is tuned in such a way that gain of the amplifier included in the oscillator is only marginally above the critical value that is required for a stable generation of AC voltage.

Depending mainly on the coupling between the actuating coil assembly and the resonator but also on other factors such as type of the parametric oscillator, material and shape of the boss, the controller of FIG. 35 may require a compensation circuit. The reason is that the rapidly changing magnetic field of the actuating coil assembly could also influence the parametric oscillator. In particular it could affect the output power of the oscillator. This can be readily corrected using, for example, the same approach as in some previous embodiments described in this document. For example, two identical oscillators can be positioned at the same distance from the actuating coil assembly in such a way that they are both equally sensitive to the magnetic field of the actuating coil assembly and yet one of them is more sensitive to the boss than the other one. Then the power levels generated by the two oscillators can be compared and difference signal between the two power levels can be sent to the feedback controller. These dispensers are not included in the document, as this would increase its size without adding new information.

Figure 37:
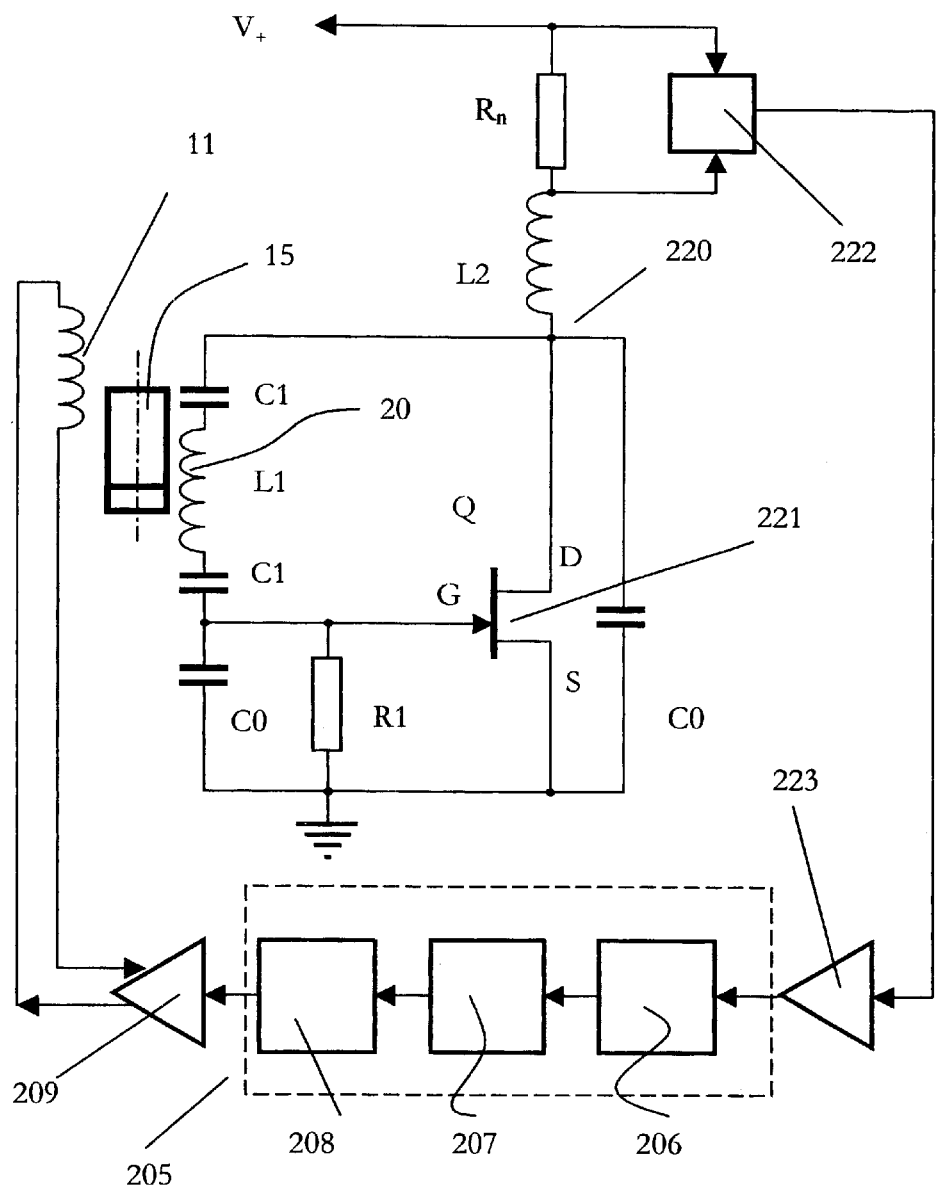
FIGS. 37 to 39 are various circuits of a controller using parametric oscillators.
Figure 38:
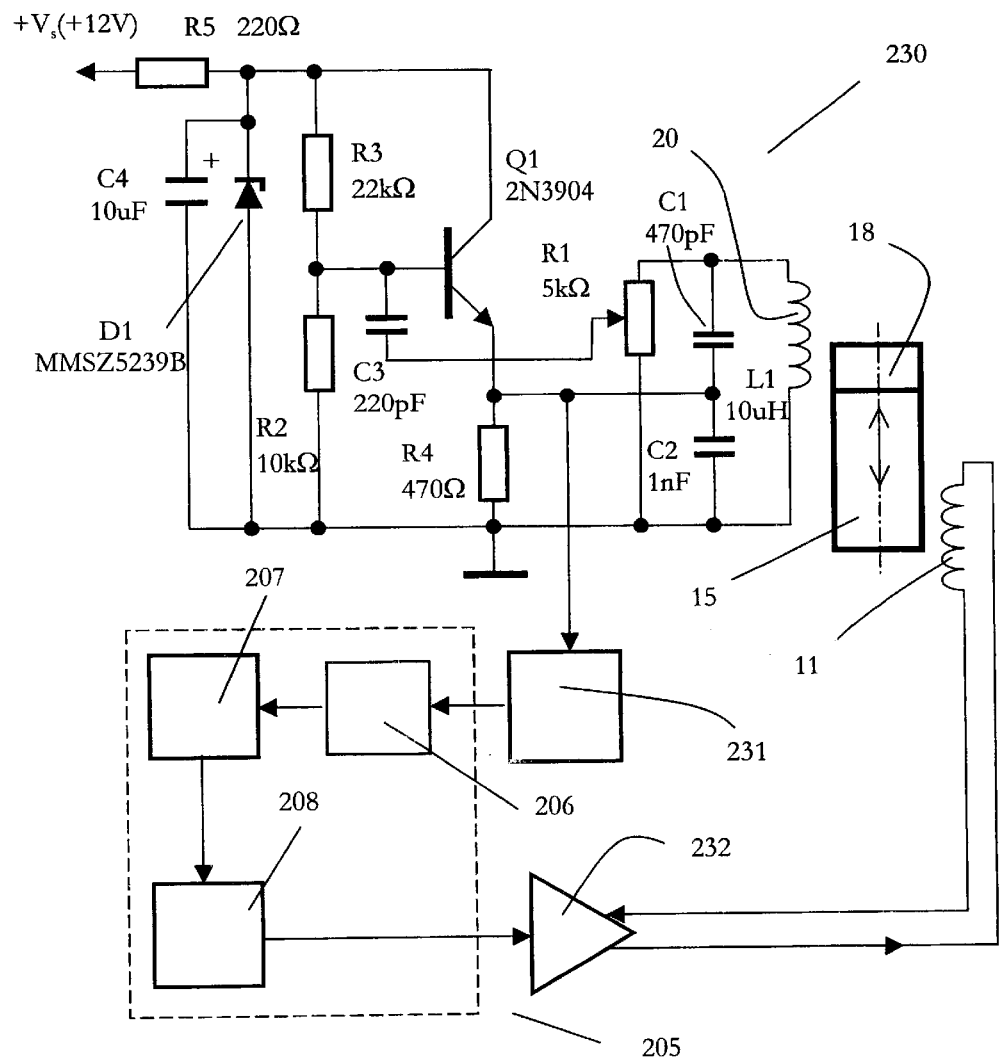
Figure 39:
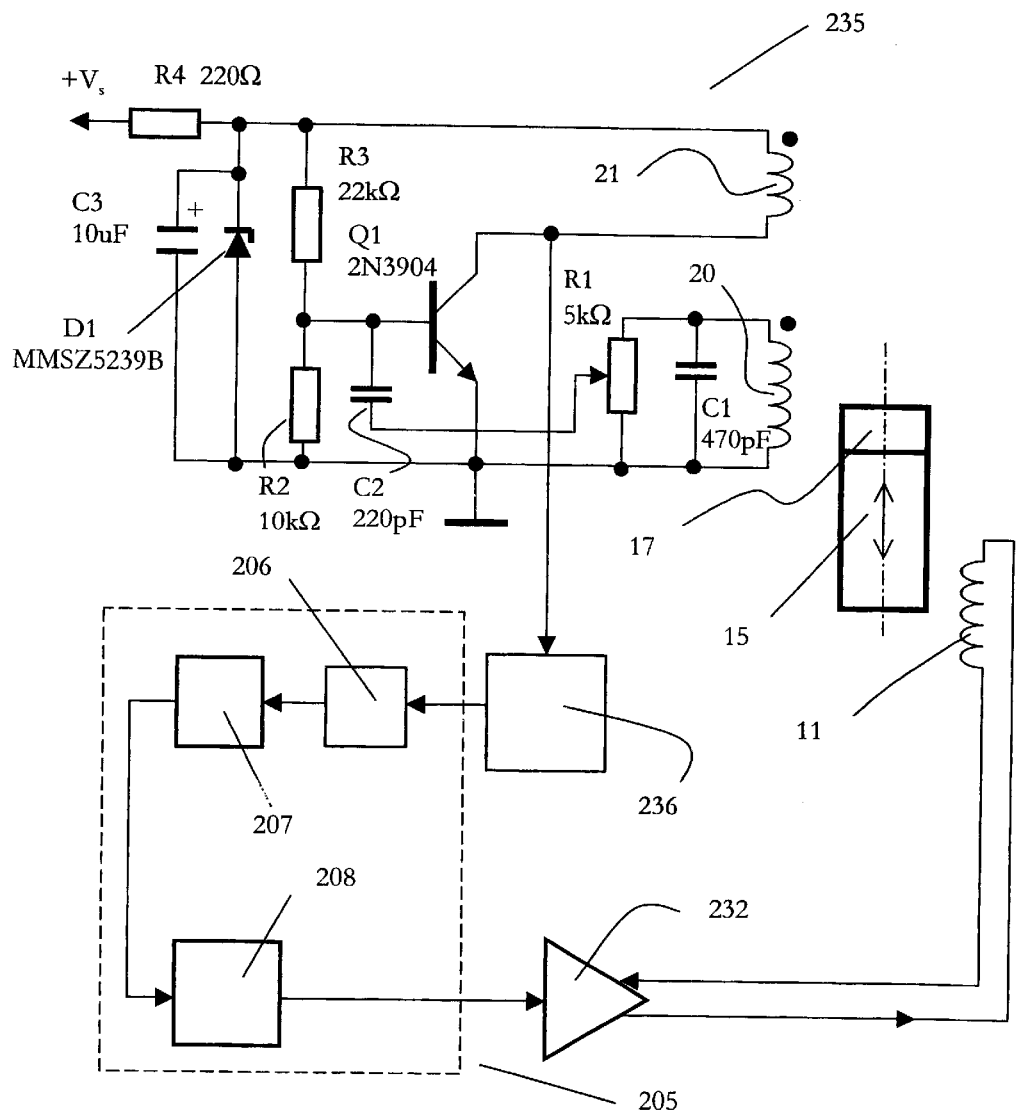

FIGS. 37, 38 and 39 show some examples of the circuits of controllers using parametric oscillators. Numerous other examples can be readily developed by those skilled in the art of electronics. For example, the circuit can be built around well-known types of oscillators to include a Hartley oscillator, a Colpitts oscillator, a Clapp oscillator, a Pierce oscillator, a tuned input-tuned output oscillator, an RC phase shift oscillator, a Wien bridge oscillator, a stable multivibrator, or a crystal oscillator. Detailed description of these oscillators can be found in the literature.

FIG. 37 illustrates another embodiment of controller. The circuit of the boss position sensor is based around a standard Colpitts high-frequency oscillator, indicated generally by the reference numeral 220, with the resonance circuit connected between the drain and gate of a GaAs MESFET transistor 221. Other parts of the circuit similar to those described with reference to FIGS. 33 and 34 are identified by the same reference numerals. The resonance circuit consists of inductor L1 and two capacitors C1. The oscillation frequency can be selected by tuning the values of L1 and C1. The oscillation frequency also depends on the quality factor $Q_{res}$ of the resonance circuit that is given by the formula:

$$Q_{res} = \omega * L1/R1,$$

Where ω is the oscillation frequency and R1 is the value characterising the losses in the resonance circuit that in turn is dependent on the active resistance of the coil, imaginary components of electric and magnetic susceptibility of the boss if it is coupled to the resonator. A resistor Rn with the value of some 10 to 100 Ohm and a small choke inductor L2 help to achieve a more stable operation of the oscillator. The resistor R1 with the value of some 100 kΩ is installed to achieve the voltage biasing on the gate of the MESFET 221. Good operating conditions are achieved for the value of $V_+$ between 1.7 and 2.1 V. We have found that good sensitivity to the boss movement is achieved for the frequency of the oscillator in the range of 2 to 4 GHz. This does not exclude operating at other frequencies. In this circuit, the amount of power consumed by the circuit depends on the quality factor $Q_{res}$. This power is taken from the voltage source $V_+$ and the power level is measured using a power meter 222. Since the quality factor of the resonance circuit depends on the position of the boss, the output from the power meter 222 is also an indication of the boss position. The output from the power meter 222 is amplified by an amplifier 223 and then connected to the feedback controller 205 in the same way as in many previous embodiments.

We have found that the following values result in a suitable operation of the circuit: $C_0$ is 40 to 60 picoFarad, C1 is 2 to 3 picoFarad, L1 is 3 to 6 nanoHenry. The active resistance of the resonator circuit of some 0.2 to 0.4Ω results in a stable detection of the boss movement. The coil 20 consists of only 1 to 3 windings of copper wire. The coil 20 diameter is 1 to 3 mm. Alternatively it is made on a standard substrate for making microwave PCB boards. The size of the boss is in the same range as in the previous embodiments: it is a cylinder with the diameter of 1 to 3 mm and the length of 5 to 10 mm. The coil 20 is mounted facing the lower end of the dispenser and is brought close to the body of the dispenser.

FIG. 38 shows another circuit of the controller. Again, elements already illustrated in FIG. 34 are identified by the same reference numerals. It is based on an oscillator 230 whose frequency depends on the value of inductance L1 of one sensing coil 20. The resonance contour consists of inductance L1 and capacitors C1 and C2. The oscillator 230 is based on the transistor Q1. The gain of the oscillator is determined by the potentiometer R1. As the boss position is changed, the inductance value L1 changes due to magnetic permeability of the boss and also the eddy current induced in the boss. The frequency of the oscillator is measured using a frequency-to-voltage converter 231 and then sent to the feedback controller 205 consisting of the ADC 206, DSP 207 and DAC 208. Then the signal is sent to a power amplifier 232 and then to the actuating coil assembly 11. This controller can work with several embodiments of the dispensers already described.

FIG. 39 shows another embodiment of the dispenser using an oscillator 235 with two sensing coils 20 and 21. Again, parts similar to those described with reference to FIG. 37 are identified by the same reference numerals. In this dispenser, the mutual inductance between the sensing coils 20 and 21 depends on the position of the boss 15. To increase the mutual inductance, the marker 17 of a soft magnetic material with high permeability is attached to the boss. The controller uses the oscillator 235 built around a transistor Q1 and sensing coils 20 and 21. The inductive coupling between the coils 20 and 21 determines gain of the circuit. Therefore the gain of certain minimum value is required to achieve stable oscillations. A potentiometer R1 also determines the gain of the circuit. The frequency of the oscillations is determined by the resonance contour consisting of the sensing coil 20 and capacitor C1. If the position of the potentiometer R1 is chosen correctly, the amplitude of the oscillations depends on the inductive coupling between the sensing coils 20 and 21. The amplitude of the oscillations is measured by using an amplitude detector 236. Then the rectified signal is sent to the feedback controller 205 as in many previous embodiments. During the calibration of the circuit, the potentiometer R1 should be set to such a position, in which movement of the boss between the fully open and fully closed dispenser results in a significant change in the amplitude of the oscillations and yet, the oscillator produces a stable oscillation signal. Therefore, the sensitivity of the circuit may need to be compromised to achieve better robustness of the oscillator. Alternatively, the frequency of the oscillations could be measured. In this case a frequency-to-amplitude converter could be used instead of the amplitude detector.

As suggested already, the actuating coil assembly can comprise two assemblies. The two actuating coil assemblies can be actuated simultaneously in anti-phase, one of them pushing the boss and the other pulling it. Similarly, they can be connected in series or in parallel.

Figure 40:
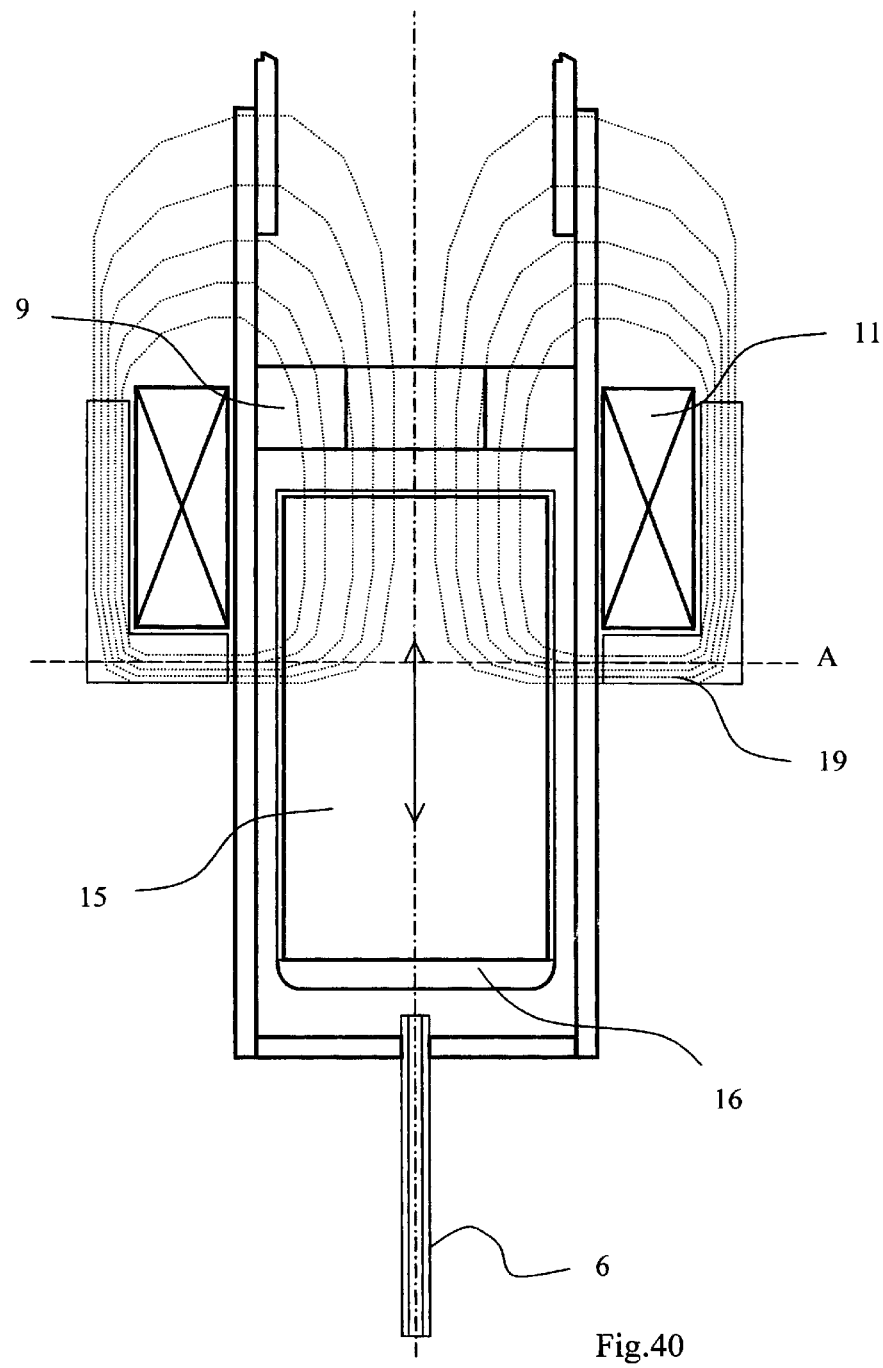
FIG. 40 illustrates an alternative construction of dispenser.

FIG. 40 shows an embodiment of actuating coil assembly again identified by the reference numeral 11 and parts similar to those described with reference to the previous drawings are identified by the same reference numerals. In this embodiment, the actuating coil assembly 11 is provided with a shield 19 of a soft magnetic material. This creates a magnetic field with a strong gradient at the location A. As the force acting on a permanent magnetic material placed in a magnetic field is proportional to the gradient of the magnetic field, increasing the gradient can increase the force. Using a shield with high permeability around the actuating coil is likely to change the inductance of the coil. Therefore, this may require changes in the actuating coil controller. It is important to appreciate that this embodiment of the actuating coil assembly 11 can be used with a number of different embodiments of the sensor of position of the boss.

Figure 41:
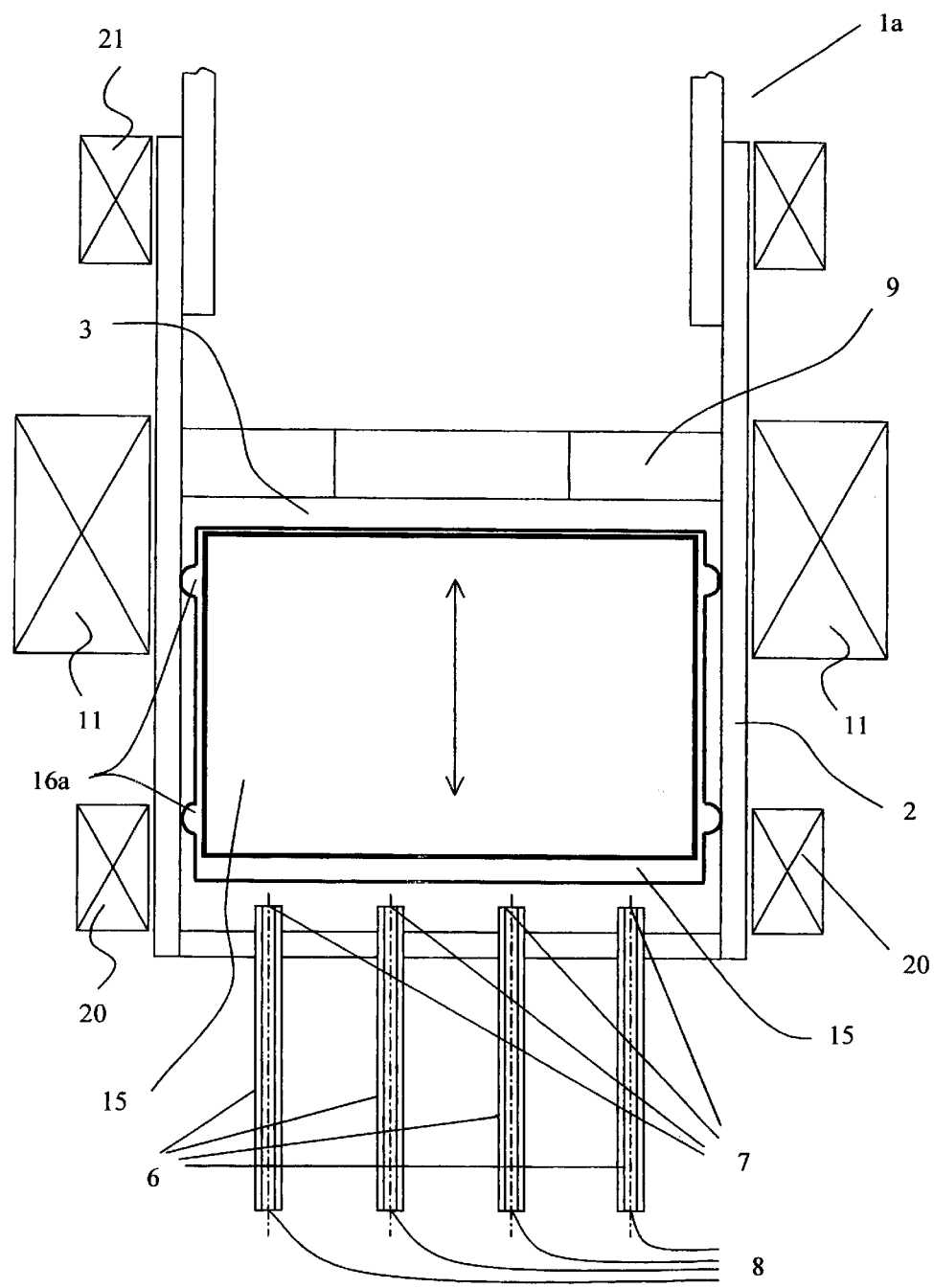
FIG. 41 illustrates a still further dispenser according to the invention.

Referring to FIG. 41, there is illustrated an alternative construction of dispenser, indicated generally by the reference numeral 1a, which dispenser has a plurality of nozzles 6. The dispenser 1a may be substituted for the dispenser 1 in any of the embodiments. In this embodiment, the boss 15 is provided with optional rims 16a in its soft polymer coating 16 to form a reasonably close fit within the main bore 3. To allow the flow of liquid to bypass the boss 15, the boss 15 could have holes in it or longitudinally arranged channels or grooves to permit the passage of liquid therebetween.

Figure 42:
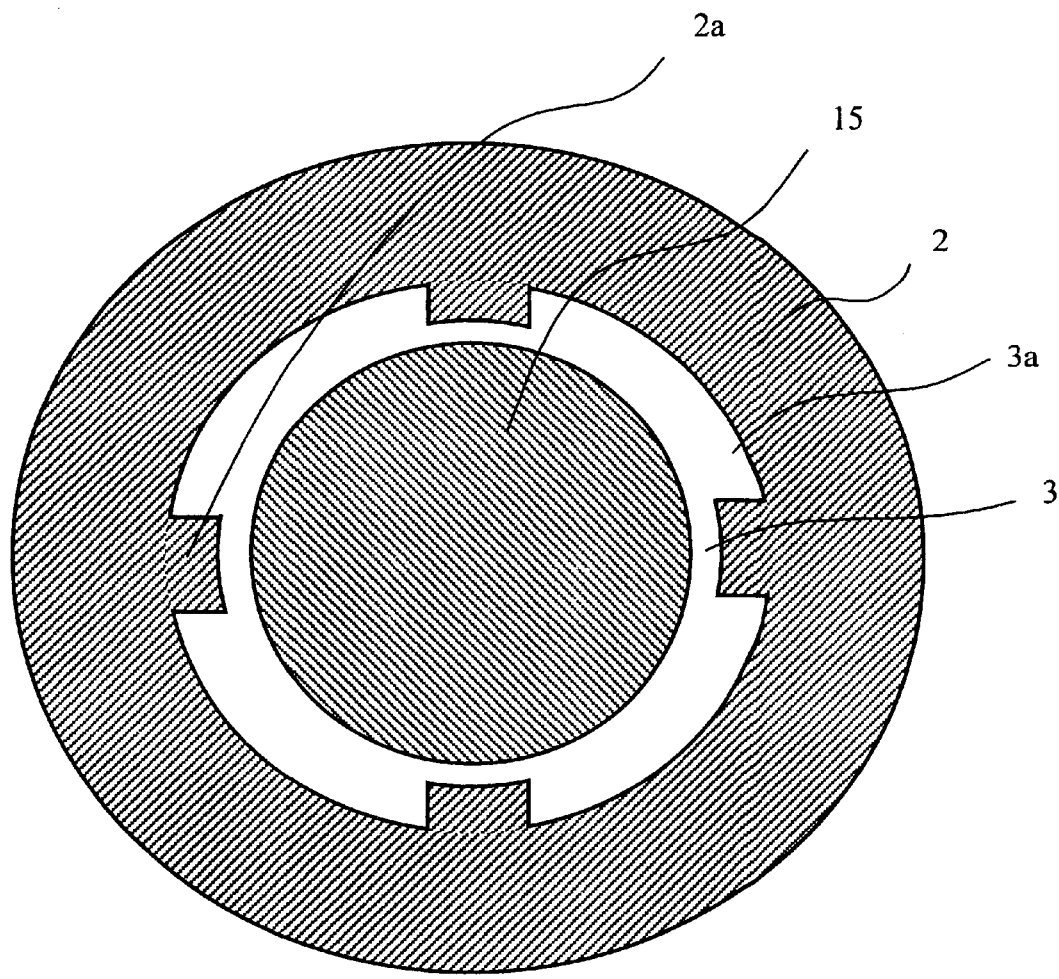
FIG. 42 is a cross section through another dispenser.

FIG. 42 shows in cross section a cylindrical boss 15 within a metering valve body 2 incorporating a plurality of channels 3a within the main bore 3 formed by ribs 2a in the valve body 2. The purpose of the channels is to increase the cross sectional area through which liquid in the dispenser can be displaced during movement of the boss 15. This increase leads to a reduction in the viscous force acting on the boss and as a result allows for its faster movement. In a typical such embodiment, there are four channels with the depth of 0.4 mm and width of 1.2 mm for the boss with the diameter of 2 mm. It is important to appreciate that increasing the cross section of the area through which the liquid can be displaced in the dispenser by way of making channels in the walls of the body member can be more beneficial than just uniformly increasing its inner diameter. The reason is that increasing the inner diameter of the body member may result in an undesirable lateral movement of the boss perpendicular to the axis of the dispenser whereas with the help of the channels, the boss movement can be still restricted to essentially a one-dimensional movement along the axis of the dispenser.

Figure 43:
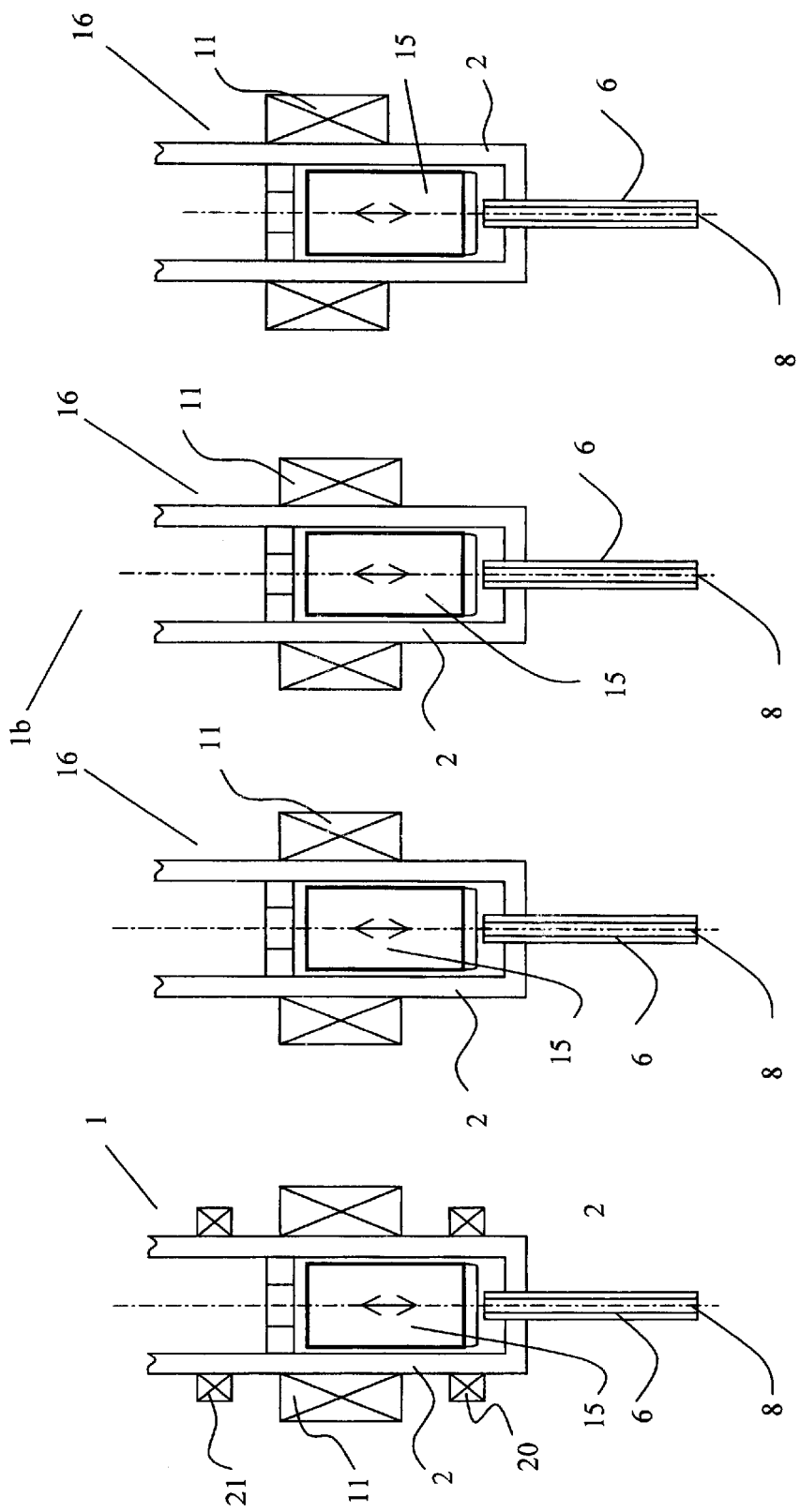
FIG. 43 illustrates an arrangement of a number of dispensers according to the invention.

Referring to FIG. 43, there is illustrated a plurality of dispensers, all indicated by the reference numeral 1b, and one dispenser indicated by the reference numeral 1, which dispenser has sensing coils 20 and 21 which sensing coils are connected to the controller. Effectively, the dispenser 1 is a master dispenser and the remainder of the dispensers 1b are slave dispensers, the actuating coil assemblies being connected to the controller which varies the power exerted on the respective valve bosses 15, depending on the position of the valve boss 15 of the dispenser 1a.

Preferably the dispenser in so far as it comprises the elongate body member the valve seat and nozzle can be manufactured from a suitable polymer material by precision machining or indeed any standard polymer mass production technique such as injection moulding. The purpose of this is to provide a disposable dispenser. The body of the dispenser could be also manufactured of other materials such as steel.

The valve boss as will be appreciated from the description above can be cylindrical, spherical or indeed a body of any geometric shape made from magnetic material for example iron, soft or hard magnetic ferrite, SmCo or NdFeB. It is preferably coated with a polymer or inert layer of another material to prevent chemical reaction between the boss and the liquid dispensed. In order to obtain a good seal with the valve seat, the valve boss may need to be coated with a specially selected soft polymer such as chemically inert rubber. The choice of the materials for the coating on the boss depends on the requirements of the liquids that must be handled by the dispenser. Suitable materials include fluoroelastomers such as VITON, perfluoroelastomers such as KALREZ and ZALAK and for less demanding applications, materials with lower cost could be considered such as NITRILE. TEFLON (PTFE) could be used in conjunction with chemically aggressive liquids. VITON, KALREZ, TEFLON and ZALAK are Du Pont registered trademarks.

The valve boss may be made of magnetic material bonded in a flexible polymer. These materials can have either hard or soft magnetic properties as required. The specific choice of material will be determined by the cost-performance considerations. Materials of families FX, FXSC, FXND manufactured by Kane Magnetics are suitable for certain applications. Other materials such as magnetic rubbers can be also used for certain designs. Making the boss of a mechanically soft material can improve the performance of the seal.

It is important to appreciate that the polymer coating on the boss can consist of two or more layers of different polymers. For example, the first layer could be deposited on the boss to improve the adhesion of the second outer layer with the first one. For certain applications it may be advantageous to have the second layer deposited only on that part of the boss that comes in contact with the seat 43 and in the immediate vicinity.

It will also be appreciated in accordance with the present invention that it does not rely on a positive displacement pump nor indeed does it rely on the conventional normal construction of solenoid valve. At the same time the present invention can, as shown above, be applied with advantage to positive displacement pump assemblies. The essential point then is that the positive displacement pump operates as a source of pressure difference, not as a metering device. Unlike in the conventional solenoid valve, there is no mechanical connection between the valve boss and other parts of the dispenser, similarly there is no mechanically actuated means involved or a spring for closing a valve boss. There is virtually zero dead volume in the apparatus according to the present invention which increases the accuracy particularly where smaller volumes are required. By having the dispenser separate from the actuating coils etc., it is possible to produce a very low cost dispenser which can be easily and rapidly removed thus avoiding cost and cross contamination problems. There is thus great disposability with the present invention. It is also advantageous that the present invention can work at both high and low pressures.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiment hereinbefore described, but may be varied in both construction and detail within the scope of the claims.

What is claimed is:

1. A dispensing assembly for liquid droplets of the order of 30 μl or less in volume comprising:

a pressurised liquid delivery source;

a metering valve body connected to the liquid delivery source, the body comprising an elongated body member having an internal main bore and a base forming an apertured valve seat;

a valve boss in the bore, the cross-sectional area of the valve boss being sufficiently less than that of the main bore to permit the free passage of liquid therebetween;

a nozzle mounted on the base of the body member comprising a dispensing tip and having a nozzle bore communicating between the valve seat and the dispensing tip;

a variable power output valve boss actuator for moving the valve boss in the bore between a closed position engaging the valve seat and an open position spaced-apart from the valve seat;

a valve boss detector for determining the movement of the valve boss within the bore; and a controller connected to the valve boss detector and to the valve boss actuator for varying the power input to the valve boss actuator depending on the movement of the valve boss within the bore.

2. A dispensing assembly for liquid droplets as claimed in claim 1 in which the valve boss detector is a position sensor.

3. A dispensing assembly as claimed in claim 1 in which at least portion of the nozzle adjacent the dispensing tip is of a hydrophobic material.

4. A dispensing assembly for liquid droplets as claimed in claim 2 comprising:

a ferromagnetic material forming part of the valve boss;

an actuating coil assembly forming the valve boss actuator; and a Hall sensor to provide the position sensor.

5. A dispensing assembly for liquid droplets as claimed in claim 2 comprising:

a ferromagnetic material forming part of the valve boss;

at least one actuating coil assembly forming the valve boss actuator; and two spaced-apart Hall sensors to provide the position sensor.

6. A dispensing assembly for liquid droplets as claimed in claim 2, in which the valve boss comprises a ferromagnetic material; the valve boss actuator comprises a pair of spaced-apart actuating coil assemblies; and one of the actuating coil assemblies comprises a source of alternating current to allow the position of the valve boss be detected by measuring the electromagnetic field generated in the other actuating coil assembly.

7. A dispensing assembly for liquid droplets as claimed in claim 2 comprising:
- a valve boss including a ferromagnetic material;
- at least one actuating coil assembly forming the valve boss actuator;
- a pair of spaced-apart sensing coils forming part of the valve boss detector; and
- a separate excitation coil for generating an oscillating magnetic field for the valve boss detector.

8. A dispensing assembly for liquid droplets as claimed in claim 2 in which the valve boss comprises a ferromagnetic material; the valve boss actuator comprises a pair of spaced-apart actuating coil assemblies, at least one of which is powered with alternating current and the position sensor comprises a sensing coil adjacent the body member for receiving the signal induced in the boss by the alternating current.

9. A dispensing assembly for liquid droplets as claimed in claim 2 comprising:
- a ferromagnetic material forming part of the valve boss; and
- a parametric oscillator circuit forming the position sensor, the circuit comprising at least one element coupled to the valve boss, the element being such as to be effected by the position of the valve boss relative thereto to change the characteristics of the oscillations.

10. A dispensing assembly for liquid droplets as claimed in claim 2, in which the valve boss comprises a ferromagnetic material encased in an electrically conducting material, the valve boss actuator comprises at least one actuating coil assembly; and the position sensor comprises a pair of sensing coils coupled with each other by means of eddy currents induced in the boss by one of said sensing coils.

11. A dispensing assembly for liquid droplets as claimed in claim 2, in which the valve boss comprises a ferromagnetic material encased in an electrically conducting material, the valve boss actuator comprises at least one actuating coil assembly; and the position sensor comprises a pair of sensing coils surrounded by a conducting shield adjacent the body member, the two sensing coils being coupled with each other by means of eddy currents induced in the boss by one of said sensing coils.

12. A dispensing assembly as claimed in claim 2 in which at least portion of the length of the nozzle is of a hydrophobic material.

13. A dispensing assembly for liquid droplets as claimed in claim 1, in which the valve boss detector is a velocity sensor.

14. A dispensing assembly for liquid droplets as claimed in claim 13, in which the velocity sensor comprises two sensing coils spaced-apart along the body member for measurement of the electromotive force generated by the moving boss which comprises a ferromagnetic material.

15. A dispensing assembly for liquid droplets as claimed in claim 13, in which the valve boss comprises a ferromagnetic material and the valve boss actuator comprises a pair of spaced-apart actuating coil assemblies, the actuating coil assemblies also being adapted for measurement of the electromotive force generated by the moving boss to provide the velocity sensor.

16. A dispensing assembly for liquid droplets as claimed in claim 13 in which the valve boss comprises a ferromagnetic material; the valve boss actuator comprises at least one actuating coil assembly; and the velocity sensor comprises a sensing coil adjacent the body member for measurement of the electromotive force generated by the moving boss.

17. A dispensing assembly for liquid droplets as claimed in claim 13 in which the valve boss comprises a ferromagnetic material; the valve boss actuator comprises a pair of spaced-apart actuating coil assemblies; and the velocity sensor comprises a sensing coil adjacent the body member for measurement of the electromotive force generated by the moving boss.

18. A dispensing assembly as claimed in claim 13, in which at least portion of the nozzle adjacent the dispensing tip is of a hydrophobic material.

19. A dispensing assembly for liquid droplets as claimed in claim 1, in which there are a plurality of nozzles mounted on the base of the body member.

20. A dispensing assembly for liquid droplets as claimed in claim 19 comprising:
- a valve boss, at least portion of which is of a ferromagnetic material;
- at least one actuating coil assembly forming the valve boss actuator;
- a source of current to power the actuator;
- sensing means in the valve boss; and
- detector to determine the electromotive force generated by the valve boss under the influence of an externally generated signal.

21. A dispensing assembly for liquid droplets as claimed in claim 19 comprising:
- a valve boss, at least portion of which is of a ferromagnetic material;
- at least one actuating coil assembly forming the valve boss actuator;
- a source of current to power the actuator; and
- means in the detector to determine the electromotive force generated by the valve boss under the influence of an externally generated signal and in which the externally generated signal is provided by the actuating coil assembly.

22. A dispensing assembly for liquid droplets as claimed in claim 19 comprising:
- a valve boss, at least portion of which is of a ferromagnetic material;
- at least one actuating coil assembly forming the valve boss actuator;
- a source of current to power the actuator; and
- means in the detector to determine the electromotive force generated by the valve boss under the influence of an externally generated signal and in which the electrical signal is provided by the actuating coil assembly and the sensing means comprises a sensing coil external of the body member.

23. A dispensing assembly for liquid droplets as claimed in claim 19 comprising:
- a valve boss, at least portion of which is of a ferromagnetic material;
- at least one actuating coil assembly forming the valve boss actuator;
- a source of current to power the actuator; and
- means in the detector to determine the electromotive force generated by the valve boss under the influence of an externally generated signal and in which the externally generated signal is an additional alternating current.

24. A dispensing assembly for liquid droplets as claimed in claim 19 in which the valve boss detector is a combined position and velocity sensor.

25. A dispensing assembly for liquid droplets as claimed in claim 19 comprising:
- a valve boss including a ferromagnetic material;
- at least one actuating coil assembly forming the valve boss actuator;
- means in the valve boss detector for measurement of the electromotive force generated by the valve boss when moving under the influence of the current applied to the actuating coil assembly to determine the velocity of the valve boss;
- means for applying the oscillating magnetic field to the valve boss; and
- means in the valve boss detector for measurement of the electromotive force generated by the valve boss under the influence of the oscillating field to determine the position of the valve boss.

26. A dispensing assembly as claimed in claim 19, in which at least portion of the nozzle adjacent the dispensing tip is of a hydrophobic material.

27. A dispensing assembly for liquid droplets as claimed in claim 1 comprising:
- a valve boss, at least portion of which is of a ferromagnetic material;
- at least one actuating coil assembly forming the valve boss actuator;
- a source of current to power the actuator; and
- means in the detector to determine the electromotive force generated by the valve boss under the influence of an externally generated signal.

28. A dispensing assembly for liquid droplets as claimed in claim 27, in which the externally generated signal is provided by the actuating coil assembly.

29. A dispensing assembly for liquid droplets as claimed in claim 27, in which the electrical signal is provided by the actuating coil assembly and the sensing means comprises a sensing coil external of the body member.

30. A dispensing assembly for liquid droplets as claimed in claim 27, in which the electrically generated signal is an additional alternating current.

31. A dispensing assembly as claimed in claim 27, in which at least portion of the nozzle adjacent the dispensing tip is of a hydrophobic material.

32. A dispensing assembly for liquid droplets as claimed in claim 1, in which there are a plurality of metering valve bodies all connected to the one controller.

33. A dispensing assembly for liquid droplets as claimed in claim 1, in which there are a plurality of additional metering valve bodies each having an additional variable power output valve boss actuator and in which the controller is connected to each of the additional valve boss actuators for varying the power input to each of the additional valve boss actuators depending on the position of the other valve boss within its bore.

34. A dispensing assembly for liquid droplets as claimed in claim 1 comprising:
- a valve boss including a ferromagnetic material;
- at least one actuating coil assembly forming the valve boss actuator;
- means in the valve boss detector for measurement of the electromotive force generated by the valve boss when moving under the influence of the current applied to it to determine the velocity of the valve boss;
- means for applying the oscillating magnetic field to the valve boss; and
- means in the valve boss detector for measurement of the electromotive force generated by the valve boss under the influence of the oscillating field to determine the position of the valve boss.

35. A dispensing assembly for liquid droplets as claimed in claim 1 in which the valve boss detector is a combined position and velocity sensor.

36. A dispensing assembly for liquid droplets as claimed in claim 1, in which the valve boss sensor is an acceleration sensor.

* * * * *